US012358971B2

(12) United States Patent
Branco et al.

(10) Patent No.: US 12,358,971 B2
(45) Date of Patent: Jul. 15, 2025

(54) ARENA VIRUS MONOCLONAL ANTIBODIES AND USES

(71) Applicants: THE ADMINISTRATORS OF THE TULANE EDUCATIONAL FUND, New Orleans, LA (US); THE SCRIPPS RESEARCH INSTITUTE, La Jolla, CA (US); THE BOARD OF REGENTS OF THE UNIVERSITY OF TEXAS SYSTEM, Austin, TX (US); ZALGEN LABS, LLC, Germantown, MD (US)

(72) Inventors: Luis M. Branco, Germantown, MD (US); Robert F. Garry, New Orleans, LA (US); James E. Robinson, New Orleans, LA (US); Erica O. Saphire, La Jolla, CA (US); Kathryn M. Hastie, La Jolla, CA (US); Thomas W. Geisbert, Albany, TX (US)

(73) Assignees: The Administrators of the Tulane Educational Fund, New Orleans, LA (US); The Boad of Regents of the University of Texas System, Austin, TX (US); The Scripps Resesrch Institute, La Jolla, CA (US); Zalgen Labs, LLC, Germantown, MD (US)

( * ) Notice: Subject to any disclaimer, the term of this patent is extended or adjusted under 35 U.S.C. 154(b) by 0 days.

(21) Appl. No.: 18/392,147

(22) Filed: Dec. 21, 2023

(65) Prior Publication Data

US 2024/0352095 A1 Oct. 24, 2024

Related U.S. Application Data

(62) Division of application No. 17/520,338, filed on Nov. 5, 2021, now abandoned, which is a division of application No. 16/466,544, filed as application No. PCT/US2017/064744 on Dec. 5, 2017, now Pat. No. 11,198,723.

(60) Provisional application No. 62/430,225, filed on Dec. 5, 2016.

(51) Int. Cl.
*C07K 16/10* (2006.01)
*A61P 31/14* (2006.01)

(52) U.S. Cl.
CPC .............. *C07K 16/10* (2013.01); *A61P 31/14* (2018.01); *C07K 2317/21* (2013.01); *C07K 2317/31* (2013.01); *C07K 2317/33* (2013.01); *C07K 2317/565* (2013.01); *C12N 2760/10011* (2013.01)

(58) Field of Classification Search
CPC ...................................................... C07K 16/10
See application file for complete search history.

(56) References Cited

U.S. PATENT DOCUMENTS

| | | | |
|---|---|---|---|
| 4,816,567 | A | 3/1989 | Cabilly et al. |
| 5,219,740 | A | 6/1993 | Miller et al. |
| 5,422,120 | A | 6/1995 | van der Meij et al. |
| 5,530,101 | A | 6/1996 | Queen et al. |
| 5,565,332 | A | 10/1996 | Hoogenboom et al. |
| 5,580,717 | A | 12/1996 | Dower et al. |
| 5,580,859 | A | 12/1996 | Felgner et al. |
| 5,585,362 | A | 12/1996 | Wilson et al. |
| 5,693,762 | A | 12/1997 | Queen et al. |
| 5,733,743 | A | 3/1998 | Johnson et al. |
| 5,807,715 | A | 9/1998 | Morrison et al. |
| 5,866,692 | A | 2/1999 | Shitara et al. |
| 6,180,370 | B1 | 1/2001 | Queen et al. |
| 6,265,150 | B1 | 7/2001 | Terstappen et al. |
| 6,331,415 | B1 | 12/2001 | Cabilly et al. |
| 6,376,471 | B1 | 4/2002 | Lawrence, III et al. |
| 6,413,942 | B1 | 7/2002 | Felgner et al. |
| 6,436,908 | B1 | 8/2002 | Koch et al. |
| 2014/0271580 | A1 | 9/2014 | Garry et al. |

FOREIGN PATENT DOCUMENTS

| | | | |
|---|---|---|---|
| CN | 105296507 | A | 2/2016 |
| CN | 105548539 | A | 5/2016 |
| WO | 20080124176 | A2 | 10/2008 |

OTHER PUBLICATIONS

Xiang, J., et al., 1991, Modification in framework region 1 results in a decreased affinity of chimeric anti-TAG72 antibody, Mol. Immunol. 28(1/2):141-148.*
Xiang, J., et al., 1995, Framework residues 71 and 93 of the chimeric B72.3 antibody are major determinants of the conformation of heavy-chain hypervariable loops, J. Mol. Biol.253:385-390.*
Sela-Culang, I., Oct. 2013, The structural basis of antibody-antigen recognition, Front. Immunol. 4, Article 302, pp. 1-13.*
Andersen, K.G. et al., Clinical Sequencing Uncovers Origins and Evolution of Lassa Virus, Cell 162, 738-750 (2015).
Auperin, D. D. et al., Nucleotide Sequence of the Glycoprotein Gene and Intergenic Region of the Lassa Virus S Genome RNA, Virology 154, 155-167 (1986).
Beyer, W.R. et al., Endoproteolytic Processing of the Lymphocytic Choriomeningitis Virus Glycoprotein by the Subtilase SKI-1/S1P, Journal of Virology 77 (5), 2866-2872 (2003).

(Continued)

*Primary Examiner* — Jeffrey S Parkin
(74) *Attorney, Agent, or Firm* — Olson & Cepuritis, Ltd.

(57) ABSTRACT

Disclosed herein are compositions comprising recombinant arenavirus monoclonal antibodies and antigen-binding fragments thereof, as well as therapeutic methods using the antibodies. In some embodiments, the antibodies provide pan-arenavirus protection against a number of arenavirus types and strains.

20 Claims, 10 Drawing Sheets

Specification includes a Sequence Listing.

(56) References Cited

OTHER PUBLICATIONS

Branco, L.M. et al., Lassa Virus-Like Particles Displaying All Major Immunological Virology Determinants as a Vaccine Candidate for Lassa Hemorrhagic Fever, Virology Journal 7 (279), 1-19 (2010).
Branco, L.M. et al., Emerging Trends in Lassa Fever: Redefining The Role of Immunoglobulin M and Inflammation in Diagnosing Acute Infection, Virology Journal 8 (478), 1-15 (2011).
Buchmeier, M.J. et al., Monoclonal Antibodies to Lymphocytic Choriomeningitis Virus React With Pathogenic Arenaviruses, Nature 288, 486-487 (1980).
Buchmeier, M.J. et al., Arenaviruses: Protein Structure and Function, Current Topics in Microbiology and Immunology, 288, 159-173 (2002).
Buck, D.W. et al., Monoclonal Antibodies Specific for Cell Culture Mycoplasmas, In Vitro 18 (4), 377-381 (1982).
Burnette, W.N., Western Blotting: Electrophoretic Transfer of Proteins From Sodium Dodecyl Sulfate—Polyacrylamide Gels to Unmodified Nitrocellulose and Radiographic Detection With Antibody and Radioiodinated Protein A, Analytical Biochemistry 112, 195-203 (1981).
Chiou, H.C. et al., In Vivo Gene Therapy Via Receptor-Mediated DNA Delivery, Gene Therapeutics: Methods and Applications of Direct Gene Transfer 141-156, Birkhauser Boston (1994).
Clegg, J.C.S et al., Structural and Cell-Associated Proteins of Lassa Virus, Journal General Virology 64, 1127-1136 (1983).
Curiel, D.T. et al., High-Efficiency Gene Transfer Mediated by Adenovirus Coupled to DNA-Polylysine Complexes, Human Gene Therapy 3, 147-154 (1992).
Dayhoff, M.O. et al., A Model of Evolutionary Change in Proteins, Atlas of Protein Sequence and Structure, 345-358 (1978).
Eichler, R. et al., Lassa Virus Glycoprotein Signal Peptide Displays a Novel Topology With an Extended Endoplasmic Reticulum Luminal Region, The Journal of Biological Chemistry 279 (13), 12293-12299 (2004).
Eichler, R. et al., Identification of Lassa Virus Glycoprotein Signal Peptide as a Trans-Acting Maturation Factor, EMBO Reports 4 (11), 1084-1088 (2003).
Eichler, R. et al., Signal Peptide of Lassa Virus Glycoprotein GP-C Exhibits an Unusual Length, FEBS Letters 538, 203-206 (2003).
Elagoz, A. et al., Biosynthesis and Cellular Trafficking of the Convertase SKI-1-S1P, The Journal of Biological Chemistry 277 (13), 11265-11275 (2002).
Findeis, M.A. et al., Targeted Delivery of DNA for Gene Therapy Via Receptors, Trends Biotechnology 11, 202-205 (1993).
Grove, J.N. et al., Capacity Building Permitting Comprehensive Monitoring of a Severe Case of Lassa Hemorrhagic Fever in Sierra Leone With a Positive Outcome: Case Report, Virology Journal 8 (314), 1-14 (2011).
Hartnett, J.N. et al., Current and Emerging Strategies for the Diagnosis, Prevention and Treatment of Lassa Fever, Future Virology 10 (5), 559-584 (2015).
Higgins, D.G. et al., Fast and Sensitive Multiple Sequence Alignments on a Microcomputer, Cabios Communications 5 (2), 151-153 (1989).
Hufert, F.T. et al., Epitope Mapping of the Lassa Virus Nucleoprotein Using Monoclonal Anti-Nucleocapsid Antibodies, Arch Virology 106, 201-212 (1989).
Johnson, K.S. et al., Human Antibody Engineering, Current Opinion in Structural Biology 3, 564-571 (1993).
Kohler, G. et al., Continuous Cultures of Fused Cells Secreting Antibody of Predefined Specificity, Nature 256, 495-497 (1975).
Lenz, O. et al., Identification of a Novel Consensus Sequence at the Cleavage Site of the Lassa Virus Glycoprotein, Journal of Virology 74 (23), 11418-11421 (2000).
Lonberg, N. et al., Human Antibodies From Transgenic Mice, International Reviews of Immunology 13, 65-93 (1995).
Lukashevich, I.S. et al., Lassa Virus Activity in Guinea: Distribution of Human Antiviral Antibody Defined Using Enzyme-Linked Immunosorbent Assay With Recombinant Antigen, Journal of Medical Virology 40, 210-217 (1993).
McCafferty, J. et al., Phage Antibodies: Filamentous Phage Displaying Antibody Variable Domains, Nature 348, 552-554 (1990).
McCormick, J.B. et al., Lassa Fever, Current Topics in Microbiology and Immunology 262, 75-109 (2002) .
Meulen, J.T. et al., Characterization of Human CD4+ T-Cell Clones Recognizing Conserved and Variable Epitopes of the Lassa Virus Nucleoprotein, Journal of Virology 74 (5), 2186-2192 (2000).
Meulen, J.T. et al., Detection of Lassa Virus Antinucleoprotein Immunoglobulin G (IgG) and IgM Antibodies by a Simple Recombinant Immunoblot Assay for Field Use, Journal of Clinical Microbiology 36 (11), 3143-3148 (1998).
Myers, E.W. et al., Optimal Alignments in Linear Space, CABIOS 4 (1) 11-17 (1988).
Peeters, K. et al., Production of Antibodies and Antibody Fragments in Plants, Vaccine 19 2756-2761 (2001).
Philip, R. et al., Efficient and Sustained Gene Expression in Primary T Lymphocytes and Primary and Cultured Tumor Cells Mediated by Adeno-Associated Virus Plasmid DNA Complexed to Cationic Liposomes, Molecular and Cellular Biology 14 (4), 2411-2418 (1994).
Pollock, D.P. et al., Transgenic Milk as a Method for the Production of Recombinant Antibodies, Journal of Immunological Methods 231, 147-157 (1999).
Robinson, D.F., Comparison of Labeled Trees With Valency Three, Journal of Combinatorial Theory 11, 105-119 (1971).
Ruo, S.L. et al., Antigenic Relatedness Between Arenaviruses Defined at the Epitope Level by Monoclonal Antibodies, Journal of General Virology 72, 549-555 (1991).
Saitou, N. et al., The Neighbor-Joining Method: A New Method for Reconstructing Phylogenetic Trees, Molecular Biology Evol. 4 (4):406-425 (1987).
Sanchez, A. et al., Junin Virus Monoclonal Antibodies: Characterization and Cross-Reactivity With Other Arenaviruses, Journal General Virology 70, 1125-1132 (1989).
Shaffer, J.G. et al., Lassa Fever in Post-Conflict Sierra Leone, PLOS Neglected Tropical Diseases 8 (3), e2748, 1-12 (2014).
Spiropoulou, C.F. et al., New World Arenavirus Clade C, but Not Clade A and B Viruses, Utilizes a-Dystroglycan as its Major Receptor, Journal of Virology 76 (10), 5140-5146 (2002).
Wilbur, W.J. et al., Rapid Similarity Searches of Nucleic Acid and Protein Data Banks, PNAS 80, 726-730 (1983).
Winter, G. et al., Making Antibodies by Phage Display Technology, Annual Review Immunology 12, 433-455 (1994).
Woffendin, C. et al., Nonviral and Viral Delivery of a Human Immunodeficiency Virus Protective Gene Into Primary Human T Cells, PNAS 91, 11581-11585 (1994).
Wu, G.Y. et al., Receptor-Mediated Gene Delivery in Vivo, Partial Correction of Genetic Analbuminemia in Nagase Rats, The Journal of Biological Chemistry 266 (22), 14338-14342 (1991).
Wu, G.Y. et al., Receptor-Mediated Gene Delivery and Expression in Vivo, The Journal of Biological Chemistry 263(29), 14621-14624 (1988).
Wu, C.H., et al., Targeting Genes: Delivery and Persistent Expression of a Foreign Gene Driven by Mammalian Regulatory Elements in Vivo, The Journal of Biological Chemistry 264 (29), 16985-16987 (1989).
Wu, G.Y. et al., Incorporation of Adenovirus Into a Ligand-based DNA Carrier System Results in Retention of Original Receptor-Mediated Specificity and Enhances Targeted Gene Expression, The Journal of Biological Chemistry 269 (15), 11542-11546 (1994).
York, J. et al., Genetic Analysis of Heptad-Repeat Regions in the G2 Fusion Subunit of the Junin Arenavirus Envelope Glycoprotein, Virology 343, 267-274 (2005).
York, J. et al., The Signal Peptide of the Junin Arenavirus Envelope Glycoprotein is Myristoylated and Forms an Essential Subunit of the Mature G1-G2 Complex, Journal of Virology 78 (19), 10783-10792 (2004).
Both, L. et al., Monoclonal Antibodies for Prophylactic and Therapeutic Use Against Viral Infections, Vaccine 31, 1553-1559 (2013).
Branco, L.M. et al., Shedding of Soluble Glycoprotein 1 Detected During Acute Lassa Virus Infection in Human Subjects, Virology Journal 7 (1), Biomed Central, London, GB, 306 (2010).

(56) References Cited

OTHER PUBLICATIONS

Buchmeier, M.J. et al., Monoclonal Antibodies to Lymphocytic Choriomeningitis and Pichinide Viruses: Generation, Characterization, and Cross-Reactivity With Other Arenaviruses, Virology 113 (1), 73-85 (1981).
Cross, R.W. et al., Antibody Therapy for Lassa Fever, Current Opin. Virology 37, 97-104 (2019).
Cross, R.W. et al., Treatment of Lassa Virus Infection in Outbred Guinea Pigs With First-in-Class Human Monoclonal Antibodies, Antiviral Research 133, 218-222 (2016).
Fisher-Hoch, S.P. et al., Effective Vaccine for Lassa Fever, Journal of Virology 74 (15), 6777-6783 (2000).
Hastie, K.M. et al., Structural Basis for Antibody-Mediated Neutralization of Lassa Virus, Science 356 (6341), 923-928 (2017).
Lukashevich, I.S., Advanced Vaccine Candidates for Lassa Fever, Viruses 4, 2514-2557 (2012).
Mahmutovic, S. et al., Molecular Basis for Antibody-Mediated Neutralization of New World Hemorrhagic Fever Mammarenaviruses, Cell Host & Microbe 18 (6), 705-713 (2015).
Mire, C.E., Human-Monoclonal-Antibody Therapy Protects Nonhuman Primates Against Advanced Lassa Fever, Nature Medicine 23 (10) 1146-1149 (2017).
Robinson, J.E. et al., Most Neutralizing Human Monoclonal Antibodies Target Novel Epitopes Requiring Both Lassa Virus Glycoprotein Subunits, Nature Communications 7 (11544), 1-14 (2016).
Robinson, J.E. et al., Supplementary Information for Most Neutralizing Human Monoclonal Antibodies Target Novel Epitopes Requiring Both Lassa Virus Glycoprotein Subunits, Nature Communications 7, 1-13 (2016).
Zapata, J.C. et al., Improving the Breadth of the Host's Immune Response to Lassa Virus, Pathogens 7, 84:doi:10.3390/pathogens7040084, 1-18 (2018).
Zenke, M., et al., Receptor-Mediated Endocytosis of Transferrin-Polycation Conjugates: An Efficient Way to Introduce DNA Into Hematopoietic Cells, PNAS 87, 3655-3659 (1990).
Xiang, J, et al., Framework Residues 71 and 93 of the Chimeric B72.3 Antibody are Major Determinants of the Conformation of Heavy-chain Hypervariable Loops, J. Mol. Biol. 253:385-390 (1995).
Xiang, J., et al., Modification in Framework Region I Results in a Decreased Affinity of Chimeric Anti-TAG72 Antibody, Mol. Immunol. 28 (1/2):141-148 (1991).
Sela-Culang, I., et al., The Structural Basis of Antibody-Antigen Recognition, Front. Immunol. 4 (Article 302), 1-13 (2013).
Robinson, J. E., et al., Most Neutralizing Human Monoclonal Antibodies Target Novel Epitopes Requiring Both Lassa Virus Glycoprotein Subunits, Nat. Comm. 7:11544, pp. 1-14 (2016).

* cited by examiner

```
                                                      CDR1: +++++++++
10.4B    METDTLLLWVLLLWVPGSTGDQVQLVQSGGGVVQPGRSLRVSCVTSGFNF-RAYGMHWVR
19.7E    METDTLLLWVLLLWVPGSTGDEVQLVESGGGLVRPGGSLRLSCAASGFSF-SSYSMHWVR
2.9D     METDTLLLWVLLLWVPGSTGDEVQLVESGGGLVKPGGSLRLSCAASGFTF-TRFTLTWVR
25.6A    METDTLLLWVLLLWVPGSTGDQVQLQESGGGLVKAGGSLRLSCAASGFMF-ERYSLHWVR
36.1F    METDTLLLWVLLLWVPGSTGDQVQLQESGAGLVKPSETLSLTCAVSGGPF-SGAYWTWIR
36.9F    METDTLLLWVLLLWVPGSTGDEVQLVQSGGGLVKAGGSLKLSCGASGFTF-SSYSMSWVR
37.2D    METDTLLLWVLLLWVPGSTGDEVQLVQSGAEVKKPGASVKVSCKASGYTF-TKYGISWVR
37.2G    METDTLLLWVLLLWVPGSTGDEVQLVESGGGLVKPGGSRRLSCAASGFTF-SRDTMTWVR
37.7H    METDTLLLWVLLLWVPGSTGDEVQLVQSGGGLVKAGGSLRLSCAASGFTF-STYSMNWIR
8.9F     METDTLLLWVLLLWVPGSTGDQGTLRESGPGLVRPSETLSLTCGVSGYSISSGYYWGWIR
NE13     METDTLLLWVLLLWVPGSTGDEVQLVESGGGLVKPGGSLRLSCVASGFTF-SSYSMNWVR
12.1F    METDTLLLWVLLLWVPGSTGDQVQLQESGAGLLKPSETLSLSCTVDGESF-NGFFWTWIR
9.8A     METDTLLLWVLLLWVPGSTGDEVQLVQSGGRLVQPGGSLRLSCVASGFTF-SSHAMSWVR
18.5C    METDTLLLWVLLLWVPGSTGDEVQLVESGGGLVRPGGSLRLSCAAAGFTF-KSYSMNWVR
8.11G    METDTLLLWVLLLWVPGSTGDQVQLQESGPGLVKPSETLSLTCSISGVST-RNYYWSWIR
25.10C   METDTLLLWVLLLWVPGSTGDQVQLQESGGGLVKPGGSLRLSCTASGFNF-NKYNMNWVR
         *********************:  * :**  : : . :  ::*   *         *:*

                CDR2: ^^^^^^^^^^                        CDR3: #
10.4B    QIPGKGLEWVADIWSA-ETNRHYADSVKGRFTISRDNSKSTLYLQMNSLRAEDTGVYFCA
19.7E    HVPGKGLVWVSYINSD-GSTKIYADSVKGRFSISRDNAKNKLYLQMDSLRVEDTAVYSCV
2.9D     QAPGKGLEWVSSISS-GSSDINYADSVKGRFTISRDNARNSLFLQMSSLRVDDTAVYYCA
25.6A    QTPGKGLEWVSSISSLSGSHINYADSVKGRFTISRDNAKNSLSLQMNSLRVEDTAIYYCA
36.1F    QTPGKGLEWIGEAGRS--GTTNYNPSLKSRVTISLDTSKSQFSLKLTSVTAADTAVYFCG
36.9F    QAPGKGLEWVSYISS-GGSSIHYADSVKGRFTISRDNAKNSLYLQMKNLRVDDTGRYYCV
37.2D    QAPGQGLEWMGWISAF-NGYTRYGQRFQGKVTMTTDTSTNTASLEVRTLTSNDTAVYYCA
37.2G    QAPGKGLEWVASISS-GSSDINYADSVKGRFTISRDNGKNSLYLHMNSLRADDTAIYYCA
37.7H    QAPGKGLEWVASISSRSGSHINYVDSVKGRFTISRDNARDLLYLQMNSLRVDDSALYYCA
8.9F     QPPGKGLEWIGNIYRS--GSTYYNPSLKSRVTVSIDTSKNQFSLKLNSVTAADTAVYYCA
NE13     QAPGKGLEWVSSISS-GSSYIEYADSVKGRLTISRDNAKKSLYLQLNSLRAEDTAVYYCA
12.1F    QPPGKGLEWIGEINHL--ASTGYNPSLKSRVTISVDTSKNQFSLKLTSVTAADTAVYYCA
9.8A     QAPGKGLEWVSGFSGS-SGTTKYADSVKGRFTISRDNSKKTLYLQMNSLRAEDTAVYYCA
18.5C    QAPGRGLEWVSSITS-GGSKTYYADVVKGRFTVSRDNAKQSLYLQMNSLRAEDTAIYFCA
8.11G    QSPGKGLEWIGYIFNI--GTTNYNPSLKSRLTISVDTSKNQFSLKITSVTAADTAVYYCA
25.10C   QAPGKGLEWVSSISAL-STYIYYADSLKGRFTVSRDNAKNSLFLQMNSLRDDDTAVYYCA
         : **:** *:.            *    .:.:.::: *.. .    *.: .:    *:. * *

  CDR3:  ##############################
10.4B    KARP----GY--------------DYVVDLWGQGTLVIVSSASTKGPSVFPLAPCSRSTS
19.7E    RLVHY-------------------DWSPFVWGQGTLVTVSSASTKGPSVFPLAPSSKSTS
2.9D     KDPRSGISG---------------RYGMDVWGQGTTVIVSSASTKGPSVFPLAPCSRSTS
25.6A    RDRRSGSS----------------PVPLDVWGQGTTVTVSSASTKGPSVFPLAPSSKSTS
36.1F    RRQIMSLSN-------------LYKRPVDSWGRGTPVIVSSASTKGPSVFPLAPSSKSTS
36.9F    RDPRSGISG---------------RYGMDVWGQGTTVTVSSASTKGPSVFPLAPSSKSTS
37.2D    RQYPDQYSSSGW----------PRLFAMDVWGQGTTVIVSPASTKGPSVFPLAPSSKSTS
37.2G    RDPRSGISG---------------RYGMDVWGQGTTVTVSSASTKGPSVFPLAPSSKSTS
37.7H    RDRRSGTS----------------PLPLDVWGQGTTVTVFSASTKGPSVFPLAPSSKSTS
8.9F     RSGIKVADDYYYEMDVWGQGTDDYSYAMDVWGQGTTVTVSSASTKGPSVFPLAPSSKSTS
NE13     RHT-ARIDS---------------YHGMDVWGQGTTVTVSSASTKGPSVFPLAPSSKSTS
12.1F    RGYSYGFAW-------------PNYHYLDVWGKGTTVTVSSASTKGPSVFPLAPSSKSTS
9.8A     KGFSPFRGVQ--------------FPYFDYWGQGTLVTVSSASTKGPSVFPLAPSSKSTS
18.5C    RSLHSTSQ----------------PSYMDVWGRKITVIVSSASTKGPSVFPLAPSSKSTS
8.11G    SGFEYGDY------------------TFDYWGQGTPVTVSSASTKGPSVFPLAPSSKSTS
25.10C   REIRRAS-----------------TWSADLWGRGTLVTVSSASTKGPSVFPLAPSSKSTS
                                      **:   * *  *************.*:***
```

FIG. 7

```
10.4B    GGTAALGCLVKDYFPEPVTVSWNSGALTSGVHTFPAVLQSSGL-----------------
19.7E    GGTAALGCLVKDYFPEPVTVSWNSGALTSGVHTFPAVLQSSGLYSLSSVVTVPSSSLGTQ
2.9D     GGTAALGCLVKDYFPEPVTVSWNSGALTSGVHTFPAVLQSSGLYSLSSVVTVPSSSLGTQ
25.6A    GGTAALGC----------------------------------------------------
36.1F    GGTAALGCLVKDYFPEPVTVSWNSGALTSGVHTFPAVLQSSGLYSLSSVVTVPSSSLGTQ
36.9F    GGTAALGCLVKDYFPEPVTVSWNSGALTSGVHTFPAVLQSSGLYSLSSVVTVPSSSLGTQ
37.2D    GGTAALGCLVKDYFPEPVTVSWNSGALTSGVHTFPAVLQSSGLYSLSSVVTVPSSSLGTQ
37.2G    GGTAALGCLVKDYFPEPVTVSWNSGALTSGVHTFPAVLQSSGLYSLSSVVTVPSSSLGTQ
37.7H    GGTAALGCLVKDYFPEPVTVSWNSGALTSGVHTFPAVLQSSGLYSLSSVVTVPSSSLGTQ
8.9F     GGTAALGCLVKDYFPEPVTVSWNSGALTSGVHTFPAVLQSSGLYSLSSVVTVPSSSLGTQ
NE13     GGTAALGCLVKDYFPEPVTVSWNSGALTSGVHTFPAVLQSSGLYSLSSVVTVPSSSLGTQ
12.1F    GGTAALGCLVKDYFPEPVTVSWNSGALTSGVHTFPAVLQSSGLYSLSSVVTVPSSSLGTQ
9.8A     GGTAALGCLVKDYFPEPVTVSWNSGALTSGVHTFPAVLQSSGLYSLSSVVTVPSSSLGTQ
18.5C    GGTAALGCLVKDYFPEPVTVSWNSGALTSGVHTFPAVLQSSGLYSLSSVVTVPSSSLGTQ
8.11G    GGTAALGCLVKDYFPEPVTVSWNSGALTSGVHTFPAVLQSSGLYSLSSVVTVPSSSLGTQ
25.10C   GGTAALGCLVKDYFPEPVTVSWNSGALTSGVHTFPAVLQSSGLYSLSSVVTVPSSSLGTQ
         ********

10.4B    ------------------------------------------------------------
19.7E    TYICNVNHKPSNTKVDKKVEPQSCDKTHTCPPCPAPELL---------------------
2.9D     TYICNVNHKPSNTKVDKRVEPKSCDKTHTCPPCPAPELLGGPSVFLFPPKPKDTLMISRT
25.6A    ------------------------------------------------------------
36.1F    TYICNVNHKPSNTKVDKRVEPKSCDKTHTCPPCPAPELLGGPSVFLFPPX----------
36.9F    TYICNVNHKPSNTKVDKRVEPKSCDKTHTCPPCPAPELLGGPSVFLFPPNPRTPS*S---
37.2D    TYICNVNHKPSNTKVDKRVEPKSCDKTHTCPPCPAPELLGGPSVFLF-------------
37.2G    TYICNVNHKPSNTKVDKRVEPKSCDKTHTCPPCPAPELLGGPSVFLFPPKPKDTLMISRT
37.7H    TYICNVNHKPSNTKVDKRVEPKSCDKTHTCPPCPAPELLGGPSVFLFPPKPKDTLMISRT
8.9F     TYICNVNHKPSNTKVDKRVEPKSCDKTHTCPPCPAPELLGGPSVFLFPPKPKDTLMX---
NE13     TYICNVNHKPSNTKVDKRVEPKSCDKTHTCPPCPAPELLGGPSVFLFPPKPKDTLMISRT
12.1F    TYICNVNHKPSNTKVDKRVEPKSCDKTHTCPPCPAPELLGGPSVFLXPPKPKDTLMISRT
9.8A     TYICNVNHKPSNTKVDKRVEPKSCDKTHTCPPCPAPELLGGPSVFLFPPKPRTPS*SPGP
18.5C    TYICNVNHKPSNTKVDKRVEPKSCDKTHTCPPCPAPELLGGPSVFLFPPKPKDTLMISRT
8.11G    TYICNVNHKPSNTKVDKRVEPKSCDKTHTCPPCPAPELLGGPSVFLFPPKPKDTLMIFRT
25.10C   TYICNVNHKPSNTKVDKRVEPKSCDKTHTCPPCPAPELLGGPSVFLFPPNPRTPS-----

10.4B    --------------------------
19.7E    --------------------------
2.9D     PEVTCVVVDVS---------------
25.6A    --------------------------
36.1F    --------------------------
36.9F    --------------------------
37.2D    --------------------------
37.2G    PEVTCVVVDVSHEDPEVKFNWYVDGV
37.7H    PEVTCVVVDVSHE-------------
8.9F     --------------------------
NE13     P-------------------------
12.1F    PEVTCVVVDVS---------------
9.8A     --------------------------
18.5C    PEVTC---------------------
8.11G    PEVTCVVVDVS---------------
25.10C   --------------------------
```

FIG. 7 Cont.

```
                                                                     CDR1: +++++++++++
10.4B      METDTLLLWVLLLWVPGSTGDEIVLTQSPSSLSASVGDRVTITCRASRDI------NTYL
19.7E      METDTLLLWLLLLWVPGSTGDEIVLTQSPSTLSASVGDRVTITCRASQSI------NNWL
2.9D       MKTDTLLLWVLLLWVPGSTGDDIVLTQSPDSLAVSLGERATINCKSSQSVLYSSNNKNYL
25.6A      METDTLLLWVLLLWVPGSTGDLPVLTQ-PASVSGSPGQSITISCTGTSSDV---GAYNYV
36.1F      METDTLLLWVLLLWVPGSTGDEIVLTQSPGTLSLSPGERATLSCRASQSVT-----KNYL
36.9F      METDTLLLWVLLLWVPGSTGDDIVMTQSPDSLAVSLGERATINCKSSQTVLFTS---YYV
37.2D      METDTLLLWVLLLWVPGSTGDETTLTQSPATLSVSPGETATLSCRASQNVI-----N-NL
37.2G      METDTLLLWVLLLWVPGSTGDDIVLTQSPGTLSLSPGERATLSCRASQSVN-----SIFL
37.7H      METDTLLLWVLLLWVPGSTGDQSALTQ-PASVSGSPGQSITISCTGTGSDI---GGYNFV
8.9F       METDTLLLWVLLLWVPGSTGDQAGLTQ-PASVSGSPGQSITISCTAANSDI---GDFNFV
NE13       METDTLLLWVLLLWVPGSTGDETTLTQSPGTLSLSPGERATLSCRASQSVS-----STYL
12.1F      METDTLLLWVLLLWVPGSTGDETTLTQSPATLSLSPGERATLSCRASQSVS-----S-YL
9.8A       METDTLLLWVLLLWVPGSTGDDIVMTQSPSTLSASVGDRVTITCRASQSI------DRWL
18.5C      METDTLLLWVLLLWVPGSTGDDIQMTQSPGTLSLSPGERATLSCRASQSVI-----SYYV
8.11G      METDTLLLWVLLLWVPGSTGDEIVLTQSPATLSVSPGGRASLSCRASQSIG-------DKL
25.10C     METDTLLLWVLLLWVPGSTGDDIQMTQSPSSLSASVGDRVIITCRASQSI------SSSL
           *:*******:***********    :** *  ::: * *     :.* .:          :

                         CDR2: ^^^                             CDR3: #####
10.4B      GWFQQRPGKAPKSLIYGASNLQNGVPSRFSGSGSGTYFTLTINGLQTEDFATYYCQQYSI
19.7E      AWYQEKPGKAPKLLINKASSLESGVPSRFSGSGSGTEFTLTITSLQPDDFATYYCQQYNS
2.9D       AWYQQKPGQPPKLLIYWASTRESGVPDRFSGSGSGTDFTLTISSLQAEDVAVYYCQQYYS
25.6A      SWYQQHPGKAPKLIIYEVKIRPSGVSNRFSGSKSGNTASLTISGLQAEDEADYFCSSYST
36.1F      AWYQQKPGQAPTLVIYDASTRASGIPDRFIGSGSGTDFTLTISRLEPEDFAVYYCHQYGS
36.9F      AWYQQKPGQPPKLLFSGASSRESGVPDRFSAGGSGTDFYLTINSLQAEDVADYYCQQYHT
37.2D      AWYQQKPGQAPRLLIYGASTRATGIPARFSGSGSGTEFTLTISSMQSEDFAVYYCQQYND
37.2G      AWYQQKPGQAPRLLIYGASSRATGIPDRFSGSGSGTDFTLTISRLEPEDFAVYYCQQYHS
37.7H      SWYQQYPGKAPKLIIYEVRIRASGVSNRFSGSKSGNTASLTISGLQAEDEADYYCNSYSI
8.9F       SWYQQRPDKAPKLMVYEVSSRPSGVSNRFSGSKSGNTASLTISGLQAEDEADYYCTSYTS
NE13       AWYQQKPGQSPRLLIYGASSRATGIPDRFSGSGSGTQFTLTINRLEPEDFAVYYCQQFGS
12.1F      AWYQHKPGQAPRLLIYGASKRATGIPSRFSGSGSGTDFSLTISSLEPEDFAVYYCQHRSD
9.8A       AWYQQKPGKAPKLLIYQASSLERGVPSRFSGSGSGTEFTLTISSLQPDDFATYYCQQYNG
18.5C      AWYQHKGGQAPRLLIYGASSRATGVPDRFSGSGSGTDFTLTISSLEPEDFALYYCQYYGS
8.11G      SWYQQKPGQAPRLVIYGAYTRATDISPRFSGSRSGTDFNLTISRMQSGDFAVYFCQQYEN
25.10C     NWYQQKPGKAPKLLIYAAVNLETGVPSRFSGSGFGTDFTLAISNVQPEDFATYYCQQSDT
            *:*.   .: *   :.  .      .:   **  ..   *.    *:*. ::   *  *  *:*

     CDR3: #####
10.4B      Y-PLSLGGGTKADMKR-TVAAPSVFIFPPSDEQLKSGTASVVCLLNNFYPREAKVQWKVD
19.7E      N-SWTFGQGTKVDMKR-TVAAPSVFIFPPSDEQLKSGTASVVCLLNNFYPREAKVQWKVD
2.9D       T-PPTFGQGTKVEIKR-TVAAPSVFIFPPSDEQLKSGTASVVCLLNNFYPREAKVQWKVD
25.6A      NSPWVFGGGTKVTVLRQPKAAPSVTLFPPSSEELQANKATLVCLISDFYPGAVTVAWKAD
36.1F      SPPYTFGRGTKLEIKR-TVAAPSVFIFPPSDEQLKSGTASVVCLLNNFYPREAKVQWKVD
36.9F      P-PFTFGGGTKLEIRR-TVAAPSVFIFPPSDEQLKSGTASVVCLLNNFYPREAKVQWKVD
37.2D      W-PRSFGQGTRLDIRR-TVAAPSVFIFPPSDEQLKSGTASVVCLLNNFYPREAKVQWKVD
37.2G      SPKLTFGGGTKVEIKR-TVAAPSVFIFPPSGEQLKSGTASVVCLLNNFYPREAKVQWKVD
37.7H      HSPWVFGGGTKLTVLRQPKAAPSVTLFPPSSEELQANKATLVCLISDFYPGAVTVAWKAD
8.9F       SSTFVFGTGTKVTVLGQPKANPTVTLFPPSSEELQANKATLVCLISDFYPGAVTVAWKAD
NE13       --PWTFGQGTKVEIKR-TVAAPSVFIFPPSDEQLKSGTASVVCLLNNFYPREAKVQWKVD
12.1F      W-RTTFGQGTRLEIKR-TVAAPSVFIFPPSDEQLKSGTASVVCLLNNFYPREAKVQWKVD
9.8A       Y-PLTFGGGTKVEIKR-TVAAPSVFIFPPSDEQLKSGTASVVCLLNNFYPREAKVQWKVD
18.5C      SPLWAFGQGTKVEIKR-TVAAPSVFIFPPSDEQLKSGTASVVCLLNNFYPREAKVQWKVD
8.11G      W-PRTFGQGTKLEIKR-TVAAPSVFIFPPSDEQLKSGTASVVCLLNNFYPREAKVQWKVD
25.10C     ---RTFGRGTKLDVKR-TVAAPSVFIFPPSDEQLKSGTASVVCLLNNFYPREAKVQWKVD
                :* **:   :     *  *:* :****.*:*::..*::***:.:***   ..* **.*
```

FIG. 8

```
10.4B     NALQSGNSQESVTEQDSKDSTYSLSSTLTLSKADYEKHKVYACEVTHQGLSSP-------
19.7E     NALQSGNSQESVTEQDSKDSTYSLSSTLTLSKADYEKHKVYACEVTHQGLSSPVTKSFNR
2.9D      NALQSGNSQESVTEQDSKDSTYSLSSTLTLSKADYEKHKVYACEVTHQGLSSPVTKSFNR
25.6A     SSPVKAGV-ETTTPSKQSNNKYAASSYLSLTPEQWKSHRSYSCQVTHEGST--VEKTVAP
36.1F     NALQSGNSQESVTEQDSKDSTYSLSSTLTLSKADYEKHKVYACEVTHQGLSSPVTKSFNR
36.9F     NALQSGNSQESVTEQDSKDSTYSLSSTLTLSKADYEKHKVYACEVTHQGLSSPVTKSFNR
37.2D     NALQSGNSQESVTEQDSKDSTYSLSSTLTLSKADYEKHKVYACEVTHQGLSSPVTKSFNR
37.2G     NALQSGNSQESVTEQDSKDSTYSLSSTLTLSKADYEKHKVYACEVTHQGLSSPVTKSFNR
37.7H     SSPVKAGV-ETTTPSKQSNNKYAASSYLSLTPEQWESHRSYSCQVTHEGST--VEKTVAP
8.9F      SSPVKAGV-ETTTPSKQSNNKYAASSYLSLTPEQWKSHRSYSCQVTHEGST--VEKTVAP
NE13      NALQSGNSQESVTEQDSKDSTYSLSSTLTLSKADYEKHKVYACEVTHQGLSSPVTKSFNR
12.1F     NALQSGNSQESVTEQDSKDSTYSLSSTLTLSKADYEKHKVYACEVTHQGLSSPVTKSFNR
9.8A      NALQSGNSQESVTEQDSKDSTYSLSSTLTLSKADYEKHKVYACEVTHQGLSSPVTKSFNR
18.5C     NALQSGNSQESVTEQDSKDSTYSLSSTLTLSKADYEKHKVYACEVTHQGLSSPVTKSFNR
8.11G     NALQSGNSQESVTEQDSKDSTYSLSSTLTLSKADYEKHKVYACEVTHQGLSSPVTKSFNR
25.10C    NALQSGNSQESVTEQDSKDSTYSLSSTLTLSKADYEKHKVYACEVTHQGLSSPVTKSFNR
          .:  ...  *:.* ....:..*: ** *:*:  :::.*: *:*:***:* :

10.4B     ------------------------------------------------------------
19.7E     GEC---------------------------------------------------------
2.9D      GEC---------------------------------------------------------
25.6A     TECS*-------------------------------------------------------
36.1F     GEC*--------------------------------------------------------
36.9F     GEC*--------------------------------------------------------
37.2D     GEC*--------------------------------------------------------
37.2G     GEC*--------------------------------------------------------
37.7H     TECS*-------------------------------------------------------
8.9F      TECS*-------------------------------------------------------
NE13      GEC*--------------------------------------------------------
12.1F     GEC*--------------------------------------------------------
9.8A      GEC*--------------------------------------------------------
18.5C     GEC*--------------------------------------------------------
8.11G     GEC*--------------------------------------------------------
25.10C    GEVLGGRKLGRHGPTCLLQLIMVTNKAIASQISQIKHFFHCILVVVCPNSSMYLIMSGSG
```

FIG. 8 Cont.

ARENA VIRUS MONOCLONAL ANTIBODIES AND USES

CROSS REFERENCE TO RELATED APPLICATIONS

This application is a divisional of U.S. application Ser. No. 17/520,338, filed on Nov. 5, 2021, which is a divisional of U.S. application Ser. No. 16/466,544, filed on Jun. 4, 2019, now U.S. Pat. No. 11,198,723, which is a 371 of International Application No. PCT/US2017/064744, filed on Dec. 5, 2017, which claims the benefit of U.S. Provisional Application Ser. No. 62/430,225, filed on Dec. 5, 2016, each of which is incorporated herein by reference in its entirety.

STATEMENT REGARDING FEDERALLY SPONSORED RESEARCH OR DEVELOPMENT

This invention was made, in part, with support provided by the United States government under Grant Nos. U19 AI109762, 1 R01 AI104621, R43 AI120472, and NIAID Project No. 272200900049C-0-0-1 from the National Institutes of Health. The government has certain rights in this invention.

FIELD OF THE INVENTION

The present invention relates to novel arenavirus monoclonal antibodies, to compositions comprising the arenavirus monoclonal antibodies, and methods comprising the same.

INCORPORATION OF SEQUENCE LISTING

Biological sequence information for this application is included in a XML file having the file name "TU-439 Div2.xml", created on Dec. 19, 2023, and having a file size of 186,909 bytes, which is incorporated herein by reference.

BACKGROUND

Lassa virus (LASV) and several other members of the Arenaviridae are classified as Biosafety Level 4 and NIAID Biodefense Category A agents. The present invention will fill a vital biodefense need for rapid multiagent immunodiagnostic assays for arenaviruses and for effective therapeutics against arenaviral disease, and will provide a major advance for public health management of an important family of viral pathogens. Several arenaviruses, chiefly Lassa virus (LASV) in West Africa, cause hemorrhagic fever (HF) disease in humans and pose serious public health concerns in their endemic regions. The global endemicity of the prototypic arenavirus lymphocytic choriomeningitis virus (LCMV) is not a causative agent of HF, but mounting evidence indicates that LCMV is a neglected human pathogen of clinical significance that can cause neurologic disease in the fetus, child and adult stages. In addition, LCMV poses a special threat in immune-compromised individuals, as tragically illustrated by recent cases of transplant-associated infections by LCMV with a fatal outcome in the United States and Australia. Moreover, the high seroprevalence of LCMV within different urban populations across the world, including the US, has raised the question of whether LCMV may contribute to the many cases of undiagnosed aseptic meningitis reported yearly.

Lassa fever. The most prevalent arenaviral disease is Lassa fever (LF), an often-fatal hemorrhagic fever named for the Nigerian town in which the first described cases occurred in 1969 (Buckley and Casals, 1970). Parts of Guinea, Sierra Leone, Nigeria, and Liberia are endemic for the etiologic agent, LASV (Birmingham and Kenyon, 2001). Although detailed surveillance of LASV is hampered by many factors, including the lack of a widely available diagnostic test, it is clear that the public health impact is immense. There are as many as 300,000 cases of Lassa per year in West Africa and 5,000 deaths (see the CDC website at www(dot)cdc(dot)gov/ncidod/dvrd/spb/mnpages/dispages/lassaf(dot)htm). In some parts of Sierra Leone, 10-16% of all patients admitted to hospitals have Lassa fever. Case fatality rates for Lassa fever have typically been reported as 15% to 20%, and as high as 45% during epidemics, with a recent multi-year study in Sierra Leone reporting a 69% rate (Schaffer et al., 2014). LASV has been associated with severe nosocomial outbreaks involving health care workers and laboratory personnel (Fisher-Hoch et al., 1995). The mortality rate for women in the last month of pregnancy is always high, about 90%, and LASV infection causes high rates of fetal death at all stages of gestation (Walls, 1985). Mortality rates for Lassa appear to be higher in non-Africans, which is of concern because Lassa is the most commonly exported hemorrhagic fever (Haas et al., 2003; Holmes et al., 1990).

Old and New World arenaviruses. Arenaviruses are enveloped viruses with a bi-segmented negative strand (NS) RNA genome. Each genomic RNA segment, L (ca. 7.3 kb) and S (ca. 3.5 kb), uses an ambisense coding strategy to direct the synthesis of two polypeptides in opposite orientation, separated by a non-coding intergenic region. The S RNA encodes the viral glycoprotein precursor (GPC) and the nucleoprotein (NP). GPC is co- and post-translationally processed to yield the two mature virion surface glycoproteins GP1 and GP2 that together with the stable signal peptide (SSP) form the GP complex that decorates the virus surface and directs virus cell entry via receptor-mediated endocytosis. The L RNA encodes the viral RNA dependent RNA polymerase (L polymerase), and the small RING finger protein Z that has functions of a bona fide matrix protein. The structure of arenavirus GP2 appears to be a class I fusion protein, which is common to envelope glycoproteins of myxoviruses, retroviruses and filoviruses (Gallaher, DiSimone, and Buchmeier, 2001). When viewed by transmission electron microscopy, the enveloped spherical virions (diameter: 110-130 nm) show grainy particles that are ribosomes acquired from the host cells (Murphy and Whitfield, 1975), hence the basis for the family name of the Latin word "arena," which means "sandy." The arenaviruses are divided into the Old World or lymphocytic choriomeningitis virus (LCMV)/LASV complex and the New World or Tacaribe complex (Bowen, Peters, and Nichol, 1997). There is considerable diversity amongst members of the Arenaviridae (FIG. 1), and even within the same virus species (Bowen et al., 2000). In addition to LASV, other arenaviruses that cause severe illness in humans and are classified as BSL-4 and NIAID category A agents include the New World arenaviruses Machupo virus (MACV, Bolivian hemorrhagic fever), Junin virus (JUNV, Argentine hemorrhagic fever), Guanarito virus (GUAV, Venezuelan hemorrhagic fever) and Sabia virus (SABV, Brazilian hemorrhagic fever). Arenaviruses are zoonotic; each virus is associated with a specific species of rodent (Bowen, Peters, and Nichol, 1997). The LCMV/LASV complex viruses are associated with Old World rats and mice (family Muridae, subfamily Murinae). Tacaribe complex viruses are generally associated with New World rats and mice (family Muridae, subfamily Sigmodontinae); however, the reservoir of Tacaribe virus itself appears to be a bat (Bowen, Peters, and Nichol, 1996). The reservoir of LASV is the "multimammate rat" of the genus *Mastomys* (Monath et al., 1974). *Mastomys* rats are ubiquitous in sub-Saharan Africa (Demby et al., 2001) and are known to be peridomestic, often living in human homes; however, many questions regarding the taxonomy, geographic distribution and ecobiology of *Mastomys* species are unanswered. As with the natural hosts of other arenaviruses, *Mastomys* show no symptoms of LASV infection, but shed the virus in saliva, urine and feces. Eradication of the widely distributed rodent reservoirs of LASV and other arenaviruses is impractical and ecologically undesirable.

Arenaviruses cause chronic infections of rodents across the world with human infections mostly occurring through mucosal exposure or by direct contact of abraded skin with infectious materials. Arenaviruses are easily transmitted to humans from rodents via direct contact with rodent excreta or by contact with or ingestion of excreta-contaminated materials (Bausch et al., 2001; Demby et al., 2001). In the case of *Mastomys* species, infection may also occur when the animals are caught, prepared as a food source and eaten. Most arenaviruses, including LASV, are readily transmitted between humans, thus making nosocomial infection another matter of great concern. Human-to-human transmission can occur via exposure to blood or body fluids. LASV can also be transmitted to sexual partners of convalescent men via semen up to six weeks post-infection.

Natural history of Lassa fever. Signs and symptoms of Lassa fever, which occur 1-3 weeks after virus exposure, are highly variable, but typically begin with the insidious onset of fever and other nonspecific symptoms such as headache, generalized weakness, and malaise, followed within days by sore throat, retrosternal pain, conjunctival injection, abdominal pain, and diarrhea. LASV infects endothelial cells, resulting in increased capillary permeability, which can produce diminished effective circulating volume (Peters et al., 1989). Severe cases progress to facial and neck swelling, shock and multiorgan system failure. Frank bleeding, usually mucosal (gums, etc.), occurs in less than a third of cases, but confers a poor prognosis. Neurological problems have also been described, including hearing loss, tremors, and encephalitis. Patients who survive begin to defervesce 2-3 weeks after onset of the disease. Temporary or permanent unilateral or bilateral deafness that occurs in a third of Lassa patients during convalescence is not associated with the severity of the acute disease (Cummins et al., 1990; Rybak, 1990; Hartnet et al., 2015; Anderson et al., 2015; Branco et al., October 2011; Grove et al., 2011; Branco et al., 2010; Branco et al., August 2011).

Potential for use of arenaviruses as bioweapons. In addition to high case fatality rates, arenaviruses have many features that enhance their potential as bioweapons. Arenaviruses have relatively stable virions, do not require passage via insect vectors, are spread easily by human-to-human contact, and may be capable of aerosol spread or other simple means of dispersal. The high prevalence of Lassa fever in western Africa coupled with the ease of travel to and from this area and endemic areas for MACV, JUNV, GUAV, SABV and other highly pathogenic arenaviruses permits easy access to these viruses for use as a bioweapon. A cluster of hemorrhagic fever cases in the United States caused by any arenavirus would be a major public health incident. Because febrile illnesses are common, and the use of reliable arenavirus diagnostic tests is not commonplace, an initial cluster of undiagnosed cases would greatly increase the impact of the attack and permit wider dissemination via human-to-human contact. The potential use of LASV and other arenaviruses as a biological weapon directed against civilian or military targets potentiated the commercial development of effective diagnostics, which the VHFC has accomplished, through the marketing of immunodiagnostic tests for the rapid detection of LASV infections (ReLASV Rapid Diagnotic Test [RDT]™, RePanLASV RDT™) and companion ELISA diagnostics for the detection of antigenemia and the immunoglobulin (Ig) M (IgM) and G (IgG) response to infection (www(dot)zalgenlabs(dot)com/products).

Treatment/prevention of arenavirus infections. There are no Food and Drug Administration (FDA)-approved arenavirus vaccines and current anti-arenaviral therapy is limited to an off-label use of the antiviral drug ribavirin that is only partially effective and can cause significant side effects. Ribavirin may be effective in the treatment of Lassa fever only if administered early in the course of illness (Johnson et al., 1987; McCormick et al., 1986). Ribavirin administered to patients with a high virus load (and therefore a high risk for mortality) within the first six days of illness reduced the case-fatality rate from 55% to 5% (McCormick et al., 1986). Several anecdotal reports suggest that this drug can also be effective against other arenaviral hemorrhagic fevers (Barry et al., 1995; Kilgore et al., 1997; Weissenbacher et al., 1986a; Weissenbacher et al., 1986b). The efficacy of prophylactic treatments for Lassa fever is unknown, although it has been suggested that people with high-risk exposures be treated with oral ribavirin. Control of LCMV infection is mediated mainly by cellular immune responses, and significant titers of neutralizing antibodies to LCMV appear usually only after the patients have clinically recovered. However, passive antibody transfer has been shown to confer protection in animal models of LCMV infection (Enria et al., 1984; Frame et al., 1984; Jahrling, 1983; Jahrling and Peters, 1984; Jahrling, Peters, and Stephen, 1984; Weissenbacher et al., 1986a). Thus, antibody-based therapy may provide a safer alternative for treatment of LCMV based on predetermined correlates of protection. Previous studies of passive transfer of serum to treat Argentine hemorrhagic fever (AHF) and Lassa fever provide a strong rationale for the methods disclosed herein. Although passive transfer of serum has proven effective against the New and Old World virus, this approach is not scalable to protect large populations in the case of a hypothetical release of these viruses. Another issue is the safety of transfused serum or plasma, in particular those living in regions where circulating unknown pathogens are of concern. Recombinant, neutralizing, human antibodies have never been tested as potential therapeutics in arenavirus-induced HFs, but these limitations can be overcome. No arenavirus vaccine is currently available, although vaccines against LASV and JUNV are in development. Effective diagnostic assays are absolutely essential for development and field testing arenaviral vaccines.

Antibody-based therapy to combat human viral infections. Viral antigenic variability can pose significant obstacles to the development of effective vaccines to combat human viral infections as illustrated in the cases of HIV and influenza virus. Notably, recent findings have shown that some infected individuals generate broadly neutralizing monoclonal antibodies (BNhMAbs) that target a conserved domain within the stem region of the viral surface envelope (Env) glycoprotein of HIV-1 or and are able to block infection by many phylogenetically distinct isolates. Likewise, a number of BNhMAbs have been shown to target a conserved domain within the proximal membrane stalk domain of influenza virus hemagglutinin (HA) and several BNhMAbs such as MAb F16 and MAb 5A7 proved to be protective when passively administered in mouse models of influenza virus infection. Antibodies typically exhibit desirable pharmacological characteristics including long serum half-lives, high potency, and limited off-target toxicity. Hence, the recent developments in the area of BNhMAbs have raised great interest in exploring their development as viable antiviral therapy. In addition, because BNhMAbs often recognize conserved epitopes within the region of the viral glycoproteins that mediate fusion between viral and cellular membranes, they can also facilitate the identification and structural characterization of highly conserved viral epitopes, knowledge that can be harnessed for the generation of universal vaccines and broad-spectrum antiviral drugs against these viral pathogens. As with HIV-1 and influenza, arenavirus cell entry requires a pH-dependent fusion event that is mediated by the fusogenic domain of GP2. The identification and characterization of LCMV GP-specific BNhMAbs will facilitate the development of a novel antibody-based therapy to treat LASV and LCMV induced disease in humans. In addition, this work may generate valuable information for the design of immunogens to facilitate the development of universal arenavirus vaccines, as well as broad-spectrum anti-arenaviral drugs targeting the conserved structural and functional motifs identified by BNhMAbs.

Need for the invention. The work described herein combines the use of state-of-the-art arenavirus reverse genetics with the access to a unique collection of LASV GP-specific human monoclonal antibodies (hMAbs) that have been shown to cross-react and neutralize different strains of LCMV, including isolates from human cases of LASV and LCMV induced disease, as well as WE strain that causes a LF-like disease in non-human primates. The present disclosure provides an antibody-based therapy to treat human cases of LCMV-induced disease. Unlike vaccines that depend on the host's ability to mount an effective immune response, this novel approach can provide protection in immunosuppressed individuals, including cases of LASV and LCMV infection associated with severe clinical symptoms in individuals undergoing transplantation procedures. Moreover, a detailed characterization of the conserved epitopes within LCMV GPC recognized by these BNhMAbs may help to design immunogens aimed at developing a vaccine able to confer protection against all LASV and LCMV strains that have been linked to disease in humans. In addition, information obtained from the identification and characterization of LASV BNhMAbs will help to identify broad-spectrum anti-LASV and LCMV drugs via targeting conserved epitopes identified by these BNhMAbs. The experimental approach described herein involves the use of unique reagents and assays to identify and characterize LASV and LCMV BNhMAbs and their targets.

There is an ongoing need to address LASV and LCMV infections from natural sources, as well as weaponized versions of these viruses. There also is a need for neutralizing antibodies to LASV and LCMV for diagnostic and analytical uses. The materials (e.g., antibodies and fragments thereof) and methods described herein address these needs.

SUMMARY

A single-cycle infectious, GFP-expressing, rLCMV has been generated in which the GP is replaced by GFP (rLCMVΔGP/GFP). Genetic complementation with plasmids or stable cell lines expressing arenavirus GPs of interest results in production of the corresponding GP-pseudotyped rLCMVΔGP/GFP that are used to evaluate neutralizing antibody responses to different LCMV strains using a novel GFP-based microneutralization assay. A tri-segmented LCMV platform has been developed within the backbone of ARM or Cl-13 LCMV strains that allows expression of an arenavirus GP of choice and an appropriate reporter gene (e.g. fluorescent and luciferase proteins) together for facile identification of LCMV BNhMAbs and monitoring the emergence of BNhMAb LCMV escape mutants. Reverse genetics approaches have been developed that allow generation of rLCM viruses within the backbone of the immunosuppressive Cl-13 LCMV strain expressing GPs of interest that can be used to characterize the therapeutic value in vivo of these BNhMAbs. Highly specific anti-idiotypic antibodies were generated to individually detect and characterize the PK, concentration, and clearance from the circulation of each MAb used in combination therapy to enhance neutralization potency while minimizing the emergence of escape mutants. A panel of anti-idiotype antibodies (anti-ids) to 37.2D specifically detected this BNhMAb when spiked into human serum and did not capture or detect any other arenaviral BNhMAb tested to date, or any other IgG specificity present in human serum on both ELISA and SPR based studies.

Disclosed herein are compositions comprising arenavirus monoclonal antibodies (e.g., fully human monoclonal antibodies), as well as therapeutic, diagnostic, and preventative methods using the antibodies. Preventative methods include preparation of vaccines, as well as factors (e.g. small molecules, peptides) that inhibit Old World arenavirus infectivity, including LASV and LCMV. Diagnostic and therapeutic antibodies including neutralizing antibodies for the prevention and treatment of infection by LASV and other arenaviruses are also disclosed, as well as new tools and methods for the design, production, and use of arenavirus monoclonal antibodies, including expression in engineered bacterial- and mammalian-based systems.

One embodiment of the materials and methods described herein relates to monoclonal antibodies and fragments thereof effective against LASV.

Another embodiment of the materials and methods described herein relates to monoclonal antibodies or fragments thereof effective against LCMV.

Another embodiment of the materials and methods described herein relates to methods of producing forms of monoclonal antibodies effective against LASV and/or LCMV.

Another embodiment of the materials and methods described herein relates to expression vectors comprising polynucleotides encoding forms of the LASV or LCMV GP-specific hMAbs.

An embodiment of the materials and methods described herein relates to diagnostic uses of antibodies or fragments thereof, such as neutralizing antibodies, specific for LASV or LCMV.

Another embodiment of the materials and methods described herein relates to diagnostics comprising the antibodies or fragments thereof specific for LASV or LCMV, including labeled antibodies or fragments thereof of the invention.

Another embodiment of the materials and methods described herein is directed to kits comprising the antibodies of the invention.

The following non-limiting embodiments are provided to illustrate certain aspects and feature of the materials and methods described herein.

Embodiment 1 is an antigen-binding composition comprising a neutralizing antibody or neutralizing antigen-binding antibody fragment thereof specific to glycoprotein 1 (GP1), glycoprotein 2 (GP2), glycoprotein precursor (GPC), or full-length glycoprotein (GP) of Lassa virus (LASV), wherein the antibody or antibody fragment comprises a heavy chain variable region ($V_H$) and a light chain variable region ($V_L$), the $V_H$ and $V_L$ each comprising complementarity determining regions CDR1, CDR2 and CDR3 selected from the group consisting of:

(a) a $V_H$ CDR1 of SEQ ID NO: 65, a $V_H$ CDR2 of SEQ ID NO: 66, a $V_H$ CDR3 of SEQ ID NO: 67, a $V_L$ CDR1 of SEQ ID NO: 113, a $V_L$ CDR2 of sequence Gly Ala Ser, and a $V_L$ CDR3 of SEQ ID NO: 114 (from MAb 10.4B);

(b) a $V_H$ CDR1 of SEQ ID NO: 68, a $V_H$ CDR2 of SEQ ID NO: 69, a $V_H$ CDR3 of SEQ ID NO: 70, a $V_L$ CDR1 of SEQ ID NO: 115, a $V_L$ CDR2 of sequence Lys Ala Ser, and a $V_L$ CDR3 of SEQ ID NO: 116 (from MAb 19.7E);

(c) a $V_H$ CDR1 of SEQ ID NO: 71, a $V_H$ CDR2 of SEQ ID NO: 72, a $V_H$ CDR3 of SEQ ID NO: 73, a $V_L$ CDR1 of SEQ ID NO: 117, a $V_L$ CDR2 of sequence Trp Ala Ser, and a $V_L$ CDR3 of SEQ ID NO: 118 (from MAb 2.9D);

(d) a $V_H$ CDR1 of SEQ ID NO: 74, a $V_H$ CDR2 of SEQ ID NO: 75, a $V_H$ CDR3 of SEQ ID NO: 76, a $V_L$ CDR1 of SEQ ID NO: 119, a $V_L$ CDR2 of sequence Glu Val Lys, and a $V_L$ CDR3 of SEQ ID NO: 120 (from MAb 25.6A);

(e) a $V_H$ CDR1 of SEQ ID NO: 77, a $V_H$ CDR2 of SEQ ID NO: 78, a $V_H$ CDR3 of SEQ ID NO: 79, a $V_L$ CDR1 of SEQ ID NO: 121, a $V_L$ CDR2 of sequence Asp Ala Ser, and a $V_L$ CDR3 of SEQ ID NO: 122 (from MAb 36.1F);

(f) a $V_H$ CDR1 of SEQ ID NO: 80, a $V_H$ CDR2 of SEQ ID NO: 81, a $V_H$ CDR3 of SEQ ID NO: 82, a $V_L$ CDR1 of SEQ ID NO: 123, a $V_L$ CDR2 of sequence Gly Ala Ser, and a $V_L$ CDR3 of SEQ ID NO: 124 (from MAb 36.9F);

(g) a $V_H$ CDR1 of SEQ ID NO: 83, a $V_H$ CDR2 of SEQ ID NO: 84, a $V_H$ CDR3 of SEQ ID NO: 85, a $V_L$ CDR1 of SEQ ID NO: 125, a $V_L$ CDR2 of sequence Gly Ala Ser, and a $V_L$ CDR3 of SEQ ID NO: 126 (from MAb 37.2D);

(h) a $V_H$ CDR1 of SEQ ID NO: 86, a $V_H$ CDR2 of SEQ ID NO: 87, a $V_H$ CDR3 of SEQ ID NO: 88, a $V_L$ CDR1 of SEQ ID NO: 127, a $V_L$ CDR2 of sequence Gly Ala Ser, and a $V_L$ CDR3 of SEQ ID NO: 128 (from MAb 37.2G);

(i) a $V_H$ CDR1 of SEQ ID NO: 89, a $V_H$ CDR2 of SEQ ID NO: 90, a $V_H$ CDR3 of SEQ ID NO: 91, a $V_L$ CDR1 of SEQ ID NO: 129, a $V_L$ CDR2 of sequence Glu Val Arg, and a $V_L$ CDR3 of SEQ ID NO: 130 (from MAb 37.7H);

(j) a $V_H$ CDR1 of SEQ ID NO: 92, a $V_H$ CDR2 of SEQ ID NO: 93, a $V_H$ CDR3 of SEQ ID NO: 94, a $V_L$ CDR1 of SEQ ID NO: 131, a $V_L$ CDR2 of sequence Glu Val Ser, and a $V_L$ CDR3 of SEQ ID NO: 132 (from MAb 8.9F);

(k) a $V_H$ CDR1 of SEQ ID NO: 95, a $V_H$ CDR2 of SEQ ID NO: 96, a $V_H$ CDR3 of SEQ ID NO: 97, a $V_L$ CDR1 of SEQ ID NO: 133, a $V_L$ CDR2 of sequence Gly Ala Ser, and a $V_L$ CDR3 of SEQ ID NO: 134 (from MAb NE13);

(l) a $V_H$ CDR1 of SEQ ID NO: 98, a $V_H$ CDR2 of SEQ ID NO: 99, a $V_H$ CDR3 of SEQ ID NO: 100, a $V_L$ CDR1 of SEQ ID NO: 135, a $V_L$ CDR2 of sequence Gly Ala Ser, and a $V_L$ CDR3 of SEQ ID NO: 136 (from MAb 12.1F);

(m) a $V_H$ CDR1 of SEQ ID NO: 101, a $V_H$ CDR2 of SEQ ID NO: 102, a $V_H$ CDR3 of SEQ ID NO: 103, a $V_L$ CDR1 of SEQ ID NO: 137, a $V_L$ CDR2 of sequence Gln Ala Ser, and a $V_L$ CDR3 of SEQ ID NO: 138 (from MAb 9.8A);

(n) a $V_H$ CDR1 of SEQ ID NO: 104, a $V_H$ CDR2 of SEQ ID NO: 105, a $V_H$ CDR3 of SEQ ID NO: 106, a $V_L$ CDR1 of SEQ ID NO: 139, a $V_L$ CDR2 of sequence Gly Ala Ser, and a $V_L$ CDR3 of SEQ ID NO: 140 (from MAb 18.5C);

(o) a $V_H$ CDR1 of SEQ ID NO: 107, a $V_H$ CDR2 of SEQ ID NO: 108, a $V_H$ CDR3 of SEQ ID NO: 109, a $V_L$ CDR1 of SEQ ID NO: 141, a $V_L$ CDR2 of sequence Gly Ala Tyr, and a $V_L$ CDR3 of SEQ ID NO: 142 (from MAb 8.11 G); and (p) a $V_H$ CDR1 of SEQ ID NO: 110, a $V_H$ CDR2 of SEQ ID NO: 111, a $V_H$ CDR3 of SEQ ID NO: 112, a $V_L$ CDR1 of SEQ ID NO: 143, a $V_L$ CDR2 of sequence Ala Ala Val, and a $V_L$ CDR3 of SEQ ID NO: 144 (from MAb 25.10C).

Embodiment 2 is the composition of Embodiment 1, wherein the composition comprises two or more of said antibodies or antigen-binding antibody fragments.

Embodiment 3 is the composition of any one of Embodiments 1 and 2, wherein the composition comprises:

(1) an antibody or antigen-binding antibody fragment comprising a $V_H$ CDR1 of SEQ ID NO: 83, a $V_H$ CDR2 of SEQ ID NO: 84, a $V_H$ CDR3 of SEQ ID NO: 85, a $V_L$ CDR1 of SEQ ID NO: 125, a $V_L$ CDR2 of sequence Gly Ala Ser, and a $V_L$ CDR3 of SEQ ID NO: 126 (from MAb 37.2D);

(2) an antibody or antigen-binding antibody fragment comprising a $V_H$ CDR1 of SEQ ID NO: 92, a $V_H$ CDR2 of SEQ ID NO: 93, a $V_H$ CDR3 of SEQ ID NO: 94, a $V_L$ CDR1 of SEQ ID NO: 131, a $V_L$ CDR2 of sequence Glu Val Ser, and a $V_L$ CDR3 of SEQ ID NO: 132 (from MAb 8.9F); and (3) an antibody or antigen-binding antibody fragment comprising a $V_H$ CDR1 of SEQ ID NO: 98, a $V_H$ CDR2 of SEQ ID NO: 99, a $V_H$ CDR3 of SEQ ID NO: 100, a $V_L$ CDR1 of SEQ ID NO: 135, a $V_L$ CDR2 of sequence Gly Ala Ser, and a $V_L$ CDR3 of SEQ ID NO: 136 (from MAb 12.1F).

Embodiment 4 is the composition of any one of Embodiments 1 to 3, wherein the antibody is selected from the group consisting of a monoclonal antibody, and a recombinantly produced antibody.

Embodiment 5 is the composition of any one of Embodiments 1 to 4, wherein the antibody comprises a human monoclonal antibody.

Embodiment 6 is the composition of any one of Embodiments 1 to 3, wherein the antigen-binding antibody fragment is selected from the group consisting of a Fab, a Fab', and a $F(ab')_2$ fragment.

Embodiment 7 is a nucleic acid (e.g., a cDNA) having a sequence that encodes for a $V_H$ of the antibody or the antibody fragment of a composition of Embodiment 1.

Embodiment 8 is the nucleic acid of Embodiment 7, wherein the nucleic acid includes a nucleic acid sequence selected from the group consisting of SEQ ID NO: 1 through SEQ ID NO: 16.

Embodiment 9 is a nucleic acid 9e.g., a cDNA) having a sequence that encodes for a $V_L$ of the antibody or the antibody fragment of Embodiment 1.

Embodiment 10 is the nucleic acid of Embodiment 9, wherein the nucleic acid includes a nucleic acid sequence selected from the group consisting of SEQ ID NO: 17 through SEQ ID NO: 32.

Embodiment 11 is an expression vector that contains the nucleic acid sequence of any one of Embodiments 7 to 10.

Embodiment 12 is an antigen-binding composition comprising a neutralizing antibody or neutralizing antigen-binding antibody fragment thereof specific to glycoprotein 1 (GP1), glycoprotein 2 (GP2), glycoprotein precursor (GPC), or full-length glycoprotein (GP) of Lassa virus (LASV), wherein the antibody or antibody fragment comprises a heavy chain variable region ($V_H$) and a light chain variable region ($V_L$) selected from the group consisting of:

(a) a $V_H$ of SEQ ID NO: 33 and a $V_L$ of SEQ ID NO: 49 (from MAb 10.4B);

(b) a $V_H$ of SEQ ID NO: 34 and a $V_L$ of SEQ ID NO: 50 (from MAb 19.7E);

(c) a $V_H$ of SEQ ID NO: 35 and a $V_L$ of SEQ ID NO: 51 (from MAb 2.9D);

(d) a $V_H$ of SEQ ID NO: 36 and a $V_L$ of SEQ ID NO: 52 (from MAb 25.6A);

(e) a $V_H$ of SEQ ID NO: 37 and a $V_L$ of SEQ ID NO: 53 (from MAb 36.1F);

(f) a $V_H$ of SEQ ID NO: 38 and a $V_L$ of SEQ ID NO: 54 (from MAb 36.9F);

(g) a $V_H$ of SEQ ID NO: 39 and a $V_L$ of SEQ ID NO: 55 (from MAb 37.2D);

(h) a $V_H$ of SEQ ID NO: 40 and a $V_L$ of SEQ ID NO: 56 (from MAb 37.2G);

(i) a $V_H$ of SEQ ID NO: 41 and a $V_L$ of SEQ ID NO: 57 (from MAb 37.7F);

(j) a $V_H$ of SEQ ID NO: 42 and a $V_L$ of SEQ ID NO: 58 (from MAb 8.9F);

(k) a $V_H$ of SEQ ID NO: 43 and a $V_L$ of SEQ ID NO: 59 (from MAb NE13);

(l) a $V_H$ of SEQ ID NO: 44 and a $V_L$ of SEQ ID NO: 60 (from MAb 12.1F);

(m) a $V_H$ of SEQ ID NO: 45 and a $V_L$ of SEQ ID NO: 61 (from MAb 9.8A);

(n) a $V_H$ of SEQ ID NO: 46 and a $V_L$ of SEQ ID NO: 62 (from MAb 18.5C);

(o) a $V_H$ of SEQ ID NO: 47 and a $V_L$ of SEQ ID NO: 63 (from MAb 8.11G); and (p) a $V_H$ of SEQ ID NO: 48 and a $V_L$ of SEQ ID NO: 64 (from MAb 25.10C).

Embodiment 13 is the composition of Embodiment 12, wherein the composition comprises two or more of said antibodies or antigen-binding antibody fragments.

Embodiment 14 is the composition of any one of Embodiments 12 and 13, wherein the composition comprises:

(1) an antibody or antigen-binding antibody fragment comprising a $V_H$ of SEQ ID NO: 39 and a $V_L$ of SEQ ID NO: 55 (from MAb 37.2D);

(2) an antibody or antigen-binding antibody fragment comprising a $V_H$ of SEQ ID NO: 42 and a $V_L$ of SEQ ID NO: 58 (from MAb 8.9F); and (3) an antibody or antigen-binding antibody fragment comprising a $V_H$ of SEQ ID NO: 44 and a $V_L$ of SEQ ID NO: 60 (from MAb 12.1F).

Embodiment 15 is the composition of any one of Embodiments 12 to 14, wherein the the antibody is selected from the group consisting of a monoclonal antibody, and a recombinantly produced antibody.

Embodiment 16 is the composition of any one of Embodiments 12 to 15, wherein the antibody comprises a human monoclonal antibody.

Embodiment 17 is the composition of any one of Embodiments 12 to 14, wherein the antigen-binding antibody fragment is selected from the group consisting of a Fab, a Fab', and a $F(ab')_2$ fragment.

Embodiment 18 is a nucleic acid (e.g., a cDNA) having a sequence that encodes for a $V_H$ of the antibody or the antibody fragment of Embodiment 12.

Embodiment 19 is a nucleic acid (e.g., a cDNA) having a sequence that encodes for a $V_L$ of the antibody or the antibody fragment of Embodiment 12.

Embodiment 20 is an expression vector that contains the nucleic acid sequence of any one of Embodiments 18 to 19.

Embodiment 21 is a vaccine for preventing or treating infection of a patient by Lassa virus or other arenaviridae comprising the antibody or antibody fragment of any one of Embodiments 1 to 6 and 12 to 17.

Embodiment 22 is the vaccine of Embodiment 21, which is cross-protective against infection by other arenaviridae.

Embodiment 23 is the vaccine of any one of Embodiments 21 to 22, which is cross-protective against infection by a lymphocytic choriomeningitis virus.

Embodiment 24 is a pharmaceutical composition for treating or preventing infection by a Lassa virus or other arenaviridae comprising the antibody or antibody fragment of any one of Embodiments 1 to 6 and 12 to 17 and a pharmaceutically acceptable carrier.

Embodiment 25 is the antibody or antibody fragment of any one of Embodiments 1 to 6 and 12 to 17 for use in treating or preventing infection by a Lassa virus or other arenaviridae.

Embodiment 26 is the antibody or antibody fragment of any one of Embodiments 1 to 6 and 12 to 17 for use in treating or preventing a lymphocytic choriomeningitis virus infection.

Embodiment 27 is use of the antibody or antibody fragment of any one of Embodiments 1 to 6 and 12 to 17 for treating or preventing infection by a Lassa virus or other arenaviridae.

Embodiment 28 is use of the antibody or antibody fragment of any one of Embodiments 1 to 6 and 12 to 17 for treating or preventing a lymphocytic choriomeningitis virus infection.

Embodiment 29 is use of the antibody or antibody fragment of any one of Embodiments 1 to 6 and 12 to 17 for the preparation of a medicament for treating or preventing infection by a Lassa virus or other arenaviridae.

Embodiment 30 is use of the antibody or antibody fragment of any one of Embodiments 1 to 6 and 12 to 17 for the preparation of a medicament for treating or preventing a lymphocytic choriomeningitis virus infection.

Embodiment 31 is diagnostic kit for detecting infection of a subject by Lassa virus or other arenaviridae comprising at least one antibody or antibody fragment of any one of Embodiments 1 to 6 and 12 to 17 bound to a detectable labelling group.

Embodiment 32 is an antibody or antibody fragment of any one of Embodiments 1 to 6 and 12 to 17 bound to a detectable labelling group.

Embodiment 33 is a method of detecting infection by a Lassa virus or other arenaviridae comprising contacting a biological sample from a subject with at least one antibody or antibody fragment of any one of Embodiments 1 to 6 and 12 to 17 bound to a detectable labelling group; and detecting a complex between the antibody or antibody fragment and a Lassa virus or other arenaviridae present in the sample.

Embodiment 34 is a method of treating or preventing infection by a Lassa virus or other arenaviridae in a subject comprising administering the antibody or antibody fragment of any one of Embodiments 1 to 6 and 12 to 17 to the subject.

Embodiment 35 is a method of treating or preventing a lymphocytic choriomeningitis virus infection in a subject comprising administering the antibody or antibody fragment of any one of Embodiments 1 to 6 and 12 to 17 to the subject.

Other embodiments and advantages of the materials and methods described herein are set forth in part in the description, which follows, and in part, may be understood by a person of ordinary skill in the art from this description, or from the practice or use of the materials and methods described herein.

DESCRIPTION OF THE FIGURES

FIG. 7 provides a sequence alignment prepared using CLUSTAL OMEGA™ (1.2.4) multiple sequence alignment (from EMBL-EBI, a part of the European Molecular Biology Laboratory) for the heavy chain variable region amino acid sequences, with CDRs highlighted in bold typeface: CDR1 (marked with +), CDR 2 (marked with ^), and CDR3 (marked with #). The sequences shown include 10.4B (SEQ ID NO: 33), 19.7E (SEQ ID NO: 34), 2.9D (SEQ ID NO: 35), 25.6A (SEQ ID NO: 36), 36.1F (SEQ ID NO: 37), 36.9F (SEQ ID NO: 38), 37.2D (SEQ ID NO: 39), 37.2G (SEQ ID NO: 40), 37.7H (SEQ ID NO: 41), 8.9F (SEQ ID NO: 42), NE13 (SEQ ID NO: 43), 12.1F (SEQ ID NO: 44), 9.8A (SEQ ID NO: 45), 18.5C (SEQ ID NO: 46), 8.11G (SEQ ID NO: 47), and 25.10C (SEQ ID NO: 48).

FIG. 8 provides a sequence alignment prepared using CLUSTAL OMEGA™ (1.2.4) multiple sequence alignment for the light chain variable region amino acid sequences, with CDRs highlighted in bold typeface: CDR1 (marked with +), CDR 2 (marked with ^), and CDR3 (marked with #). The sequences shown include 10.4B (SEQ ID NO: 49), 19.7E (SEQ ID NO: 50), 2.9D (SEQ ID NO: 51), 25.6A (SEQ ID NO: 52), 36.1F (SEQ ID NO: 53), 36.9F (SEQ ID NO: 54), 37.2D (SEQ ID NO: 55), 37.2G (SEQ ID NO: 56), 37.7H (SEQ ID NO: 57), 8.9F (SEQ ID NO: 58), NE13 (SEQ ID NO: 59), 12.1F (SEQ ID NO: 60), 9.8A (SEQ ID NO: 61), 18.5C (SEQ ID NO: 62), 8.11G (SEQ ID NO: 63), and 25.10C (SEQ ID NO: 64).

DETAILED DESCRIPTION

General Techniques

Figure 1:
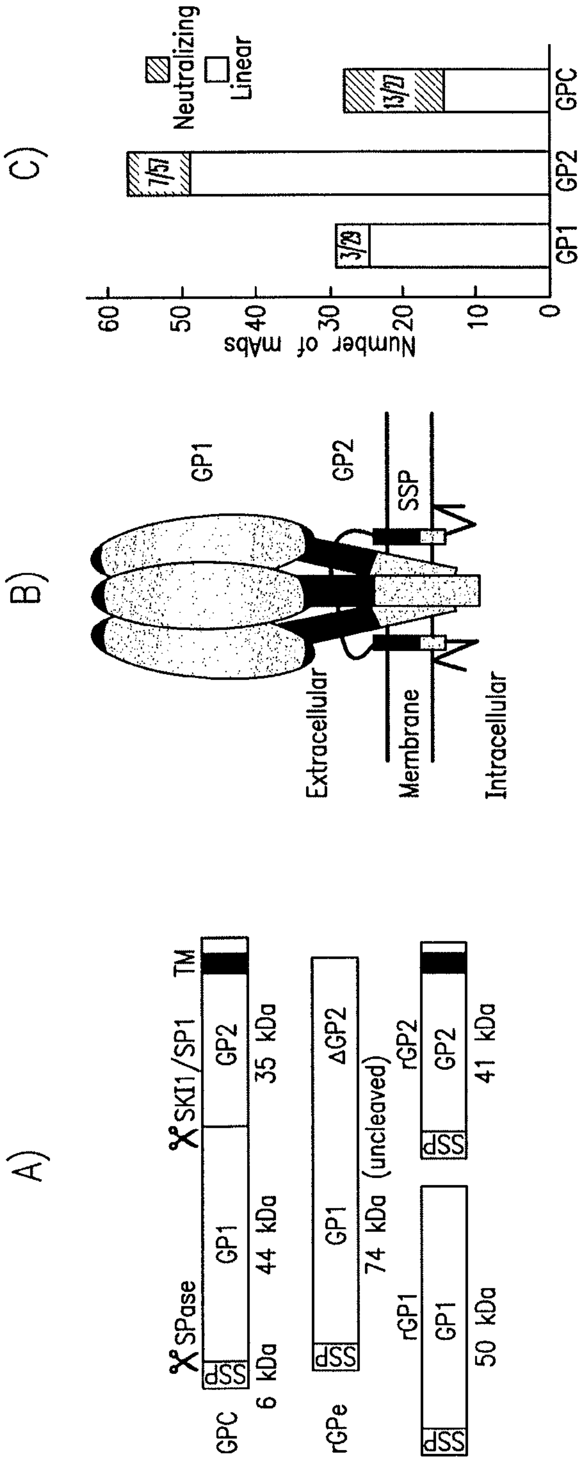
FIG. 1 depicts (A) Schematic representation of LASV GP; (B) Arenavirus GP complex; and (C) Recognition of different LASV GP species by LASV hMAbs. (A) LASV GP is synthesized as the precursor protein GPC. Signal peptidase (Spase) cleaves the small stable signal peptide (SSP) that remains associated with GP1 and GP2 to form the GP complex (FIG. 1, Panel B). The cellular protease SK1/S1P cleaves GPC into GP1 and GP2. Construct rGPe corresponds to a recombinant LASV GPC ectodomain lacking GP2 and with a non-cleavable linker replacing the SK1/S1P cleavage recognition site. Constructs expressing recombinant SSP-GP1 (rGP1) and SSP fused to GP2 (rGP2) were also generated. (B) GP-1 forms the globular head subunit that interact with the cellular receptor whereas GP2 mediates the fusion of the viral envelop with the cell membrane. SSP remains associated with both GP1 and GP2 and plays critical roles in the biology of the GP complex. (C) 293T cells were transfected with pCAGGS expressing plasmids encoding LASV rGP1, rGP2 and GPC and the reactivity of LASV hMAbs evaluated at 48 h post-transfection by immunofluorescence. The distribution of LASV GP-specific hMAbs by subunit specificity, neutralizing activity and reactivity to linear epitopes is indicated.

The practice of the materials and methods described herein will employ, unless otherwise indicated, conventional techniques of molecular biology (including recombinant techniques), microbiology, cell biology, biochemistry, and immunology, which are all within the normal skill of the art. Such techniques are fully explained in the literature, such as, for example, *Molecular Cloning: A Laboratory Manual*, second edition (Sambrook, et al., 1989) Cold Spring Harbor Press; *Methods in Molecular Biology*, Humana Press; *Cell Biology: A Laboratory Notebook* (I. E. Cellis, ed., 1998) Academic Press; *Animal Cell Culture* (R. I. Freshney, ed., 1987); *Introduction to Cell and Tissue Culture* (J. P. Mather and P. E. Roberts, 1998) Plenum Press; *Cell and Tissue*

*Culture: Laboratory Procedures* (A. Doyle, J. B. Griffiths, and D. G. Newell, eds., 1993-8) J. Wiley and Sons; *Methods in Enzymology* (Academic Press, Inc.); *Handbook of Experimental Immunology* (D. M. Weir and C. C. Blackwell, eds.); *Gene Transfer Vectors for Mammalian Cells* (J. M. Miller and M. P. Cabs, eds., 1987); *Current Protocols in Molecular Biology* (F. M. Ausubel, et aL, eds., 1987); *PCR: The Polymerase Chain Reaction*, (Mullis, et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: a practical approach* (D. Catty., ed., IRL Press, 1988-1989); *Monoclonal antibodies: a practical approach* (P. Shepherd and C. Dean, eds., Oxford University Press, 2000); *Using antibodies: a laboratory manual* (E. Harlow and D. Lane (Cold Spring Harbor Laboratory Press, 1999); *The Antibodies* (M. Zanetti and J. D. Capra, eds., Harwood Academic Publishers, 1995).

As used herein, the singular form "a", "an", and "the" includes plural references unless indicated otherwise. For example, "a" monoclonal antibody includes one or more monoclonal antibodies.

Generally, monoclonal antibodies specific for LASV, monoclonal antibodies specific for LCMV, the polynucleotides encoding the antibodies, and methods for using these antibodies in prevention, diagnosis, detection, and treatment are described herein. Specifically, human monoclonal antibodies specific for LASV, human monoclonal antibodies specific for LCMV, and combinations thereof for development and production of diagnostics, vaccines, therapeutics, and screening tools are provided. Generally, B cell clones producing specific IgG to GP of any Lassa virus isolate or strain may be utilized to derive the antibodies described herein.

Polynucleotides

The term polynucleotide is used broadly and refers to polymeric nucleotides of any length (e.g., oligonucleotides, genes, small inhibiting RNA, fragments of polynucleotides encoding a protein, etc.). By way of example and not limitation, the polynucleotides of the invention may comprise a sequence encoding all or part of the ectodomain and part of the transmembrane domain. The polynucleotide of the invention may be, for example, linear, circular, supercoiled, single-stranded, double-stranded, branched, partially double-stranded or partially single-stranded. The nucleotides comprised within the polynucleotide may be naturally occurring nucleotides or modified nucleotides.

Functional equivalents of these polynucleotides are also intended to be encompassed by this invention. By way of example and not limitation, functionally equivalent polynucleotides are those that possess one or more of the following characteristics: the ability to generate antibodies (including, but not limited to, viral neutralizing antibodies) capable of recognizing LASV GP or the ability to generate antibodies specific to LASV GP that show neutralizing activity against LASV lineages I-IV, and proposed new lineages (e.g. lineage V from Mali, lineage VI from Togo and Benin.

Polynucleotide sequences that are functionally equivalent may also be identified by methods known in the art. A variety of sequence alignment software programs are available to facilitate determination of homology or equivalence. Non-limiting examples of these programs are BLAST family programs including BLASTN, BLASTP, BLASTX, TBLASTN, and TBLASTX (BLAST is available from the National Institutes of Health website), FASTA™, COMPARE™, DOTPLOT™, BESTFIT™ GAP™ FRAMEALIGN™, CLUSTALW™, and PILEUP™. Other similar analysis and alignment programs can be purchased from various providers such as DNA Star's MEGALIGN™, or the alignment programs in GENEJOCKEY™. Alternatively, sequence analysis and alignment programs can be accessed through the world wide web at sites such as the CMS Molecular Biology Resource at San Diego Supercomuter Center (SDSC) website; and the Swiss Institute of Bioinformatics SIB Bioinformatics Resource Portal website ExPASy Proteomics Server. Any sequence database that contains DNA or protein sequences corresponding to a gene or a segment thereof can be used for sequence analysis. Commonly employed databases include but are not limited to GenBank, EMBL, DDBJ, PDB, SWISS-PROT, EST, STS, GSS, and HTGS.

Parameters for determining the extent of homology set forth by one or more of the aforementioned alignment programs are well established in the art. They include but are not limited to p value, percent sequence identity and the percent sequence similarity. P value is the probability that the alignment is produced by chance. For a single alignment, the p value can be calculated according to Karlin et al. (1990) *Proc. Natl. Acad. Sci.* (USA) 87: 2246. For multiple alignments, the p value can be calculated using a heuristic approach such as the one programmed in BLAST. Percent sequence identify is defined by the ratio of the number of nucleotide or amino acid matches between the query sequence and the known sequence when the two are optimally aligned. The percent sequence similarity is calculated in the same way as percent identity except one scores amino acids that are different but similar as positive when calculating the percent similarity. Thus, conservative changes that occur frequently without altering function, such as a change from one basic amino acid to another or a change from one hydrophobic amino acid to another are scored as if they were identical.

The term "analog" includes any polypeptide having an amino acid residue sequence substantially identical to a polypeptide of the invention in which one or more residues have been conservatively substituted with a functionally similar residue and which displays the functional aspects of the polypeptides as described herein. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; and the substitution of one acidic residue, such as aspartic acid or glutamic acid or another.

The phrase "conservative substitution" also includes the use of a chemically derivatized residue in place of a non-derivatized residue. "Chemical derivative" refers to a subject polypeptide having one or more amino acid residues chemically derivatized by reaction of a functional side group. Examples of such derivatized amino acids include for example, those amino acids in which free amino groups have been derivatized to form amine hydrochlorides, p-toluene sulfonyl groups, carbobenzoxy groups, t-butyloxycarbonyl groups, chloroacetyl groups or formyl groups. Also, the free carboxyl groups of amino acids may be derivatized to form salts, methyl and ethyl esters or other types of esters or hydrazides. Also, the free hydroxyl groups of certain amino acids may be derivatized to form 0-acyl or 0-alkyl derivatives. Also, the imidazole nitrogen of histidine may be derivatized to form N-imbenzylhistidine. Also included as chemical derivatives are those proteins or peptides which contain one or more naturally occurring amino acid derivatives of the twenty standard amino acids. For example, 4-hydroxyproline may be substituted for proline, 5-hydroxylysine may be substituted for lysine, 3-methylhistidine may be substituted for histidine, homoserine may be substituted for serine, and ornithine may be substituted for lysine. Polypeptides of the present invention also include any polypeptide having one or more additions and/or deletions of residues relative to the sequence of any one of the polypeptides whose sequence is described herein.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75 contiguous positions, or 40 to about 50 contiguous positions, in which a sequence may be compared to a reference sequence of the same number of contiguous positions after the two sequences are optimally aligned.

Optimal alignment of sequences for comparison may be conducted using the MEGALIGN™ program in the LASERGENE™ suite of bioinformatics software (DNASTAR, Inc., Madison, WI), using default parameters. This program embodies several alignment schemes described in the following references: Dayhoff, M. O. (1978) "A model of evolutionary change in proteins—Matrices for detecting distant relationships" in Dayhoff, M. O. (ed.) *Atlas of Protein Sequence and Structure*, National Biomedical Research Foundation, Washington DC Vol. 5, Suppl. 3, pp. 345-358 (1978); Hem J., "Unified Approach to Alignment and Phylogenes" pp. 626-645 *Methods in Enzymology* vol. 183, Academic Press, Inc., San Diego, CA (1990); Higgins, D. G. and Sharp, P. M., 1989, *CABIOS* 5:151-153; Myers, E. W. and Muller W., 1988, *CABIOS* 4:11-17; Robinson, E. D., 1971, *Comb. Theor.* 11:105; Santou, N., Nes, M., 1987, *Mol. Biol. Evol.* 4:406-425; Sneath, P. H. A. and Sokal, R. R., 1973, *Numerical Taxonomy the Principles and Practice of Numerical Taxonomy*, Freeman Press, San Francisco, CA; Wilbur, W. J. and Lipman, D. J., 1983, *Proc. Natl. Acad. Sci. USA* 80:726-730.

Preferably, the "percentage of sequence identity" is determined by comparing two optimally aligned sequences over a window of comparison of at least 20 positions, wherein the portion of the polypeptide sequence in the comparison window may comprise additions or deletions (i.e., gaps) of 20 percent or less, usually 5 to 15 percent, or 10 to 12 percent, as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the reference sequence (i.e., the window size) and multiplying the results by 100 to yield the percentage of sequence identity.

Expression Vectors

Expression vectors comprising at least one polynucleotide encoding an antibody or antibody fragment protein also are described herein. Expression vectors are well known in the art and include, but are not limited to viral vectors or plasmids. Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127), alphavirus-based vectors (e.g., Sindbis virus vectors, Semliki forest virus), Ross River virus, adeno-associated virus (AAV) vectors (see, e.g., PCT Publication Nos. WO 94/12649, WO 93/03769; WO 93/19191; WO 94/28938; WO 95/11984 and WO 95/00655), vaccinia virus (e.g., Modified Vaccinia virus Ankara (MVA) or fowlpox), Baculovirus recombinant system and herpes virus.

Nonviral vectors, such as plasmids, are also well known in the art and include, but are not limited to, yeast- and bacteria-based plasmids.

Methods of introducing the vectors into a host cell and isolating and purifying the expressed protein are also well known in the art (e.g., *Molecular Cloning: A Laboratory Manual*, second edition, Sambrook, et al., 1989, Cold Spring Harbor Press). Examples of host cells include, but are not limited to, mammalian cells such as NS0 and CHO cells.

By way of example, vectors comprising the polynucleotides described herein may further comprise a tag polynucleotide sequence to facilitate protein isolation and/or purification. Examples of tags include but are not limited to the myc-epitope, S-tag, his-tag, HSV epitope, V5-epitope, FLAG and CBP (calmodulin binding protein). Such tags are commercially available or readily made by methods known to the art.

The vector may further comprise a polynucleotide sequence encoding a linker sequence. Generally, the linking sequence is positioned in the vector between the antibody polynucleotide sequence and the polynucleotide tag sequence. Linking sequences can encode random amino acids or can contain functional sites. Examples of linking sequences containing functional sites include but are not limited to, sequences containing the Factor Xa cleavage site, the thrombin cleavage site, or the enterokinase cleavage site.

By way of example, and not limitation, an antibody specific for LASV may be generated as described herein using mammalian expression vectors in mammalian cell culture systems or bacterial expression vectors in bacterial culture systems. By way of example, and not limitation, an antibody specific for LCMV may be generated as described herein using mammalian expression vectors in mammalian cell culture systems or bacterial expression vectors in bacterial culture systems.

Antibodies

Examples of antibodies disclosed herein, include, but are not limited to, antibodies specific for LASV or LCMV, antibodies that cross react with native Lassa virus antigens and/or native lymphocytic choriomeningitis virus antigens, and neutralizing antibodies. By way of example, a characteristic of a neutralizing antibody includes the ability to block or prevent infection of a host cell. The antibodies may be characterized using methods well known in the art.

The antibodies useful in the compositions and methods described herein can encompass monoclonal antibodies, polyclonal antibodies, antibody fragments (e.g., Fab, Fab', F(ab')2, Fv, Fc, etc.), chimeric antibodies, bi-specific antibodies, heteroconjugate antibodies, single-chain fragments (e.g. ScFv), mutants thereof, fusion proteins comprising an antibody portion, humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or of any other origin (including chimeric or humanized antibodies).

Methods of preparing monoclonal and polyclonal antibodies are well known in the art. Polyclonal antibodies can be raised in a mammal, for example, by one or more injections of an immunizing agent and, if desired an adjuvant. Examples of adjuvants include, but are not limited to, keyhole limpet hemocyanin (KLH), serum albumin, bovine thryoglobulin, soybean trypsin inhibitor, complete Freund adjuvant (CFA), and MPL-TDM adjuvant. The immunization protocol can be determined by one of skill in the art.

The antibodies may alternatively be monoclonal antibodies. Monoclonal antibodies may be produced using hybridoma methods (see, e.g., Kohler, B. and Milstein, C. (1975) *Nature* 256:495-497 or as modified by Buck, D. W., et al., *In Vitro,* 18:377-381(1982).

If desired, the antibody of interest may be sequenced and the polynucleotide sequence may then be cloned into a vector for expression or propagation. The sequence encoding the antibody of interest may be maintained in the vector in a host cell, and the host cell can then be expanded and frozen for future use. In an alternative embodiment, the polynucleotide sequence may be used for genetic manipulation to "humanize" the antibody or to improve the affinity, or other characteristics of the antibody (e.g., genetically manipulate the antibody sequence to obtain greater affinity to LASV and/or LCMV glycoprotein and/or greater efficacy in inhibiting the fusion of LASV and/or LCMV to the host cell).

The antibodies may also be humanized by methods known in the art (See, for example, U.S. Pat. Nos. 4,816,567; 5,807,715; 5,866,692; 6,331,415; 5,530,101; 5,693,761; 5,693,762; 5,585,089; and 6,180,370). In yet another alternative, human antibodies may be obtained by using mice that have been engineered to express specific human immunoglobulin proteins.

In another alternative embodiment, antibodies may be made recombinantly and expressed using any method known in the art. By way of example, antibodies may be made recombinantly by phage display technology. See, for example, U.S. Pat. Nos. 5,565,332; 5,580,717; 5,733,743; and 6,265,150; and Winter et at., *Annu. Rev. Immunol.* 12:433-455 (1994). Alternatively, phage display technology (McCafferty et al., *Nature* 348:552-553 (1990)) can be used to produce human antibodies and antibody fragments in vitro. Phage display can be performed in a variety of formats; for review, see Johnson, Kevin S. and Chiswell, David J., *Current Opinion in Structural Biology* 3:564-571 (1993). By way of example, LASV and/or LCMV glycoprotein as described herein may be used as an antigen for the purposes of isolating recombinant antibodies by these techniques.

Antibodies may be made recombinantly by first isolating the antibodies and antibody producing cells from host animals, obtaining the gene sequence, and using the gene sequence to express the antibody recombinantly in host cells (e.g., CHO cells). Another method that may be employed is to express the antibody sequence in plants (e.g., tobacco) or transgenic milk. Methods for expressing antibodies recombinantly in plants or milk have been disclosed. See, for example, Peeters, et al. *Vaccine* 19:2756 (2001); Lonberg, N. and D. Huszar *Int. Rev. Immunol* 13:65 (1995); and Pollock, et al., *J. Immunol. Methods* 231:147 (1999). Methods for making derivatives of antibodies (e.g. humanized and single-chain antibodies, etc.) are known in the art.

The antibodies described herein can be bound to a carrier by conventional methods for use in, for example, isolating or purifying LASV and/or LCMV glycoprotein or detecting LASV and/or LCMV glycoproteins, antigens, or particles in a biological sample or specimen. Alternatively, by way of example, the neutralizing antibodies of the invention may be administered as a therapeutic treatment to a subject infected with or suspected of being infected with LASV or LCMV. A "subject," includes but is not limited to humans, simians, farm animals, sport animals, and pets. Veterinary uses are also encompassed by methods described herein. For diagnostic purposes, the antibodies can be labeled, e.g., bound to a detectable labelling group such as a fluorescent dye (e.g., a ALEXA FLUOR® dye), a quantum dot label (e.g., a QDOT® label), R-phycoerythrin, streptavidin, biotin, an enzyme (e.g., Glucose Oxidase, Horseradish Peroxidase or Alkaline Phosphatase), a radioiosotope (e.g., iodine-125, indium-111), and the like. Such labelling techniques are well known in the antibody art.

Antibody DNA Sequences

Sixteen neutralizing antibodies against LASV were identified, which are designated herein as 10.4B, 19.7E, 2.9D, 25.6A, 36.1F, 36.9F, 37.2D, 37.2G, 37.7H, 8.9F, NE13, 12.1F, 9.8A, 18.5C, 8.11G, and 25.10C. Nucleotide sequences (cDNA) encoding portions of heavy chain (HC) and light chain (LC) of each antibody are shown below. The illustrated nucleotide sequences encode portions of the HC and LC encompassing the variable regions thereof, i.e., the $V_H$ and $V_L$ regions, respectively, along with portions of vector sequences.

(10.4B $V_H$)

SEQ ID NO: 1

```
tgcgcgttac ngatccaagc tgtgaccggc gcctacctga gatcaccggt gctagcacca    60

tggagacaga cacactcctg ctatgggtac tgctgctctg ggttccaggt tccactggtg   120

accaggtgca gctggtacag tctgggggag gcgtggtcca gcctgggagg tccctgagag   180

tctcctgtgt tacgtctgga ttcaatttca gagcctacgg catgcactgg gtccgccaga   240

ttccaggcaa gggactggag tgggtggcag atatttggtc tgccgagact aatagacact   300

atgcagattc cgtgaagggc cgattcacca tctccagaga caactccaag agcacactgt   360

atctgcaaat gaacagcctg agagccgagg acacgggcgt atatttctgt gccaaagcgc   420

gaccaggcta tgattatgtc gttgacttat ggggccaggg aacgctggtc atcgtctcct   480

cagcttccac caagggccca tcggtcttcc ccctggcgcc ctgctccagg agcacctctg   540
```

-continued

```
ggggcacagc ggccctgggc tgcctggtca aggactactt ccccgaaccg gtgacggtgt        600
cgtggaactc aggcgccctg accagcggcg tgcacacctt cccggctgtc ctacagtcct        660
caggactcta                                                               670
```

(19.7E $V_H$)

SEQ ID NO: 2

```
atccagctgt gaccggcgcc tacctgagat caccggtgct agcaccatgg agacagacac         60
actcctgcta tgggtactgc tgctctgggt tccaggttcc actggtgacg aggtgcagct        120
ggtggagtct gggggaggct tagttcggcc tggggggtcc ctgagactct cctgtgcagc        180
ctctggattc tccttcagta gctactcgat gcactgggtc cgccatgttc ctgggaaggg        240
gctggtgtgg gtctcatata ttaatagtga tgggagtact aaaatctacg cggactccgt        300
gaagggccga ttctccatct ccagagacaa tgccaagaac aagctctatc tgcaaatgga        360
cagtttgaga gtcgaggaca cggctgtata ttcgtgtgta aggcttgtac attacgactg        420
gtccccattc gtgtggggcc agggaaccct ggtcaccgtc tcctcagcct ccaccaaggg        480
cccatcggtc ttcccccctgg caccctcctc caagagcacc tctgggggca cagcggccct        540
gggctgcctg gtcaaggact acttccccga accggtgacg gtgtcgtgga actcaggcgc        600
cctgaccagc ggcgtgcaca ccttcccggc tgtcctacag tcctcaggac tctactccct        660
cagcagcgtg gtgaccgtgc cctccagcag cttgggcacc cagacctaca tctgcaacgt        720
gaatcacaag cccagcaaca ccaaggtgga caagaaagtt gagcccaat cttgtgacaa        780
aactcacaca tgcccaccgt gcccagcacc tgaactcct                              819
```

(2.9D $V_H$)

SEQ ID NO: 3

```
gtcactgcac ctcggttcta tcgattggct agcaccatgg agacagacac actcctgcta         60
tgggtactgc tgctctgggt tccaggttcc actggtgacg aggtgcagct ggtggagtct        120
gggggaggcc tggtcaagcc tggggggtcc cttagactct cctgtgcagc ctctggattc        180
accttcacta gatttacttt gacctgggtc cgccaggctc cagggaaggg gctggagtgg        240
gtctcatcca ttagtagtgg gagtagtgac ataaactacg cagactcagt gaagggccga        300
ttcaccatat ccagagacaa cgccaggaac tccctgttcc tgcaaatgag cagcctgaga        360
gtcgacgaca cggctgtgta ttactgtgcg aaagatcccc ggtcggggat ctctggtcgc        420
tacgggatgg acgtctgggg ccaagggacc acggtcatcg tctcctcagc ttccaccaag        480
ggcccatcgg tcttcccct ggcgccctgc tccaggagca cctctggggg cacagcggcc        540
ctgggctgcc tggtcaagga ctacttcccc gaaccggtga cggtgtcgtg gaactcaggc        600
gccctgacca gcggcgtgca caccttcccg gctgtcctac agtcctcagg actctactcc        660
ctcagcagcg tggtgaccgt gccctccagc agcttgggca cccagaccta catctgcaac        720
gtgaatcaca agcccagcaa caccaaggtg gacaagagag ttgagcccaa atcttgtgac        780
aaaactcaca catgcccacc gtgcccagca cctgaactcc tggggggacc gtcagtcttc        840
ctcttccccc caaaacccaa ggacaccctc atgatctccc ggacccctga ggtcacatgc        900
gtggtggtgg acgtgagcca                                                    920
```

(25.6A $V_H$)

SEQ ID NO: 4

```
acctcggttc ttcgattggc tagcaccatg gagacagaca cactcctgct atgggtactg         60
ctgctctggg ttccaggttc cactggtgac caggtgcagc tgcaggagtc aggaggaggc        120
ctggtcaagg ctggggggtc cctgagactc tcctgtgcag cctctggatt catgttcgag        180
agatatagcc ttcactgggt ccgtcagact ccaggcaagg ggctggagtg ggtctcatcc        240
```

-continued

```
attagtagtc ttagtggcag tcacataaac tacgcagact cagtgaaggg ccgattcacc    300
atctccagag acaacgccaa gaattcactg tctctgcaaa tgaacagcct gagagtcgaa    360
gacacggcta tatattattg tgcgagagat cgacgttcgg ggagttcccc cgtccccttg    420
gacgtctggg gccaagggac cacggtcacc gtctcctctg cctccaccaa gggcccatcg    480
gtcttccccc tggcaccctc ctccaagagc acctctgggg gcacagcggc cctgggctgc    540
```

(36.1F $V_H$)

SEQ ID NO: 5

```
gtcactgccc tcggttctat cgattggcta gcaccatgga gacagacaca ctcctgctat     60
gggtactgct gctctgggtt ccaggttcca ctggtgacca ggtgcagctg caggagtcgg    120
gcgcgggact ggtgaagcct tcggagaccc tgtccctcac ctgcgctgtc tcaggtggac    180
ccttcagcgg tgcctactgg acgtggatcc gccaaactcc agggaagggg ctggagtgga    240
ttggagaggc cggtcggagt ggaaccacca actacaatcc gtccctcaag agtcgagtca    300
ccatatcact ggacacgtcc aagagccagt tttccctgaa gctgacttcc gtgaccgccg    360
cggacacggc tgtttacttc tgtgggagac gccaaataat gtctttgagt aatctttata    420
agagacccgt tgactcttgg ggccggggaa ccccggtcat cgtctcctca gcctccacca    480
agggcccatc ggtcttcccc ctggcaccct cctccaagag cacctctggg ggcacagcgg    540
ccctgggctg cctggtcaag gactacttcc ccgaaccggt gacggtgtcg tggaactcag    600
gcgccctgac cagcggcgtg cacaccttcc cggctgtcct acagtcctca ggactctact    660
ccctcagcag cgtggtgacc gtgccctcca gcagcttggg cacccagacc tacatctgca    720
acgtgaatca caagcccagc aacaccaagg tggacaagag agttgagccc aaatcttgtg    780
acaaaactca cacatgccca ccgtgcccag cacctgaact cctgggggga ccgtcagtct    840
tcctcttccc cccaa                                                     855
```

(36.9F $V_H$)

SEQ ID NO: 6

```
gtcactgccc tcggttctat cgattggcta gcaccatgga gacagacaca ctcctgctat     60
gggtactgct gctctgggtt ccaggttcca ctggtgacga ggtgcagctg gtgcagtctg    120
gaggaggcct ggtcaaggcg ggggggtccc tgaaactctc ctgtggagcc tctggattca    180
ccttcagtag ttatagcatg agctgggtcc gccaggctcc agggaagggg ctggagtggg    240
tctcatacat tagtagtggt gggagttcta tacactacgc agactcagtg aagggccgat    300
tcaccatctc cagagacaac gccaagaatt cactgtatct gcaaatgaag aacctgaggg    360
tcgacgacac gggtcggtat tattgtgtga gagatccccg atcggggatc tctggtcggt    420
acggtatgga cgtctggggt caagggacca cggtcaccgt ctcctcagcc tccaccaagg    480
gcccatcggt cttccccctg gcaccctcct ccaagagcac ctctgggggc acagcggccc    540
tgggctgcct ggtcaaggac tacttccccg aaccggtgac ggtgtcgtgg aactcaggcg    600
ccctgaccag cggcgtgcac accttcccgg ctgtcctaca gtcctcagga ctctactccc    660
tcagcagcgt ggtgaccgtg ccctccagca gcttgggcac ccagacctac atctgcaacg    720
tgaatcacaa gcccagcaac accaaggtgg acaagagagt tgagcccaaa tcttgtgaca    780
aaactcacac atgcccaccg tgcccagcac ctgaactcct ggggggaccg tcagtcttcc    840
tcttcccccc aaacccaagg acaccctcat gatc                                874
```

(37.2D $V_H$)

SEQ ID NO: 7

```
tcactgccct cggttctatc gattggctag caccatggag acagacacac tcctgctatg     60
ggtactgctg ctctgggttc caggttccac tggtgacgaa gtgcagctgg tgcagtctgg    120
agctgaggtg aagaagcctg gggcttcagt gaaggtgtcc tgcaaggcct ctggttacac    180
```

-continued

```
ctttacgaaa tacggaatca gctgggtgcg acaggcccct ggacaagggc ttgagtggat        240
gggatggatc agcgcgttta atggttacac aaggtatggt cagagattcc agggcaaagt        300
caccatgacc acagacacat ccacgaacac agcctctttg gaggtgagga ccctgacatc        360
taacgacacg gccgtctatt actgtgcgag acaatatccc gaccaatata gtagcagcgg        420
ttggccccgc ctcttcgcca tggacgtctg ggccaaggg accacggtca tcgtctcccc         480
agcctccacc aagggcccat cggtcttccc cctggcaccc tcctccaaga gcacctctgg        540
gggcacagcg gccctgggct gcctggtcaa ggactacttc cccgaaccgg tgacggtgtc        600
gtggaactca ggcgccctga ccagcggcgt gcacaccttc ccggctgtcc tacagtcctc        660
aggactctac tccctcagca gcgtggtgac cgtgccctcc agcagcttgg gcacccagac        720
ctacatctgc aacgtgaatc acaagcccag caacaccaag gtggacaaga gagttgagcc        780
caaatcttgt gacaaaactc acacatgccc accgtgccca gcacctgaac tcctgggggg        840
accgtcagtc ttcctcttc                                                      859
```

(37.2G $V_H$)

```
                                                                  SEQ ID NO: 8
tcactgccct cggttctatc gattggctag caccatggag acagacacac tcctgctatg         60
ggtactgctg ctctgggttc caggttccac tggtgacgag gtgcagctgg tggagtctgg        120
gggaggcctg gtcaagccgg gggggtcccg gagactctcc tgtgctgcct ctggattcac        180
cttcagtaga gataccatga cctgggtccg ccaggctcca gggaaggggc tggagtgggt        240
cgcatccata agtagtggta gcagtgacat aaactacgca gactcagtga agggccgatt        300
caccatctcc agagacaacg gcaagaactc actgtatctg cacatgaaca gcctgagagc        360
cgacgacacg gctatatatt actgtgcgag agatccccgg tcgggaatct ctggtcggta        420
tggtatggac gtctggggcc aagggaccac ggtcaccgtc tcctcagcct ccaccaaggg        480
cccatcggtc ttcccccctgg caccctcctc caagagcacc tctgggggca cagcggccct        540
gggctgcctg gtcaaggact acttccccga accggtgacg gtgtcgtgga actcaggcgc        600
cctgaccagc ggcgtgcaca ccttcccggc tgtcctacag tcctcaggac tctactccct        660
cagcagcgtg gtgaccgtgc cctccagcag cttgggcacc cagacctaca tctgcaacgt        720
gaatcacaag cccagcaaca ccaaggtgga caagagagtt gagcccaaat cttgtgacaa        780
aactcacaca tgcccaccgt gcccagcacc tgaactcctg gggggaccgt cagtcttcct        840
cttcccccca aaacccaagg acaccctcat gatctcccgg acccctgagg tcacatgcgt        900
ggtggtggac gtgagccacg aagaccctga ggtcaagttc aactggtacg tggacggcgt        960
```

(37.7H $V_H$)

```
                                                                  SEQ ID NO: 9
gtcactgcac ctcggttcta tcgattggct agcaccatgg agacagacac actcctgcta         60
tgggtactgc tgctctgggt tccaggttcc actggtgacg aggtgcagct ggtgcagtct        120
ggaggaggcc tggtcaaggc ggggggggtcc ctgaggctct cctgtgcagc ctccggattc       180
acattcagca cctacagtat gaactggatc cgccaggctc cagggaaggg gctggagtgg        240
gtcgcttcca ttagtagtcg aagtggcagt cacataaact acgtagactc agtgaaggga        300
cgattcacca tctccagaga caacgccagg gacttattgt atctgcaaat gaacagcctg        360
agagtcgacg actcggctct ctattactgt gcgagagatc gccgttcggg gacttctccc        420
ctccccttgg acgtctgggg ccaagggacc acggtcaccg tcttctcagc ctccaccaag        480
ggcccatcgg tcttcccccct ggcaccctcc tccaagagca cctctggggg cacagcggcc       540
ctgggctgcc tggtcaagga ctacttcccc gaaccggtga cggtgtcgtg gaactcaggc        600
```

-continued

```
gccctgacca gcggcgtgca caccttcccg gctgtcctac agtcctcagg actctactcc    660
ctcagcagcg tggtgaccgt gccctccagc agcttgggca cccagaccta catctgcaac    720
gtgaatcaca agcccagcaa caccaaggtg gacaagagag ttgagcccaa atcttgtgac    780
aaaactcaca catgcccacc gtgcccagca cctgaactcc tggggggacc gtcagtcttc    840
ctcttccccc caaaacccaa ggacaccctc atgatctccc ggacccctga ggtcacatgc    900
gtggtggtgg acgtgagcca cgaa                                           924
```

(8.9F $V_H$)

SEQ ID NO: 10

```
cctcggttct atcgattggc tagcaccatg gagacagaca cactcctgct atgggtactg     60
ctgctctggg ttccaggttc cactggtgac cagggcacct tgagggagtc tggtccagga    120
ctggtgaggc cttcggagac cctgtccctc acctgcggtg tctctggtta ttccatcagt    180
agtggttact actggggctg gatccggcag cccccaggga aggggctgga gtggattggg    240
aatatctatc gtagtgggag cacctactac aacccgtccc tcaagagtcg agtcaccgtc    300
tcaatagaca cgtccaaaaa ccagttctcc ctgaagttga attctgtgac cgccgcagac    360
acggccgtgt attactgtgc gagatcgggt ataaaagtgg ctgacgacta ttactacgaa    420
atggacgtct ggggccaagg gaccgacgac tactcttacg ctatggacgt ctggggccaa    480
gggaccacgg tcaccgtctc ctcagcctcc accaagggcc catcggtctt ccccctggca    540
ccctcctcca agagcacctc tgggggcaca gcggccctgg gctgcctggt caaggactac    600
ttccccgaac cggtgacggt gtcgtggaac tcaggcgccc tgaccagcgg cgtgcacacc    660
ttcccggctg tcctacagtc ctcaggactc tactccctca gcagcgtggt gaccgtgccc    720
tccagcagct tgggcaccca gacctacatc tgcaacgtga atcacaagcc cagcaacacc    780
aaggtggaca agagagttga gcccaaatct tgtgacaaaa ctcacacatg cccaccgtgc    840
ccagcacctg aactcctggg gggaccgtca gtcttcctct tccccccaaa acccaaggac    900
accctcatga t                                                         911
```

(NE13 $V_H$)

SEQ ID NO: 11

```
actgcacctc ggttctatcg attggctagc accatggaga cagacacact cctgctatgg     60
gtactgctgc tctgggttcc aggttccact ggtgacgagg ttcagctggt ggagtctggg    120
ggaggcctgg tcaagcctgg ggggtccctg agactctcct gtgtagcctc tggattcacc    180
ttcagttcct atagcatgaa ctgggtccgc caggctccag ggaaggggct ggagtgggtc    240
tcatccatta gtagtggtag tagttacata gagtacgcag actcagtgaa gggccgactc    300
accatctcca gagacaacgc caagaagtca ctgtatctgc aactgaacag cctgagagcc    360
gaggacacgg ctgtgtatta ctgtgcgaga cacacagctc gaatcgactc ttaccacggt    420
atggacgtct ggggccaagg gaccacagtc accgtctcct cagcctccac caagggccca    480
tcggtcttcc ccctggcacc ctcctccaag agcacctctg gggggcacagc ggccctgggc    540
tgcctggtca aggactactt ccccgaaccg gtgacggtgt cgtggaactc aggcgccctg    600
accagcggcg tgcacacctt cccggctgtc ctacagtcct caggactcta ctccctcagc    660
agcgtggtga ccgtgccctc cagcagcttg ggcacccaga cctacatctg caacgtgaat    720
cacaagccca gcaacaccaa ggtggacaag agagttgagc ccaaatcttg tgacaaaact    780
cacacatgcc caccgtgccc agcacctgaa ctcctggggg gaccgtcagt cttcctcttc    840
cccccaaaac ccaaggacac cctcatgatc tcccggaccc c                        881
```

(12.1F $V_H$)

SEQ ID NO: 12

```
gtcactgcac ctcggttcta tcgattggct agcaccatgg agacagacac actcctgcta     60
```

-continued

```
tgggtactgc tgctctgggt tccaggttcc actggtgacc aggtgcagct gcaggagtcg     120
ggcgcaggac tgttgaagcc ttcggagacc ctgtccctca gttgcactgt cgatggtgag     180
tccttcaatg gtttcttctg gacgtggatc cgccagcccc cagggaaggg tctggagtgg     240
attggagaaa tcaatcatct tgcaagcacc ggctacaacc cgtccctcaa gagtcgagtc     300
accatttcag tagacacgtc caagaaccag ttctctttga agttgacctc tgtgaccgcc     360
gcggacacgg ctgtgtatta ctgtgcgaga ggatacagct atggttttgc atggcccaac     420
taccactatt tggacgtctg ggcaaaggg accacggtca ccgtctcctc agcctccacc      480
aagggcccat cggtcttccc cctggcaccc tcctccaaga gcacctctgg gggcacagcg     540
gccctgggct gcctggtcaa ggactacttc cccgaaccgg tgacggtgtc gtggaactca     600
ggcgccctga ccagcggcgt gcacaccttc ccggctgtcc tacagtcctc aggactctac     660
tccctcagca gcgtggtgac cgtgccctcc agcagcttgg gcacccagac ctacatctgc     720
aacgtgaatc acaagcccag caacaccaag gtggacaaga gagttgagcc caaatcttgt     780
gacaaaactc acacatgccc accgtgccca gcacctgaac tcctgggggg accgtcagtc     840
ttcctcttnc ccccaaaacc caaggacacc ctcatgatct cccggacccc tgaggtcaca     900
tgcgtggtgg tggacgtgag c                                               921
```

(9.8A $V_H$)

SEQ ID NO: 13

```
ttctatcgat ttggctagca ccatggagac 9.8A agacacactc ctgctatggg tactgctgct     60
ctgggttcca ggttccactg gtgacgaggt gcagctggtg cagtctggag gacgcttggt     120
acagcctggg gggtccctga gactctcctg tgtagcctct ggattcacct ttagcagcca     180
tgccatgagc tgggtccgcc aggctccagg gaaggggctg gagtgggtct caggttttag     240
tggtagtagt ggtaccacaa agtacgcaga ctccgtgaag ggccggttca ccatctccag     300
agacaattcc aagaaaacgc tgtatctgca aatgaacagc ctgagagccg aggacacggc     360
cgtatattac tgtgcgaaag gcttctcccc atttcgggga gtacaattcc cctactttga     420
ctactggggc cagggaacgc tggtcaccgt ctcctcagcc tccaccaagg gcccatcggt     480
cttccccctg gcaccctcct ccaagagcac ctctgggggc acagcggccc tgggctgcct     540
ggtcaaggac tacttccccg aaccggtgac ggtgtcgtgg aactcaggcg ccctgaccag     600
cggcgtgcac accttcccgg ctgtcctaca gtcctcagga ctctactccc tcagcagcgt     660
ggtgaccgtg ccctccagca gcttgggcac ccagacctac atctgcaacg tgaatcacaa     720
gcccagcaac accaaggtgg acaagagagt tgagcccaaa tcttgtgaca aaactcacac     780
atgcccaccg tgcccagcac ctgaactcct ggggggaccg tcagtcttcc tcttcccccc     840
aaaacccagg acaccctcat gatctcccgg accc                                 874
```

(18.5C $V_H$)

SEQ ID NO: 14

```
gtccactgca cctcggttct atcgattggc tagcaccatg gagacagaca cactcctgct      60
atgggtactg ctgctctggg ttccaggttc cactggtgac gaggttcagc tggtggagtc     120
tgggggaggc ctggtcaggc cggggggggtc ccttagactc tcctgtgcag ccgctggatt    180
cactttcaag agttatagca tgaattgggt ccgccaggct ccagggaggg gcctggagtg     240
ggtctcatct atcactagtg gtggtagtaa gacatactat gcagacgtag tgaagggccg     300
attcaccgtc tccagagaca acgccaagca gtcgctctat ctgcaaatga acagcctgag     360
agccgaggac acggctatat acttctgtgc gagatcccta catagtacca gccagcctag     420
ctacatggac gtctggggca gaaagatcac ggtcatcgtc tcctcagcct ccaccaaggg     480
```

-continued

```
cccatcggtc ttccccctgg caccctcctc caagagcacc tctgggggca cagcggccct        540
gggctgcctg gtcaaggact acttccccga accggtgacg gtgtcgtgga actcaggcgc        600
cctgaccagc ggcgtgcaca ccttcccggc tgtcctacag tcctcaggac tctactccct        660
cagcagcgtg gtgaccgtgc cctccagcag cttgggcacc cagacctaca tctgcaacgt        720
gaatcacaag cccagcaaca ccaaggtgga caagagagtt gagcccaaat cttgtgacaa        780
aactcacaca tgcccaccgt gcccagcacc tgaactcctg gggggaccgt cagtcttcct        840
cttcccccca aaacccaagg acaccctcat gatctcccgg acccctgagg tcacatgc          898
```

(8.11G $V_H$)

SEQ ID NO: 15

```
tgcacctcgg ttctatcgat tggctagcac catggagaca gacacactcc tgctatgggt         60
actgctgctc tgggttccag gttccactgg tgaccaggtg cagctgcagg agtcgggtcc        120
aggactggtg aagccttcgg agaccctgtc cctcacctgc agtatttctg gtgtgtccac        180
cagaaattat tattggagct ggatccgcca gtccccaggg aagggactgg agtggattgg        240
atatatcttt aacattggga ccaccaacta caatccgtcc ctcaagagtc gactcaccat        300
atctgtagac acgtcgaaga accagttctc cctgaagatc acctctgtga ccgctgcgga        360
cacggccgtc tattactgtg cgagtggatt tgagtacggt gactatacct tcgactactg        420
gggccaggga accccggtca ccgtctcctc agcctccacc aagggcccat cggtcttccc        480
cctggcaccc tcctccaaga gcacctctgg gggcacagcg gccctgggct gcctggtcaa        540
ggactacttc cccgaaccgg tgacggtgtc gtggaactca ggcgccctga ccagcggcgt        600
gcacaccttc ccggctgtcc tacagtcctc aggactctac tccctcagca gcgtggtgac        660
cgtgccctcc agcagcttgg gcacccagac ctacatctgc aacgtgaatc acaagcccag        720
caacaccaag gtggacaaga gagttgagcc caaatcttgt gacaaaactc acacatgccc        780
accgtgccca gcacctgaac tcctgggggg accgtcagtc ttcctcttcc ccccaaaacc        840
caaggacacc ctcatgatct tccggacccc tgaggtcaca tgcgtggtgg tggacgtgag        900
cca                                                                      903
```

(25.10C $V_H$)

SEQ ID NO: 16

```
ctcggttcta tcgattggct agcaccatgg agacagacac actcctgcta tgggtactgc         60
tgctctgggt tccaggttcc actggtgacc aggtgcagct gcaggagtct gggggaggcc        120
tggtcaagcc tgggggggtcc ctgagactct cctgtacagc ctctggattc aacttcaata       180
aatataacat gaactgggtc cgccaggctc cagggaaggg gctggagtgg gtctcatcca        240
ttagtgctct tagcacttac atctattatg cagactcgct gaagggccga ttcaccgtct        300
ccagagacaa cgccaagaac tcactgtttc tgcaaatgaa cagcctgaga gacgacgaca        360
cggctgttta ttactgtgcg agagaaatac gacgtgccag tacctggtcc gccgacctct        420
ggggccgtgg cactctggtc actgtctcct cagcctccac caagggccca tcggtcttcc        480
ccctggcacc ctcctccaag agcacctctg ggggcacagc ggccctgggc tgcctggtca        540
aggactactt ccccgaaccg gtgacggtgt cgtggaactc aggcgccctg accagcggcg        600
tgcacacctt cccggctgtc ctacagtcct caggactcta ctccctcagc agcgtggtga        660
ccgtgccctc cagcagcttg ggcacccaga cctacatctg caacgtgaat cacaagccca        720
gcaacaccaa ggtggacaag agagttgagc ccaaatcttg tgacaaaact cacacatgcc        780
caccgtgccc agcacctgaa ctcctggggg gaccgtcagt cttcctcttc cctccaaacc        840
caaggacacc ctcatgatct                                                    860
```

-continued (10.4B $V_L$)

SEQ ID NO: 17

```
agctgtgacc ggcgcctacc tgagatcacc ggtgctagca ccatggagac agacacactc    60
ctgctatggg tactgctgct ctgggttcca ggttccactg gtgacgaaat tgtgttgaca   120
cagtctccat cctcactgtc tgcgtctgta ggagacagag tcaccatcac ttgtcgggcg   180
agtcgggaca tcaatactta tttaggttgg tttcagcaga gaccagggaa agcccctaag   240
tccctgatct atggtgcatc taatttgcaa aatggggtcc catcaaggtt cagcggcagt   300
ggatctggga cgtattttac tctcaccatc aacggcctgc agactgaaga ctttgcgact   360
tattattgcc aacaatatag catctacccg ctcagtctcg gcggagggac caaggcggac   420
atgaagcgaa ctgtggctgc accatctgtc ttcatcttcc cgccatctga tgagcagttg   480
aaatctggaa ctgcctctgt tgtgtgcctg ctgaataact tctatcccag agaggccaaa   540
gtacagtgga aggtggataa cgccctccaa tcgggtaact cccaggagag tgtcacagag   600
caggacagca aggacagcac ctacagcctc agcagcaccc tgacgctgag caaagcagac   660
tacgagaaac acaaagtcta cgcctgcgaa gtcacccatc agggcctgag ctcgcc       716
```

(19.7E $V_L$)

SEQ ID NO: 18

```
tcagctgtga ccggcgccta cctgagatca ccggtgctag caccatggag acagacacac    60
tcctgctatg gctcctgctg ctctgggttc caggttccac tggtgacgaa attgtgttga   120
cacagtctcc ttccaccctg tctgcatctg tgggagacag agtcaccatc acttgccggg   180
ccagtcagag tattaataat tggttggcct ggtatcagga gaaaccaggg aaagccccta   240
agctcctgat aaataaggcg tctagtttag aaagtggggt cccatcaagg ttcagcggca   300
gtggatctgg gacagaattc actctcacca tcaccagcct gcagcctgat gattttgcaa   360
cttattactg ccaacaatat aatagtaatt cgtggacgtt cggccaaggg accaaggtgg   420
acatgaaacg aactgtggct gcaccatctg tcttcatctt cccgccatct gatgagcagt   480
tgaaatctgg aactgcctct gttgtgtgcc tgctgaataa cttctatccc agagaggcca   540
aagtacagtg gaaggtggat aacgccctcc aatcgggtaa ctcccaggag agtgtcacag   600
agcaggacag caaggacagc acctacagcc tcagcagcac cctgacgctg agcaaagcag   660
actacgagaa acacaaagtc tacgcctgcg aagtcaccca tcagggcctg agctcgcccg   720
tcacaaagag cttcaacagg ggagagtgtt agagggagct agctcgacat gataagatac   780
attgatgagt ttgggacaac cacaactaga atgcagtgaa aaaaatgctt tatttgtgaa   840
atttgtgatg ctattgcttt tattgtgaaa tttgtgatgc tattgcttta tttgtaacca   900
ttataa                                                              906
```

(2.9D $V_L$)

SEQ ID NO: 19

```
actgcacctc ggttctatcg attggctagc accatgaaga cagacacact cctgctatgg    60
gtactgctgc tctgggttcc aggttccact ggtgacgaca ttgtgctgac ccagtctcca   120
gactccctgg ctgtgtctct gggcgagagg gccaccatca actgcaagtc cagccagagt   180
gttttataca gctccaacaa taagaactac ttagcttggt accagcagaa gccaggacag   240
cctcctaagc tgctcattta ctgggcatct acccgggaat ccggggtccc tgaccgattc   300
agtggcagcg ggtctgggac agatttcact ctcaccatca gcagcctgca ggctgaagat   360
gtggcagttt attactgtca gcaatattat agtactcctc cgacgttcgg ccaagggacc   420
aaggtggaaa tcaaacgaac tgtggctgca ccatctgtct tcatcttccc gccatctgat   480
gagcagttga aatctggaac tgcctctgtt gtgtgcctgc tgaataactt ctatcccaga   540
```

-continued

```
gaggccaaag tacagtggaa ggtggataac gccctccaat cgggtaactc ccaggagagt        600
gtcacagagc aggacagcaa ggacagcacc tacagcctca gcagcaccct gacgctgagc        660
aaagcagact acgagaaaca caaagtctac gcctgcgaag tcacccatca gggcctgagc        720
tcgcccgtca caaagagctt caacagggga gagtgttagg cggccgcaag cttggccgcc        780
atggcccaac ttgtttattg cagcttataa tggttacaaa taaagcaata gcatcacaaa        840
tttcacaaat aaagcatttt tttcactgca ttctagttgt ggtttgtcca actc              894
```

(25.6A $V_L$)

SEQ ID NO: 20

```
ctcggttcta tcgattggct agcaccatgg agacagacac actcctgcta tgggtactgc         60
tgctctgggt tccaggttcc actggtgacc tgcctgtgct gactcagcct gcctccgtgt        120
ctgggtctcc tggacagtcg atcaccatct cctgcactgg aaccagcagt gacgttggtg        180
cttataacta tgtctcctgg taccaacagc acccaggcaa agcccccaaa ctcataattt        240
atgaagtcaa gattcggccg tcaggggtgt ctaatcgttt ctctggctcc aagtctggca        300
acacggcctc cctgaccatc tctgggctcc aggctgagga cgaggctgat tatttttgca        360
gctcatattc aaccaacagc ccttgggtgt tcggcggagg gacgaaggtg accgtcctac        420
gtcagcccaa ggctgccccc tcggtcactc tgttcccacc ctcctctgag gagcttcaag        480
ccaacaaggc cacactggtg tgtctcataa gtgacttcta cccgggagcc gtgacagtgg        540
cctggaaggc agatagcagc ccggtcaagg cgggagtgga gaccaccaca ccctccaaac        600
aaagcaacaa caagtacgcg gccagcagct acctgagcct gacgcctgag cagtggaagt        660
cccacagaag ctacagctgc caggtcacgc atgaagggag caccgtggag aagacagtgg        720
cccctacaga atgttcatga gcggccgcaa gcttggccgc catggcccaa cttgtttatt        780
gcagcttata atggttacaa ataaagcaat agcatcacaa atttcacaaa taaagcattt        840
ttttcactgc attctagttg tggtttgtcc aaactcatca atgtatctta tcatgtctgg        900
atc                                                                      903
```

(36.1F $V_L$)

SEQ ID NO: 21

```
tccaggtcac tgcacctcgg ttctatcgat tggctagcac catggagaca gacacactcc         60
tgctatgggt actgctgctc tgggttccag gttccactgg tgacgaaatt gtgctgacac        120
agtctccagg caccctgtct ttgtctccag gggaaagagc caccctctcc tgcagggcca        180
gtcagagtgt tactaaaaac tacttagcct ggtaccagca gaaacctggc caggctccca        240
ccctcgtcat ctatgatgca tccaccaggg ccagtggcat cccagacagg ttcattggca        300
gtgggtctgg gacagacttc actctcacca tcagcagact ggagcctgaa gattttgcag        360
tatattactg ccaccagtat ggcagctcac ctccgtacac ttttggccgg gggaccaagc        420
tggagatcaa acgaactgtg gctgcaccat ctgtcttcat cttcccgcca tctgatgagc        480
agttgaaatc tggaactgcc tctgttgtgt gcctgctgaa taacttctat cccagagagg        540
ccaaagtaca gtggaaggtg gataacgccc tccaatcggg taactcccag gagagtgtca        600
cagagcagga cagcaaggac agcacctaca gcctcagcag caccctgacg ctgagcaaag        660
cagactacga gaaacacaaa gtctacgcct gcgaagtcac ccatcagggc ctgagctcgc        720
ccgtcacaaa gagcttcaac aggggagagt gttaggcggc cgcaagcttg gccgccatgg        780
cccaacttgt ttattgcagc ttataatggt tacaaataaa gcaatagcat cacaaatttc        840
acaaataaag catttttttc actgcattct agttgtgggt tgtccaaact catcaatgta        900
```

(36.9F $V_L$)

SEQ ID NO: 22

```
aggtcactgc acctcggttc tatcgattgg ctagcaccat ggagacagac acactcctgc         60
```

-continued

```
tatgggtact gctgctctgg gttccaggtt ccactggtga cgacatcgtg atgacccagt        120
ctccagactc cctggctgtg tctctgggcg agagggccac catcaactgc aagtccagcc        180
agactgtttt gttcacctcc tattacgtag cttggtatca acaaaagcca gggcagccgc        240
ctaagttgct cttttccggg gcctcttctc gggaatccgg ggtccctgac cgattcagtg        300
ccggcgggtc tgggacagat ttctatctca ccatcaacag cctgcaggct gaagatgtgg        360
cagattacta ttgtcagcaa tatcatactc ctcctttcac tttcggcgga gggaccaagc        420
tggagatcag acgaactgtg gctgcaccat ctgtcttcat cttcccgcca tctgatgagc        480
agttgaaatc tggaactgcc tctgttgtgt gcctgctgaa taacttctat cccagagagg        540
ccaaagtaca gtggaaggtg gataacgccc tccaatcggg taactcccag gagagtgtca        600
cagagcagga cagcaaggac agcacctaca gcctcagcag caccctgacg ctgagcaaag        660
cagactacga gaaacacaaa gtctacgcct gcgaagtcac ccatcagggc ctgagctcgc        720
ccgtcacaaa gagcttcaac aggggagagt gttaggcggc cgcaagcttg gccgccatgg        780
cccaacttgt ttattgcagc ttataatggt tacaaataaa gcaatagcat cacaaatttc        840
acaaataaag catttttttc actgcattct agttgtggtt tgtccaaact catcaatgta        900
tcttatcatg tctggatcgg ga                                                 922
```

(37.2D $V_L$)

SEQ ID NO: 23

```
tcactgcacc tcggttctat cgattggcta gcaccatgga gacagacaca ctcctgctat         60
gggtactgct gctctgggtt ccaggttcca ctggtgacga aacgacactc acgcagtctc        120
cagccaccct gtctgtgtct ccaggggaaa cagccaccct ctcctgcagg gccagtcaaa        180
atgttatcaa caacttagcc tggtaccagc agaaacctgg ccaggctccc aggctcctca        240
tttatggtgc atccaccagg gccactggta tcccagccag gttcagtggc agtgggtctg        300
ggacagagtt cactctcacc atcagcagca tgcagtctga agattttgca gtttattact        360
gtcagcaata taatgactgg cctcgaagtt ttggccaggg gaccaggctg gacatcagac        420
gaactgtggc tgcaccatct gtcttcatct tcccgccatc tgatgagcag ttgaaatctg        480
gaactgcctc tgttgtgtgc ctgctgaata acttctatcc cagagaggcc aaagtacagt        540
ggaaggtgga taacgccctc caatcgggta actcccagga gagtgtcaca gagcaggaca        600
gcaaggacag cacctacagc ctcagcagca ccctgacgct gagcaaagca gactacgaga        660
aacacaaagt ctacgcctgc gaagtcaccc atcagggcct gagctcgccc gtcacaaaga        720
gcttcaacag gggagagtgt taggcggccg caagcttggc cgccatggcc caacttgttt        780
attgcagctt ataatggtta caaataaagc aatagcatca caaatttcac aaataaagca        840
tttttttcac tgcattct                                                      858
```

(37.2G $V_L$)

SEQ ID NO: 24

```
tccaggtcac tgccctcggt tctatcgatt ggctagcacc atggagacag acacactcct         60
gctatgggta ctgctgctct gggttccagg ttccactggt gacgacattg tgctgaccca        120
gtctccaggc accctgtctt tgtctccagg ggaaagagcc accctctcct gcagggccag        180
tcagagtgtg aacagcatct tcttagcctg gtaccagcag aaacctggcc aggctcccag        240
gctcctcatc tatggtgcat ccagcagggc cactggcatc ccagacaggt tcagtggcag        300
tgggtctggg acagacttca ctctcaccat cagcagactg gagcctgagg attttgcagt        360
gtattactgt cagcagtatc atagctcacc taagctcact ttcggcggag ggaccaaggt        420
ggagatcaaa cgaactgtgg ctgcaccatc tgtcttcatc ttcccgccat ctggtgagca        480
```

-continued

```
gttgaaatct ggaactgcct ctgttgtgtg cctgctgaat aacttctatc ccagagaggc    540
caaagtacag tggaaggtgg ataacgccct ccaatcgggt aactcccagg agagtgtcac    600
agagcaggac agcaaggaca gcacctacag cctcagcagc accctgacgc tgagcaaagc    660
agactacgag aaacacaaag tctacgcctg cgaagtcacc catcagggcc tgagctcgcc    720
cgtcacaaag agcttcaaca ggggagagtg ttaggcggcc gcaagcttgg ccgccatggc    780
ccaacttgtt tattgcagct tataatggtt acaaataaag caatagcatc acaaatttca    840
caaataaagc atttttttca ctgcattcta gttgtggttt gtccaaactc atcaatgtat    900
cttatcatgt ctggatcggg aattaattcg gcgcagcacc atggcctgaa ataacctc      958
```

(37.7H $V_L$)

SEQ ID NO: 25

```
tcactgcacc tcggttctat cgattggcta gcaccatgga gacagacaca ctcctgctat     60
gggtactgct gctctgggtt ccaggttcca ctggtgacca gtctgccctg actcagcctg    120
cctccgtgtc tgggtctcct ggacagtcga tcaccatctc ctgcactgga accggcagtg    180
acattggtgg ttataacttt gtctcctggt accaacagta tcccggcaaa gcccccaaac    240
tcattattta tgaggtccgt attcgggcct caggggtttc caatcgcttc tctggctcca    300
agtctggcaa cacggcctcc ctgaccatct ctggactcca ggctgaggac gaggctgatt    360
attactgcaa ctcatattca atccacagcc cttgggtgtt cggcggaggg accaagttga    420
ccgtcctgcg tcagcccaag gctgccccct cggtcactct gttcccaccc tcctctgagg    480
agcttcaagc caacaaggcc acactggtgt gtctcataag tgacttctac ccgggagccg    540
tgacagtggc ctggaaggca gatagcagcc ccgtcaaggc gggagtggag accaccacac    600
cctccaaaca aagcaacaac aagtacgcgg ccagcagcta cctgagcctg acgcctgagc    660
agtgggagtc ccacagaagc tacagctgcc aggtcacgca tgaagggagc accgtggaga    720
agacagtggc ccctacagaa tgttcatgag cggccgcaag cttggccgcc atggcccaac    780
ttgtttattg cagcttataa tggttacaaa taaagcaata gcatcacaaa tttcacaaat    840
aaagcatttt tttcactgca ttctagttgt ggtttgtcca aactcatcaa tgtatcttat    900
catgtctgga tcgggaatta attcggcgca gcaccatggc ctgaaatacc ctctgaaaga    960
ggaacttggt taggtacctt ctgaggcgga aagaaccatc tgtggaatgt gtgtc        1015
```

(8.9F $V_L$)

SEQ ID NO: 26

```
cactgccctc ggttctatcg attggctagc accatggaga cagacacact cctgctatgg     60
gtactgctgc tctgggttcc aggttccact ggtgaccagg cagggctgac tcagcctgcc    120
tccgtgtctg ggtctcctgg acagtcgatc accatctcct gcactgcagc caacagtgac    180
attggtgatt ttaactttgt ctcctggtac caacagcgcc cagacaaagc cccccaaactc   240
atggtttatg aggtcagcag tcggccctca ggggtttcta atcgcttctc tggctccaag    300
tctggcaaca cggcctccct gaccatctct gggctccagg ctgaggacga ggctgattat    360
tactgcacct catatacaag cagcagcact tttgtcttcg gaactgggac caaggtcacc    420
gtcctaggtc agcccaaggc caaccccact gtcactctgt tcccgccctc ctctgaggag    480
cttcaagcca acaaggccac actggtgtgt ctcataagtg acttctaccc gggagccgtg    540
acagtggcct ggaaggcaga tagcagcccc gtcaaggcgg gagtggagac caccacaccc    600
tccaaacaaa gcaacaacaa gtacgcggcc agcagctacc tgagcctgac gcctgagcag    660
tggaagtccc acagaagcta cagctgccag gtcacgcatg aagggagcac cgtggagaag    720
acagtggccc ctacagaatg ttcatgagcg gccgcaagct tggccgccat ggcccaactt    780
gtttattgca gcttataatg gttacaaata aagcaatagc atcacaaatt tcacaaataa    840
```

-continued

```
agcatttttt tcactgcatt ctagttgtgg tttgtccaaa ctcatcaatg tatcttatca        900

tgtctggatc                                                               910
```

($NE13\ V_L$)

SEQ ID NO: 27

```
ctcccaggtc actgcacctc ggttctatcg attggctagc accatggaga cagacacact         60

cctgctatgg gtactgctgc tctgggttcc aggttccact ggtgacgaaa cgacactcac        120

gcagtctcca ggcaccctgt ctttgtctcc aggggaaaga gccaccctct cctgcagggc        180

cagtcagagt gttagcagca cctacttagc ctggtaccag cagaaacctg gccagtctcc        240

caggctcctc atttatggtg catccagtag ggccactggc atcccagaca ggttcagtgg        300

cagtgggtct gggacacagt tcactctcac catcaacaga ctggagcctg aagattttgc        360

agtgtattac tgtcagcagt ttggtagccc gtggacattc ggccaaggga ccaaggtgga        420

aatcaaacga actgtggctg caccatctgt cttcatcttc ccgccatctg atgagcagtt        480

gaaatctgga actgcctctg ttgtgtgcct gctgaataac ttctatccca gagaggccaa        540

agtacagtgg aaggtggata acgccctcca atcgggtaac tcccaggaga gtgtcacaga        600

gcaggacagc aaggacagca cctacagcct cagcagcacc ctgacgctga gcaaagcaga        660

ctacgagaaa cacaaagtct acgcctgcga agtcacccat cagggcctga gctcgcccgt        720

cacaaagagc ttcaacaggg gagagtgtta ggcggccgca agcttggccg ccatggccca        780

acttgtttat tgcagcttat aatggttaca aataaagcaa tagcatcaca aatttcacaa        840

ataaagcatt tttttcactg cattctagtt gtggtttgtc caaactcatc aatgtatctt        900

atcatgtc                                                                 908
```

($12.1F\ V_L$)

SEQ ID NO: 28

```
gtcactgcac ctcggttcta tcgattggct agcaccatgg agacagacac actcctgcta         60

tgggtactgc tgctctgggt tccaggttcc actggtgacg aaacgacact cacgcagtct        120

ccagccaccc tgtctttgtc tccaggggag agagccaccc tctcctgtag ggccagtcag        180

agtgttagca gctacttagc ctggtaccaa cacaaacctg gccaggctcc caggctcctc        240

atctatggtg catcaaagag ggccactggc atcccgtcca ggttcagtgg cagtgggtct        300

gggacagact tcagtctcac catcagcagc ctagagcctg aagattttgc agtttactac        360

tgtcagcacc gaagcgactg gcggactacc ttcggccaag ggacacgact ggagattaaa        420

cgaactgtgg ctgcaccatc tgtcttcatc ttcccgccat ctgatgagca gttgaaatct        480

ggaactgcct ctgttgtgtg cctgctgaat aacttctatc ccagagaggc caaagtacag        540

tggaaggtgg ataacgccct ccaatcgggt aactcccagg agagtgtcac agagcaggac        600

agcaaggaca gcacctacag cctcagcagc accctgacgc tgagcaaagc agactacgag        660

aaacacaaag tctacgcctg cgaagtcacc catcagggcc tgagctcgcc cgtcacaaag        720

agcttcaaca ggggagagtg ttaggcggcc gcaagcttgg ccgccatggc ccaacttgtt        780

tattgcagct tataatggtt acaaataaag caatagcatc acaaatttca caaataaagc        840

atttttttca ctgcattcta gttgtggttt gtccaaactc atcaatgtat cttatcatgt        900

ctggatcggg aaattaatcg gcgcagcacc at                                      932
```

($9.8A\ V_L$)

SEQ ID NO: 29

```
ggttctatcg attggctagc accatggaga cagacacact cctgctatgg gtactgctgc         60

tctgggttcc aggttccact ggtgacgaca tcgtgatgac ccagtctcct tccaccctgt        120

ctgcatctgt aggagacaga gtcaccatca cttgccgggc cagtcagagt attgataggt        180
```

-continued

```
ggttggcctg gtatcagcag aaaccaggga aagcccctaa gctcctgatc tatcaggcat        240
ctagtttaga aagaggggtc ccatcaaggt tcagcggcag tggatctggg acagaattca        300
ctctcaccat cagcagcctg cagcccgatg attttgcaac ttattactgc caacagtata        360
atggttaccc tctcactttc ggcggaggga ccaaggtgga gatcaaacga actgtggctg        420
caccatctgt cttcatcttc ccgccatctg atgagcagtt gaaatctgga actgcctctg        480
ttgtgtgcct gctgaataac ttctatccca gagaggccaa agtacagtgg aaggtggata        540
acgccctcca atcgggtaac tcccaggaga gtgtcacaga gcaggacagc aaggacagca        600
cctacagcct cagcagcacc ctgacgctga gcaaagcaga ctacgagaaa cacaaagtct        660
acgcctgcga agtcacccat cagggcctga gctcgcccgt cacaaagagc ttcaacaggg        720
gagagtgtta ggcggccgca agcttggccg ccatggccca acttgtttat tgcagcttat        780
aatggttaca aataaagcaa tagcatcaca aatttcacaa ataaagcatt tttttcactg        840
cattctagtt gtggtttgtc caaactcatc aatgtatctt atcatgtctg gatcg             895
```

(18.5C $V_L$)

SEQ ID NO: 30

```
tccaggtcca ctgcacctcg gttctatcga ttggctagca ccatggagac agacacactc         60
ctgctatggg tactgctgct ctgggttcca ggttccactg gtgacgacat ccagatgacc        120
cagtctccag gcaccctgtc tttgtctcca ggggaaagag ccaccctctc ctgcagggcc        180
agtcagagtg ttatcagtta ctacgtagcc tggtaccagc acaaaggtgg ccaggctccc        240
aggctcctca tttatggtgc atccagcagg gccactggcg tcccagacag gttcagtggc        300
agtgggtctg ggacagactt cactctcacc atcagcagcc tggagcctga agattttgca        360
ctgtattact gtcagtacta tgggagctca cctctgtggg cgttcggcca agggaccaag        420
gtggaaatca aacgaactgt ggctgcacca tctgtcttca tcttcccgcc atctgatgag        480
cagttgaaat ctggaactgc ctctgttgtg tgcctgctga ataacttcta tcccagagag        540
gccaaagtac agtggaaggt ggataacgcc ctccaatcgg gtaactccca ggagagtgtc        600
acagagcagg acagcaagga cagcacctac agcctcagca gcaccctgac gctgagcaaa        660
gcagactacg agaaacacaa agtctacgcc tgcgaagtca cccatcaggg cctgagctcg        720
cccgtcacaa agagcttcaa caggggagag tgttaggcgg ccgcaagctt ggccgccatg        780
gccc                                                                     784
```

(8.11G $V_L$)

SEQ ID NO: 31

```
cggttctatc gattggctag caccatggag acagacacac tcctgctatg ggtactgctg         60
ctctgggttc caggttccac tggtgacgaa attgtgctga ctcagtctcc agccaccctg        120
tctgtgtctc caggggggtag ggcctccctc tcctgccggg ccagtcagag tattggcgac       180
aagttatcct ggtatcagca gaaacctggg caggctccca ggctcgtcat ctatggtgca        240
tataccaggg ccactgatat ctcacccagg ttcagtggca gtaggtctgg gacagacttc        300
aatctcacca tcagcagaat gcagtctgga gactttgcag tttatttctg tcagcagtat        360
gaaaactggc ctcggacttt tggccagggg accaagctgg agatcaaacg aactgtggct        420
gcaccatctg tcttcatctt cccgccatct gatgagcagt tgaaatctgg aactgcctct        480
gttgtgtgcc tgctgaataa cttctatccc agagaggcca aagtacagtg gaaggtggat        540
aacgccctcc aatcgggtaa ctcccaggag agtgtcacag agcaggacag caaggacagc        600
acctacagcc tcagcagcac cctgacgctg agcaaagcag actacgagaa acacaaagtc        660
tacgcctgcg aagtcaccca tcagggcctg agctcgcccg tcacaaagag cttcaacagg        720
ggagagtgtt aggcggccgc aagcttggcc gccatggccc aacttgttta ttgcagctta        780
```

-continued

```
taatggttac aaataaagca atagcatcac aaatttcaca aataaagcat ttttttcact        840

gcatt                                                                    845
```

(25.10C $V_L$)

```
                                                            SEQ ID NO: 32
cctcggttct atcgattggc tagcaccatg gagacagaca cactcctgct atgggtactg         60

ctgctctggg ttccaggttc cactggtgac gacatccaga tgacccagtc tccatcctcc        120

ctgtctgcat ctgttggaga cagagtcatc atcacttgcc gggcaagtca gagcatcagc        180

agctctttaa attggtatca gcagaaacca gggaaagccc ctaagctcct gatctatgct        240

gcagtcaatt tggagactgg ggtcccgtca aggttcagtg gcagtggatt tgggacagat        300

ttcactctcg ccatcagcaa tgtgcaacct gaagattttg caacttacta ctgtcaacag        360

agcgatactc ggacttttgg ccgggggacc aagctggacg tcaaacgaac tgtggctgca        420

ccatctgtct tcatcttccc gccatctgat gagcagttga aatctggaac tgcctctgtt        480

gtgtgcctgc tgaataactt ctatcccaga gaggccaaag tacagtggaa ggtggataac        540

gccctccaat cgggtaactc ccaggagagt gtcacagagc aggacagcaa ggacagcacc        600

tacagcctca gcagcaccct gacgctgagc aaagcagact acgagaaaca caaagtctac        660

gcctgcgaag tcacccatca gggcctgagc tcgcccgtca caaagagctt caacagggga        720

gaagtgttag gcggccgcaa gcttggccgc catggcccaa cttgtttatt gcagcttata        780

atggttacaa ataaagcaat agcatcacaa atttcacaaa taaagcattt ttttcactgc        840

attctagttg tggtttgtcc aaactcatca atgtatctta tcatgtctgg atcgggaatt        900
```

Antibody Amino Acid Sequences

The $V_H$ and $V_L$ amino acid sequences of the antibodies and complementarity determining regions (CDR) of the $V_H$ and $V_L$ sequences are shown and discussed below.

(10.4B $V_H$)

```
                                             SEQ ID NO: 33
METDTLLLWVLLLWVPGSTGDQVQLVQSGGGVVQPGRSLRVSCVISGFNF

RAYGMHWVRQIPGKGLEWVADIWSAETNRHYADSVKGRFTISRDNSKSTL

YLQMNSIRAEDIGVYFCAKARPGYDYVVDLWGQGTLVIVSSASTKGPSVF

PLAPCSRSTSGGTAPLLGCLVKDYFPEPVTVSWNSGALTSGVHTFPAVLQ

SSGL
```

(19.7E $V_H$)

```
                                             SEQ ID NO: 34
METDTLLLWVLLLWVPGSTGDEVQLVESGGGIVRPGGSLRLSCAASGYSF

ESYSMHWVREVPGKGINWVSYINSDGSTKIYADSVKGRFSISRDNAKNKL

YLQMDSLRVEDTAVYSCVRLVHYDWSPFVWGQGTLVTVSSASTKGPSVFP

LAPSSKSTSGGTAALGCLVKDYFPEPVTVSWNSGALTSGVHTFPAVLQSS

GLYSLSSVVTVPSSSLGTQTYICNVNHKPSNTKVDKKVEPQSCDKTHTCP

PCPAPELL
```

(2.9D $V_H$)

```
                                             SEQ ID NO: 35
METDTLLLWVLLLWVPGSTGDEVQLVESGGGLVKPGGSLRLSCAASGFTF

TRFTLTWVRQAPGKGLEWVSSISSGSSDINYADSVKGRFTISRDNARNSL

FLQMSSLRVDDTAVYYCAKDPRSGISGRYGMDVWGQGTTVIVSSASTKGP

SVFPLAPCSRSTSGGIAALGCLVKDYFPEPVTVEWNSGALTSGVHTYPAV
```

-continued

```
LQSSGLYSLSSVVTVPSSSLGTQTYICNVNHKPSNTKVDKRVEPKSCDKT

HTCPPCPAPELLGGPSVFLFPPKPKDTLMISRIPEVTCVVVDVS
```

(25.6A $V_H$)

```
                                             SEQ ID NO: 36
METDTLLLWVLLLWVPGSTGDQVQLQESGGGLVKAGGSLRLSCAASGFMF

ERYSLHWVRQTPGKGLEWVSSISSLSGSHINYADSVKGRFTISRDNAKNS

LSLQMNSLBVEDTAIYYCARDRRSGSSPVPLDVWGQGTTVTVSSASTKGP

SVFPLAPSSKSTSGGTAALGC
```

(36.1F $V_H$)

```
                                             SEQ ID NO: 37
METDTLLLWVLLLWVPGSTGDQVQLQESGAGIVKPSETLSLTCAVSGGPF

SGAYWTWIRQTPGKGLEWIGEAGRSGTTNYNPSLKSRVTISLDISKSQFS

LKLTSVTAADTAVYFCGRRQIMSLSNLYKRPVDSWGRGTPVIVSSASTKG

PSVFPLAPSSKSTSGGTAALGCLVKDYFPEPVTVSWNSGALTSGVHTYPA

VLQSSGLYSLSSVVTVPSSSLGTQTYICNVNHKPSNTKVDKRVEPKSCDK

THTCPPCPAPELLGGPSVFLFPPX
```

(36.9F $V_H$)

```
                                             SEQ ID NO: 38
METDTLLLTWVLLLWVPGSTGDEVQLVQSGGGLVKAGGSLKLSCGASGFT

FSSYSMSWVRQAPGKGLEWVSYISSGGSSIHYADSVKGRFTISRDNAKNS

LYLQMKNLRVDDTGRYYCVRDPRSGISGRYGMDVWGQGTTVTVSSASTKG

PSVFPLAPSSKSTSGGTAALGCLVKDYFPEPVTVSWNSGALTSGVETFPA
```

-continued

VLQSSGLYSLSSVVTVPSSSLGTQTYICNVNHKPSNTKVDKRVEPKSCDK
THTCPPCDAPELLGGPSVFLPPNPRTPS*S (37.2D $V_H$)

SEQ ID NO: 39

METDTLLLWVLLLWVPGSTGDEVQLVQSGAEVKKPGASVKVSCKASGYTF
TKYGISWVRQAPGQGLEWMGWISAFNGYTRYGQRFQGKVTMTTDTSTNTA
SLEVRTLTSNDTAVYYCARQYPDQYSSSGWPRIFAMDVWGQGTTVIVSPA
STKGPSVFPLAPSSKSTSGGTAALGCLVKDYFPEPVTVEWNSGALTSGVH
TFPAVLQSSGLYSLSSVVTVPSSSLGTQTYICNVNHKPSNTKVDKRVEPK
SCDKTHTCPPCPAPELLGGPSVFLF (37.2G $V_H$)

SEQ ID NO: 40

METDTLLLWVLLLWVPGSTGDEVQLVESGGGLVKPGGSRRLSCAASGFTF
SRDTMTWVRQAPGKGLEWVASISSGSSDINYADSVKGRFTISRDNGKNSL
YLHMNSLRADDTAIYYCARDPRSGISGRYGMDVWGQGTTVTVSSASTKGP
SVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKT
HTCPPCPAPELLGGPSVFLFPPKPKDTLMISRTPEVTCVVVDVSHEDPEV
KFNWYVDGV (37.7H $V_H$)

SEQ ID NO: 41

METDTLLLWVLLLWVPGSTGDEVQLVQSGGGLVKAGGSLRLSCAASGFTF
STYSMNWIRQAPGKGLEWVASISSRSGSHINYVDSVKGRFTISRDNARDL
LYLQMNSLRVDDSALYYCARDRRSGTSPLPLDVWGQGTTVTVFSASTKGP
SVFPLAPSSKSTSGGTAALGCLVKDYFPEPVTVSWNSGALTSGVHTFPAV
LQSSGLYSLSSVVTVPSSSLGTQTYICNVNHKPSNTKVDKRVEPKSCDKT
HTCPPCPAPELLGGPSVFLFPPKPKDTLMISRTPEVTCVVVDVSHE (8.9F $V_H$)

SEQ ID NO: 42

METDTLLLWVLLLWVPGSTGDQGTLRESGPGLVRPSETLSLTCGVSGYSI
SSGYYNGWIRQPPGKGLEWIGNIYRSGSTYYNPSLKERVTVSIDTSKNQF
SLKLNSVTAADTAVYYCARSGIKVADDYYYEMDVWGQGTDDYSYAMDVWG
QGTTVTVSSASTKGPSVFPLAPSSKSTSGGTAALGCLVKDYETEPVTVSW
NSGALTSGVHTFPAVLQSSGLYSLSSVVTVPSSSLGTQTYICNVNHKPSN
TKVDKRVEPKSCDKTHTCPPCPAPELLGGPSVFLFPPKPKDTLMX (NE13 $V_H$)

SEQ ID NO: 43

METDTLLLWVLLLWVPGSTGDEVQLVESGGGLVKPGGSLRLSCVASGFTF
SSYSMNWVRQAPGKGLEWVSSISSGSSYIEYADSVKGRLTISRDNAKKSL
YLQLNSLRAEDTAVYYCARHTARIDSYHGMDVWGQGTTVTVSSASTKGPS
VFPLAPSSKSTSGGTAALGCLVKDYFPEPVTVSWNSGALTSGVHTFPAVL
QSSGLYSLSSVVTVPSSSLGTQTYICNVNHKPSNIKVDKRVEPKSCDKTH
TCPPCPAPELLGGPSVFLFPPKPKDTLMISRTP (12.1F $V_H$)

SEQ ID NO: 44

METDTLLLWVLLLWVPGSTGDQVQLQESGAGLLKPSETLSLSCTVDGESF

-continued

NGFFWTWIRQPPGKGLEWIGEINHLASTGYNPSLKSRVTISVDTSKNQFS
LKLTSVTAADTAVYYCARGYSYCFAWPNYHYLDVWGKGTTVTVSSASTKG
PSVFPLAPSSKSTSGGTAALGCLVKDYYPEPVTVWNSGALTSGVHTFPAV
ILQSSGLYSLSSVVTVPSSSLGTQTYICNVNHKPSNTKVDKRVEPKSCDK
THTCPPCPAPELLGGPSVFLXDPKPKDTLMISRTPEVTCVVVDVS (9.8A $V_H$)

SEQ ID NO: 45

METDTDLLLWVLLLWVPGSTGDEVQLVQSGGRLVQPGGSLRLSCVASGFT
FSSHAMSWVRQAPGKGLEWVSGFSGSSGTIKYADSVKGRFTISRDNSKKT
LYLQMNSLRAEDTAVYYCAKGFSPFRGVQFPYFDYWGQGTLVTVSSASTK
GPSVFPLAPSSKSTSGGTAALGCLVKDYTPEPVTVSWNSGALTSGVHTFP
AVLQSSGLYSLSSVVTVPSSSLGTQTYICNVNHKPSNTKVDKRVEPKSCD
KTHTCPPCPAPELLGGPSVFLFDPKPRIPS*SPGP (18.5C $V_H$)

SEQ ID NO: 46

METDTMLLWVLLLWVPGSTGDRVQLVESGGCLVRPGGSLRLSCAAAGFTF
KSYSMNWVRQAPGRGLEWVSSITSGGSKTYYADVVKGRFTVSRDNAKQSL
YLQMNSLRAEDTAIYFCARSLHSTSQPSYMDVWGRKITVIVSSASTKGPS
VFPLAPSSKSTSGGTAALGCLVKDYFPEPVTVSWNSGALTSGVHTFPAVL
QSSGLYSLSSVVTVPSSSLGTQTYICNVNHKPSNTKVDKRVEPKSCDKTH
TCPPCPAPELLGGPSVFLFPPKPKDTLMISRTPRVTC (8.11G $V_H$)

SEQ ID NO: 47

METDTLLLWVLLLWVPGSTGDQVQLQESGPGLVKPSETLSLTCSISGVST
RNYYWSWIRQSPGKGLEWIGYIFNIGTTNYNPSLKSRLTISVDTSKNQFS
LKITSVTAADTAVYYCASGFEYGDYTFDYWGQGTPVTVSSASTKGPSVET
LAPSSKSTSGGTAALGCLVKDYFPEPVTVEWNSGALTSGVHTYPAVLQSS
GLYSLSSVVTVPSSSLGTQTYICNVNHKPSNTKVDKRVEPKSCDKTHTCP
PCPAPELLGGPSVFLFPPKPKDTLMIFRTPEVTCVVVDVS (25.10C $V_H$)

SEQ ID NO: 48

METDTLLLWVLLLWVPGSTGDTQLQESGGGLVKPGGSLRLSCTASGFNFN
KYNKNWVRQAPGKGLEWVSSISALSTYIYYADSLKGRFTVSRDNAKNSLF
LQMNSLRDDDTAVYYCAREIRRASTWSADLWGRGTLVTVSSASTKGPSVF
PLAPSSKSTSGGTAALGCLVKDYFPEPVTVSWNSGALTSGVHTFPAVLQS
SGLYSLSSVVTVPSSSLGTQTYICNVNHKPSNTKVDKRVEPKSCDKTHTC
PPCPAPELLGGPSVFLFPPNPRTPS (10.4B $V_L$)

SEQ ID NO: 49

METDTLLLWVLLLWVPGSTGDEIVLTQSPSSLSASVGDRVTITCRASRDI
NTYLGWFQQRPGKAPKSLIYGASNLQNGVPSRFSGSGSGTYFTLTINGLQ
TEDFATYYCQQYSIYPLSLGGGTKADMKRTVAAPSVFIFPPSDEQLKEGT
ASVVCLLNNFYPREAKVQWKVDNALQSGNSQESVTEQDSKDSTYSLSSTL
TLSKADYFKHKVYACEVTHQGLSSP (19.7E $V_L$)

SEQ ID NO: 50

METDTLLLWLLLLWVPGSTGDEIVLTQPSTLSASVGDRVTITCRASQSIN

-continued

NWLAWYQEKPGKAPKLLINKASSLESGVPSRFSGSGSGTEFTLTITSLQP
DDFATYYCQQYNSNSWTFGQGTKVDMKRTVAAPSVFIFPPSDEQLKSGTA
SVVCLLNNFYPREAKVQWKVDNALQSGNESQESVTEQSKDSTYSLSSTLT
LSKADYEKHKVYACEVTHQGLSSPVTKSFNRGEC (2.9D $V_L$)

SEQ ID NO: 51
MKTDTLLLWVLLLWVPGSTGDDIVLTQSPDSLAVSLGERATINCKSSQSV
LYSSNNKNYLAWYQQKPGQPPKLLIYWASTRESGVPDRFSGSGSGTDFTL
TISSLQAEDVAVYYCQQYYSTPPTFGQGTKVEIKRTVAAPSVFIFPPSDE
QLKSGTASVVCLLNNTYPREAKVQWKVDNALQSGNSQESVTFQDSKDSTY
SLSSTLTLSKADYEKHKVYACEVTHQGLSSPVTKSFNRGEC (25.6A $V_L$)

SEQ ID NO: 52
METDTLLLWVLLLWVPGSTGDLPVLTQPASVSGSPGQSITISCTGTSSDV
GAYNYVSWYQQHPGKAPKLIIYEVKIRPSGVSNRFSGSKSGNTASLTISG
LQAEDEADYFCSSYSTNSPWVFCGGTKVTVLRQPKAAPSVTLFPPSSEEL
QANKATLVCLISDFYPCAVTVAWKADSSPVKAGVETTTPSKQSNNKYAAS
SYLSLTPEQWKSHRSYSCQVTHEGSTVEKTVAPTECS*

(36.1F $V_L$)

SEQ ID NO: 53
METDTLLLWVLLLWVPGSTGDEIVLTQSPGTLSLSPGERATLSCRASQSV
TKNYLAWYQQKPGQAPTLVIYDASTRASGIPDRFIGSGSGTDFTLTISRL
EPEDFAVYYCHQYGSSPPYTFGRGTKLEIKRTVAAPSVFIFPPSDEQLKS
GTASVVCLLNNEYPREAKVQWKVDNALQSGNSQESVTEQDSKDSTYSLSS
TLTLSKADYEKHKVYACEVTHQGLSSPVTKSFNRGEC*

(36.9F $V_L$)

SEQ ID NO: 54
METDTLLLWVLLLWVPGSTGDDIVMTQSPDSLAVSLGERATINCKSSQTV
LFTSYYVAWYQQKPGQPPKLLFSGASSRESGVPDRESAGGSGTDFYLTIN
SLQAEDVADYYCQQYHTPPFTFGGGTKLEIRRTVAAPSVFIFPPSDEQLK
SGTASVVCLLNNFYPREAKVQWKVDNALQSGNSQESVTEQDSKDSTYSLS
SILTLSKADYEKHKVYACEVTHQGLSSPVTKEFNRGEC*

(37.2D $V_L$)

SEQ ID NO: 55
METDTLLLWVLLLWVPGSTGDETTLTQSPATLSVSPGETATISCRASQNV
INNLAWYQQKPGQAPRLLIYGASTRATGIPARFSGSGSGTEFTLTISSMQ
SEDFAVYYCQQYNDWPRSFGQGTRLDIRRTVAAPSVFIFPPSDEQLKSGT
ASVVCLLNNEYPREAKVQWKVDNALQSGNSQESVTEQDSKDSTYSLSSTL
TLSKADYEKHKVYACEVTHQGLSSPVTKSFNRGEC*

(37.2G $V_L$)

SEQ ID NO: 56
METDTLLLWLLLWVPGSTGDDIVLTQSPGTLSLSPGERATLSCRASQSVN
SIFLAWYQQKPGQAPRLLIYGASSRATGIPDRFSGSGSGTDFTLTISRLE
PEDFAVYYCQQYHSSPKLTFGGGTKVEIKRTVAAPSVFIFPPSGEQLKSG
TASVVCLLNNFYPREAKVQWKVDNALQSGNSQESVTEQDSKDSTYSLSST
LTLSKADYEKHKVYACEVTHQGLSSPVTKSFNRGEC*

-continued (37.7H $V_L$)

SEQ ID NO: 57
METDTLLLWVLLLWVPGSTGDQSALTQPASVSGSPGQSITISCTGTGSDI
GGYNFVSWYQQYPGKAPKLIIYEVRIRASGVSNRFSGSKSGNTASLTISG
LQAEDEADYYCNSYSIHSPWVFGGGTKLTVLRQPKAAPSVTLFPPSSEEL
QANKATLVCLISDFYPGAVTVAWKADSSPVKAGVETTTPSKQSNNKYAAS
SYLSLTPEQWESHRSYSCQVTHEGSTVEKTVAPTECS*

(8.9F $V_L$)

SEQ ID NO: 58
METDTLLLWVLLLWVPGSTGDQAGLTQPASVSGSPGQSITISCTAANSDI
GDFNFVSWYQQRPDKAPKLMVYEVSSRPSGVSNRFSGSKSGNTASLTISG
LQAEDEADYYCTSYTSSSTFVFGTGTKVTVLGQPKANPTVTLFPPSSEEL
QANKATLVCLISDFYPGAVTVAWKADSSPVKAGVETTTPSKQSNNKYAAS
SYLSLTPEQWKSHRSYSCQVTHEGSTVEKTVAPTECS*

(NE13 $V_L$)

SEQ ID NO: 59
TMETDTLLLWVLLLWVPGSTGDETTLTQSPGTLSLSPGERATLSCRASQS
VSSTYLAWYQQKPGQSPRLLIYGASSRATGIPDRFSGSGSGTQFTLTINR
LEPEDFAVYYCQQFGSPWTFGQGTKVEIKRTVAAPSVFIFPPSDEQLKSG
TASVVCLLNNEYPREAKVQWKVDNALQSGNSQESVTEQDSKDSTYSLSST
LTLSKADYEKHKVYACEVTHQGLSSPVTKSFNRGEC*

(12.1F $V_L$)

SEQ ID NO: 60
METDTLLLWVLLLWVPGSTGDETTLTQSPATLSLSPGERATLSCRASQSV
SSYLAWYQHKPGQAPRLLIYGASKRATGIPSRFSGSGSGTDFSLTISSLE
PEDFAVYYCQHRSDWRTTFGQGTRLEIKRTVAAPSVFIFPPSDEQLKSGT
ASVVCLLNNFYPREAKVQWKVDNALQSGNSQESVTEQDSKDSTYSLSSTL
TLSKADYEKHKVYACEVTHQGLSSPVTKSFKRGEC*

(9.8A $V_L$)

SEQ ID NO: 61
METDTLLLWVLLLWVPGSTGDDIVMTQSPSTLSASVGDRVTITCRASQSI
DRWLAWYQQKPGKAPKLLIYQASSLERGVPSRFSGSGSGTEFTLTISSLQ
PDDFATYYCQQYNGYPLTFGGGTKVEIKRTVAAPSVFIFPPSDEQLKSGT
ASVVCLLNNFYPREAKVQWKVDNALQSGNSQESVTEQDSKDSTYSLSSTL
TLSKADYEKHKVYACEVTHQGLSSPVTKSEFRGEC*

(18.5C $V_L$)

SEQ ID NO: 62
METDTLLLWVLLLWVPGSTGDDIQMTQSPGTLSLSPGERATLSCRASQSV
ISYYVAWYQHKGGQAPRLLIYGASSRATGVPDRFSGSGSGTDFTLTISSL
EPEDFALYYCQYYGSSPLWAFGQGTKVEIKRTVAAPSVFIFPPSDEQLKS
GTASVVCLLNNFYPREAKVQWKVDNALQSGNSQESV7EQDSKD5TYSLSS
TLTLSKADYEKHKVYACEVTHQGLSSPVTKSFNRGEC*

(8.11G $V_L$)

SEQ ID NO: 63
METDTLLLWVLLLWVPGSTGDEIVLTQSPATLSVSPGGRASLSCRASQSI
GDKLSWYQQKPGQAPRLVIYGAYTRATDISPRFSGSRSGTDFNLTISRMQ

-continued

SGDFAVYFCQQYENWPRTFGQGTKLEIKRTVAAPSVFIFPPSDEQLKSGT

ASVVCLLNNFYPREAKVQWKVDNALQSGNSQESVTEQDSKDSTYSLSSTL

TLSKADYEKHKVYACEVTHQGLSSPVTKSFNRGEC*

(25.10C $V_L$)

SEQ ID NO: 64

METDTLLLWVLLLWVPGSTGDDIQMTQSPSSLSASVGDRVIITCRASQSI

SSSLNWYQQKPGKAPKLLIYAAVNLETGVPSRFSGSGFGTDFTLAISNVQ

PEDFATTYCQQSDTRTFGRGTKLDVKRTVAAPSVFIFPPSDEQLKSGTAS

VVCLLNNFYPREAKVQWKVDNAIQSGNSQESVTEQDSKDSTYSLSSTLTL

SKADYEKHKVYACEVTHQGLSSPVIKSENRGEVLGGRKLGBEGPTCLLQL

TMVTNKAIASQISQIKHFFHCILVVVCPNSSMYLIMSGSGI

FIG. 7 provides a sequence alignment prepared using CLUSTAL OMEGA™ (1.2.4) multiple sequence alignment (from EMBL-EBI, a part of the European Molecular Biology Laboratory) for the heavy chain variable region amino acid sequences, with CDRs highlighted in bold typeface: CDR1 (marked with +), CDR 2 (marked with ^), and CDR3 (marked with #).

FIG. 8 provides a sequence alignment prepared using CLUSTAL OMEGA™ (1.2.4) multiple sequence alignment for the light chain variable region amino acid sequences, with CDRs highlighted in bold typeface: CDR1 (marked with +), CDR 2 (marked with ^), and CDR3 (marked with #).

The HC CDR Sequence Table below lists the sequences of CDR1, CDR 2, and CDR3 of the $V_H$ of each of the 16 neutralizing antibodies described herein. The LC CDR Sequence Table below lists the sequences of CDR1, CDR 2, and CDR3 of the $V_L$ of each of the 16 neutralizing antibodies described herein.

HC CDR Sequence Table.

| Antibody | HC CDR1 | HC CDR2 | HC CDR3 |
|---|---|---|---|
| 10.4B | GFNFRAYG (SEQ ID NO: 65) | IWSAETNRH (SEQ ID NO: 66) | AKARPGYDYVVDL (SEQ ID NO: 67) |
| 19.7E | GFSFSSYS (SEQ ID NO: 68) | INSDGSTKI (SEQ ID NO: 69) | VRLVHYDWSPFV (SEQ ID NO: 70) |
| 2.9D | GFTFTRFT (SEQ ID NO: 71) | ISSGSSDIN (SEQ ID NO: 72) | AKDPRSGISGRYGMDV (SEQ ID NO: 73) |
| 25.6A | GFMFERYS (SEQ ID NO: 74) | ISSLSGSHIN (SEQ ID NO: 75) | ARDRRSGSSPVPLDV (SEQ ID NO: 76) |
| 36.1F | GGPFSGAY (SEQ ID NO: 77) | AGRSGTTN (SEQ ID NO: 78) | GRRQIMSLSNLYKRPVDS (SEQ ID NO: 79) |
| 36.9F | GFTFSSYS (SEQ ID NO: 80) | ISSGGSSIH (SEQ ID NO: 81) | VRDPRSGISGRYGMDV (SEQ ID NO: 82) |
| 37.2D | GYTFTKYG (SEQ ID NO: 83) | ISAFNGYTR (SEQ ID NO: 84) | ARQYPDQYSSSGWPRLFAMDV (SEQ ID NO: 85) |
| 37.2G | GFTFSRDT (SEQ ID NO: 86) | ISSGSSDIN (SEQ ID NO: 87) | ARDPRSGISGRYGMDV (SEQ ID NO: 88) |
| 37.7H | GFTFSTYS (SEQ ID NO: 89) | ISSRSGSHIN (SEQ ID NO: 90) | ARDRRSGTSPLPLDV (SEQ ID NO: 91) |
| 8.9F | GYSISSGYY (SEQ ID NO: 92) | IYRSGSTY (SEQ ID NO: 93) | ARSGIKVADDYYYEMD VWGQGTDDYSYAMDV (SEQ ID NO: 94) |
| NE13 | GFTFSSYS (SEQ ID NO: 95) | ISSGSSYIE (SEQ ID NO: 96) | ARHTARIDSYHGMDV (SEQ ID NO: 97) |
| 12.1F | GESFNGFF (SEQ ID NO: 98) | INHLASTG (SEQ ID NO: 99) | ARGYSYGFAWPNYHYLDV (SEQ ID NO: 100) |
| 9.8A | GFTFSSHA (SEQ ID NO: 101) | FSGSSGTTK (SEQ ID NO: 102) | AKGFSPFRGVQFPYFDY (SEQ ID NO: 103) |
| 18.5C | GFTFKSYS (SEQ ID NO: 104) | ITSGGSKTY (SEQ ID NO: 105) | ARSLHSTSQPSYMDV (SEQ ID NO: 106) |
| 8.11G | GVSTRNYY (SEQ ID NO: 107) | IFNIGTTN (SEQ ID NO: 108) | ASGFEYGDYTFDY (SEQ ID NO: 109) |
| 25.10C | GFNFNKYN (SEQ ID NO: 110) | ISALSTYIY (SEQ ID NO: 111) | AREIRRASTWSADL (SEQ ID NO: 112) |

LC CDR Sequence Table.

| Antibody | LC CDR1 | LC CDR2 | LC CDR3 |
|---|---|---|---|
| 10.4B | RDINTY (SEQ ID NO: 113) | GAS | QQYSIYPLS (SEQ ID NO: 114) |
| 19.7E | QSINNW (SEQ ID NO: 115) | KAS | QQYNSNSWT (SEQ ID NO: 116) |
| 2.9D | QSVLYSSNNKNY (SEQ ID NO: 117) | WAS | QQYYSTPPT (SEQ ID NO: 118 |
| 25.6A | SSDVGAYNY (SEQ ID NO: 119) | EVK | SSYSTNSPWV (SEQ ID NO: 120) |
| 36.1F | QSVTKNY (SEQ ID NO: 121) | DAS | HQYGSSPPYT (SEQ ID NO: 122) |
| 36.9F | QTVLFTSYY (SEQ ID NO: 123) | GAS | QQYHTPPFT (SEQ ID NO: 124) |
| 37.2D | QNVINN (SEQ ID NO: 125) | GAS | QQYNDWPRS (SEQ ID NO: 126) |
| 37.2G | QSVNSIF (SEQ ID NO: 127 | GAS | QQYHSSPKLT (SEQ ID NO: 128) |
| 37.7H | GSDIGGYNF (SEQ ID NO: 129) | EVR | NSYSIHSPWV (SEQ ID NO: 130) |
| 8.9F | NSDIGDFNF (SEQ ID NO: 131) | EVS | TSYTSSSTFV (SEQ ID NO: 132) |
| NE13 | QSVSSTY (SEQ ID NO: 133) | GAS | QQFGSPWT (SEQ ID NO: 134) |
| 12.1F | QSVSSY (SEQ ID NO: 135) | GAS | QHRSDWRTT (SEQ ID NO: 136) |
| 9.8A | QSIDRW (SEQ ID NO: 137) | QAS | QQYNGYPLT (SEQ ID NO: 138) |
| 18.5C | QSVISYY (SEQ ID NO: 139) | GAS | QYYGSSPLWA (SEQ ID NO: 140) |
| 8.11G | QSIGDK (SEQ ID NO: 141) | GAY | QQYENWPRT (SEQ ID NO: 142) |
| 25.10C | QSISSS (SEQ ID NO: 143) | AAV | QQSDTRT (SEQ ID NO: 144) |

Diagnostics

The antibodies described herein may be used in a variety of immunoassays for LASV, LCMV, and other arenaviruses. The antibodies of the invention can be produced with high quality control and are suitable as reagents for the purposes of detecting antigen in biological samples. By way of example and not limitation, antibodies of the invention could be used as reagents in an ELISA assay to detect Lassa antigen in a biological sample from a subject. The antibodies can be labeled, e.g., bound to a detectable labelling group such as a fluorescent dye, a quantum dot label, R-phycoerythrin, streptavidin, biotin, an enzyme, a radioisotope, and the like. Such labelling techniques are well known in the antibody art.

Vaccines

Vaccines for LASV, LCMV, and other arenaviruses also are described herein. In one aspect the vaccines are DNA-based vaccines. One skilled in the art is familiar with administration of expression vectors to obtain expression of an exogenous protein in vivo. See, e.g., U.S. Pat. Nos. 6,436,908; 6,413,942; and 6,376,471. Viral-based vectors for delivery of a desired polynucleotide and expression in a desired cell are well known in the art and non-limiting examples are described herein.

Administration of expression vectors includes local or systemic administration, including injection, oral administration, particle gun or catheterized administration, and topical administration. Targeted delivery of therapeutic compositions containing an expression vector or subgenomic polynucleotides can also be used. Receptor-mediated DNA delivery techniques are described in, for example, Findeis et al., *Trends Biotechnol.* (1993) 11:202; Chiou et al., *Gene Therapeutics: Methods And Applications Of Direct Gene Transfer* (J. A. Wolff, ed.) (1994); Wu et al., *J. Biol. Chem.* (1988) 263:621; Wu et al., *J. Biol. Chem.* (1994) 269:542; Zenke et al., *Proc. Natl. Acad. Sci. USA* (1990) 87:3655; Wu et al., *J. Biol. Chem.* (1991) 266:338.

Non-viral delivery vehicles and methods can also be employed, including but not limited to, polycationic condensed DNA linked or unlinked to killed adenovirus alone (see, e.g., Cunel, *Hum. Gene Ther.* (1992) 3:147); ligand-linked DNA (see, e.g., Wu, *J. Biol. Chem.* (1989) 264: 16985); eukaryotic cell delivery vehicles (see, e.g., U.S. Pat. No. 5,814,482; PCT Publication Nos. WO 95/07994; WO 96/17072; WO 95/30763; and WO 97/42338); and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796, WO 94/23697, WO 91/14445; and EP 0524968. Additional approaches are described in Philip, *Mol. Cell Biol.* (1994) 14:2411, and in Woffendin, *Proc. Natl. Acad. Sci.* (1994) 91:1581.

For human administration, the codons comprising the polynucleotide encoding one or more antibodies specific for LASV glycoprotein and/or LCMV glycoprotein may be optimized for human use, a process that is standard in the art.

In another aspect, one or more antibodies specific to LASV and/or LCMV or combinations thereof is used as a vaccine. The one or more antibodies or combination thereof may be administered by itself or in combination with an adjuvant. Examples of adjuvants include, but are not limited to, aluminum salts, water-in-soil emulsions, oil-in-water emulsions, saponin, QuilA and derivatives, iscoms, liposomes, cytokines including gamma-interferon or interleukin 12, DNA (e.g. unmethylated poly-CpG), microencapsulation in a solid or semi-solid particle, Freunds complete and incomplete adjuvant or active ingredients thereof including muramyl dipeptide and analogues, DEAE dextrarilmineral oil, Alhydrogel, Auspharm adjuvant, and Algammulin.

The antibody vaccine comprising one or more antibodies specific to LASV and/or LCMV or combinations thereof can be administered orally or by any parenteral route such as intravenously, subcutaneously, intraarterially, intramuscularly, intracardially, intraspinally, intrathoracically, intraperitoneally, intraventricularly, sublingually, and/or transdermally.

Dosage and schedule of administration can be determined by methods known in the art. Efficacy of the one or more antibodies specific to LASV and/or LCMV or combinations thereof as a vaccine for Lassa virus, lymphocytic choriomeningitis virus, or related arenaviruses may also be evaluated by methods known in the art.

Pharmaceutical Compositions

The polynucleotides, polypeptides, and antibodies described herein can further comprise pharmaceutically acceptable carriers, excipients, or stabilizers known in the art (*Remington: The Science and practice of Pharmacy* 20th Ed., 2000, Lippincott Williams and Wilkins, Ed. K. E.

Hoover), in the form of lyophilized formulations or aqueous solutions. Acceptable carriers, excipients, or stabilizers are non-toxic to recipients at the employed dosages and concentrations, and may comprise buffers such as phosphate, citrate, and other organic acids; antioxidants including ascorbic acid and methionine; preservatives (e.g. octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol, and m-cresol); low molecular weight (less than about 10 residues) polypeptides; proteins such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, marmose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Pharmaceutically acceptable excipients are further described herein.

The compositions used in the methods described herein generally comprise, by way of example and not limitation, an effective amount of a polynucleotide or polypeptide (e.g., an amount sufficient to induce an immune response) of the invention or antibody of the invention (e.g., an amount of a neutralizing antibody sufficient to mitigate infection, alleviate a symptom of infection and/or prevent infection).

The pharmaceutical composition can further comprise additional agents that serve to enhance and/or complement the desired effect. By way of example, to enhance the efficacy of the one or more antibodies specific to LASV and/or LCMV or combinations thereof administered as a pharmaceutical composition, the pharmaceutical composition may further comprise an adjuvant. Examples of adjuvants are provided herein.

Also by way of example and not limitation, if the one or more antibodies specific to LASV and/or LCMV or combinations thereof of the invention is being administered to augment the immune response in a subject infected with or suspected of being infected with LASV or LCMV and/or if antibodies of the present invention are being administered as a form of passive immunotherapy, the composition can further comprise other therapeutic agents (e.g., anti-viral agents).

Kits

Kits for use in the instant methods also are described. Kits include one or more containers comprising by way of example, and not limitation, polynucleotides encoding one or more antibodies specific to LASV and/or LCMV or combinations thereof or fragments thereof of the invention and instructions for use in accordance with any of the methods of the invention described herein. In some embodiments of the kit, the antibodies are bound to a detectable label as discussed above.

Generally, instructions comprise a description of administration or instructions for performance of an assay. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (e.g. the container may be an intravenous solution bag or a vial having a stopper pierceable by a hypodermic injection needle). The container may also have a sterile access port (e.g. the container may be an intravenous solution bag or a vial having a stopper pierceable by a hypodermic injection needle). Kits may optionally provide additional components such as buffers and interpretive information. Normally, the kit comprises a container and a label or package insert(s) on or associated with the container.

The following non-limiting examples are provided to illustrate certain aspects and features of the materials and methods described herein.

EXAMPLES

Example 1: LCMV Infection of the Mouse and Recombinant Arenaviruses are a Powerful Experimental System to Assess the Potency and Breath of LCMV Neutralizing mMAbs In Vivo Both host and viral factors, as well as route of infection and dose of virus influence the outcome of LCMV infection of the mouse. Thus, intravenous (i.v.) inoculation of adult immune competent mice with LCMV Armstrong (ARM) strain results in an acute infection that induces a protective immune response that mediates virus clearance in 10 to 14 days, a process predominantly mediated by virus-specific CD8+ cytotoxic T lymphocytes (CTL). In contrast, i.v. inoculation with a high dose of the immunosuppressive clone 13 (Cl-13) strain of LCMV causes a persistent infection associated with sustained viremia and generalized immune suppression that can last for 60 to 100 days. This model is robust and has clear outcomes, which provide a valid and cost effective experimental system for initial evaluation of the efficacy of antibody-based strategies to control and clear a LCMV infection. In this regard, the use of Cl-13 based recombinant viruses expressing GPs of interest allows assessment of the safety and in vivo neutralizing activity of GP-specific BNmMAbs. This approach is feasible using state-of-the-art arenavirus reverse genetics that allows rescue of infectious recombinant LCM viruses with predetermined mutations of interest, as well as expressing heterologous either viral or non-viral genes of interest. A single-cycle infectious, reporter expressing, recombinant LCMV in which the GP ORF is replaced by GFP (rLCMVΔGP/GFP) was generated. Genetic complementation with plasmids or stable cell lines expressing arenavirus GPs of interest produces the corresponding GP-pseudotyped rLCMVΔGP/GFP that can be used to evaluate antibody responses to HF arenaviruses using a BSL2 platform.

Example 2: Identification of LASV (Josiah Strain) GP-Specific hMAbs that Cross-React with the GP of LCMV ARM Strain Generation of LASV GP-specific hMAbs: Peripheral blood mononuclear cells (PBMCs) isolated from 17 different LF survivors in Sierra Leone and Nigeria were used to identify B cell clones producing specific IgG to LASV GP. RNA from these B cell clones was used to clone the light chain (LC) and heavy chain (HC) genes. Paired LC and HC were expressed in human 293T cells to generate a collection of 120 LASV GP-specific hMAbs. These hMAbs arose from different germline genes and were likely independently derived. All but one (8.9F) of the hMAbs reacted in ELISA with GP from Josiah strain of LASV (lineage IV), which is closely related to the currently circulating LASV strains in Sierra Leone. LASV GP consists of a SSP and GP1 and GP2 subunits, as shown in FIG. 1, Panels A and B. To define the GP subunits recognized by the LASV hMAbs, an immunofluorescence assay was used to test the recognition by hMAbs of human 293T cells expressing either rGP1 or rGP2 alone, or full-length GP, shown in FIG. 1, Panel C. Twenty-nine hMAbs, including three with neutralizing activity, reacted with LASV rGP1, shown by FIG. 1, Panel C, left and Table 1. Fifty-seven hMAbs recognized LASV rGP2 but none of these exhibited neutralizing activity, as shown by FIG. 1, Panel C, middle and Table 1. Seven hMAbs reacted with peptides representing three linear epitopes in GP2, whereas the remaining hMAbs appeared to recognize conformational epitopes. Twenty-seven hMAbs reacted with cells expressing full-length GP but did not react with either rGP1 or rGP2 expressed individually. Remarkably, thirteen of these hMAbs were neutralizing, as shown by FIG. 1, Panel C, right and Table 1. Inhibitory concentration 50 (IC50) and 80 (IC80) neutralizing activity of LASV GP-specific hMAbs was evaluated using lentivirus particles pseudotyped with the different lineage I-IV LASV GPs. Results are shown in Table 1. Based on the data in Table 1, the antibodies can be classified as most potent (hMAbs exhibiting IC values of <1 μg/mL); potent (hMAbs exhibiting IC values in the range of 1 to 2.5 μg/mL), weak (hMAbs exhibiting IC values of >3 and <20 μg/mL); non-neutralizing (hMAbs exhibiting IC values>20 μg/mL).

TABLE 1

Neutralizing activity of LASV GP-specific hMAbs against LASV lineages I-IV.

| | LASV Josiah (IV) | | LASV 237 (III) | | LASV A19 (II) | | LASV Pinneo(I) | |
|---|---|---|---|---|---|---|---|---|
| Mab | IC50 | IC80 | IC50 | IC80 | IC50 | IC80 | IC50 | IC80 |
| 25.10C | 0.094 | 0.174 | 0.058 | 0.180 | 0.104 | 0.364 | 0.226 | 0.564 |
| 12.1F | 0.158 | 0.562 | 0.146 | 0.458 | 0.463 | 2.266 | 0.285 | 0.692 |
| 8.9F | 0.126 | 1.604 | 0.182 | 3.097 | 0.125 | 0.467 | 0.403 | 2.210 |
| 37.2D | 0.559 | 1.983 | 0.256 | 0.844 | 0.469 | 1.154 | 0.537 | 1.861 |
| 37.7H | 0.191 | 0.532 | 0.077 | 0.202 | 0.255 | 0.537 | 0.301 | 1.658 |
| 25.6A | 0.743 | 1.999 | 0.169 | 0.603 | 0.483 | 3.509 | 1.826 | 3.114 |
| 9.8A | 1.309 | 2.423 | 0.193 | 0.494 | 0.150 | 0.527 | 1.003 | 2.587 |
| 18.5C | 1.935 | 3.985 | 0.621 | 3.231 | 1.200 | 4.633 | 6.111 | 12.170 |
| 8.11G | 0.361 | 1.736 | 1.166 | 3.637 | 1.481 | 4.591 | 3.245 | 10.540 |
| 37.2G | 5.599 | 16.000 | 2.020 | 5.231 | 1.100 | 10.000 | >20 | >20 |
| 2.9D | 6.895 | 16.700 | 1.582 | 5.511 | 3.072 | 14.780 | 10.130 | >20 |
| NE13 | 10.680 | 19.500 | 2.136 | 7.000 | 5.409 | 13.180 | >20 | >20 |
| 19.7E | 5.908 | >20 | 1.062 | 15.000 | >20 | >20 | 1.558 | 3.273 |
| 36.9F | 18.000 | >20 | 4.687 | 19.350 | 13.000 | >20 | 6.984 | >20 |
| 36.1F | 0.248 | 0.755 | >20 | >20 | >20 | >20 | >20 | >20 |
| 10.4B | >20 | >20 | >20 | >20 | >20 | >20 | >20 | >20 |

Neutralizing properties of LASV GP-specific hMAbs: The neutralizing properties of the LASV GP-specific hMAbs were evaluated using envelope-deficient core HIV-1 pseudotyped with LASV GP (LASVpp) (shown in Table 1) and standard plaque reduction neutralization test (PRNT) with authentic LASV. Fifteen of the 120 hMAbs neutralized LASVpp expressing GP from Josiah strain of LASV lineage IV, as shown in Table 1. These neutralizing GP-specific hMAbs were also tested against LASVpp containing GP of the three other LASV lineages I-III (shown in Table 1). The IC50 and IC80 values showed that those with the greatest potency and breadth against all four LASV linages were 25.10C, 12.1F, 8.9F, 37.2D, 37.7H, 25.6A and 8.11G (Table 1). The remaining hMAbs showed weaker and variable potency. Neutralization activity of these GP-specific hMAbs was further confirmed for LASV Josiah strain using a LCMV-based pseudovirus assay. These results revealed that out of the 120 tested LASV GP-specific hMAbs, 15 neutralized to different degrees LASV Josiah strain, and some of them exhibited broad neutralizing activity against representative strains from LASV lineages I-II.

Cross-reactivity of LASV GP-specific hMAbs with LCMV ARM: The 16 LASV GP-specific hMAbs with neutralizing activity (as shown in Table 1) were characterized with respect their ability to recognize LCMV ARM strain GP expressed in human 293T cells transfected with GP-expressing plasmids by immunofluorescence. Human 293T cells transfected with LASV GPs from linages I-IV were included as controls. Nine of the LASV GP-specific neutralizing hMAbs (12.1F, 37.7H, 37.2D, 25.6A, 9.8A, 18.5C, 37.2G, 2.9D and 36.9F) cross-reacted with LCMV ARM GP.

Example 3: Identification of LASV GP-Specific hMAbs with Broad Cross-Reactivity Against GPs from Different LCMV Strains The ability of LASV GP-specific neutralizing hMAbs (as shown by FIG. 1 and Table 1) to recognize GPs from five LCMV strains associated with human cases of LCMV-induced disease was examined. These strains corresponded to the WE strain that caused a zoonotic infection in New York in 1935; Rhode Island (RI) strain, responsible for four human cases and three fatalities from a transplant case in 2005; Ohio (OH) strain that is similar to the Michigan LCMV strain responsible for a human case in 2005; Wisconsin (WI) strain responsible for four human deaths in 2003; and Massachusetts (MA) strain, responsible for two human deaths in 2008. LASV GP-specific neutralizing hMAbs 12.1F, 37.2D, 9.8A, 18.5C and 36.9F recognized all five LCMV GP strains. LASV GP-specific neutralizing hMAbs 37.7H, 25.6A, 37.2G and 2.9D recognized four LCMV strains (ARM, WE, WI, and MA, but not RI or AH). The rest of the hMAbs did not cross-react with any of the LCMV strains tested.

Figure 2:
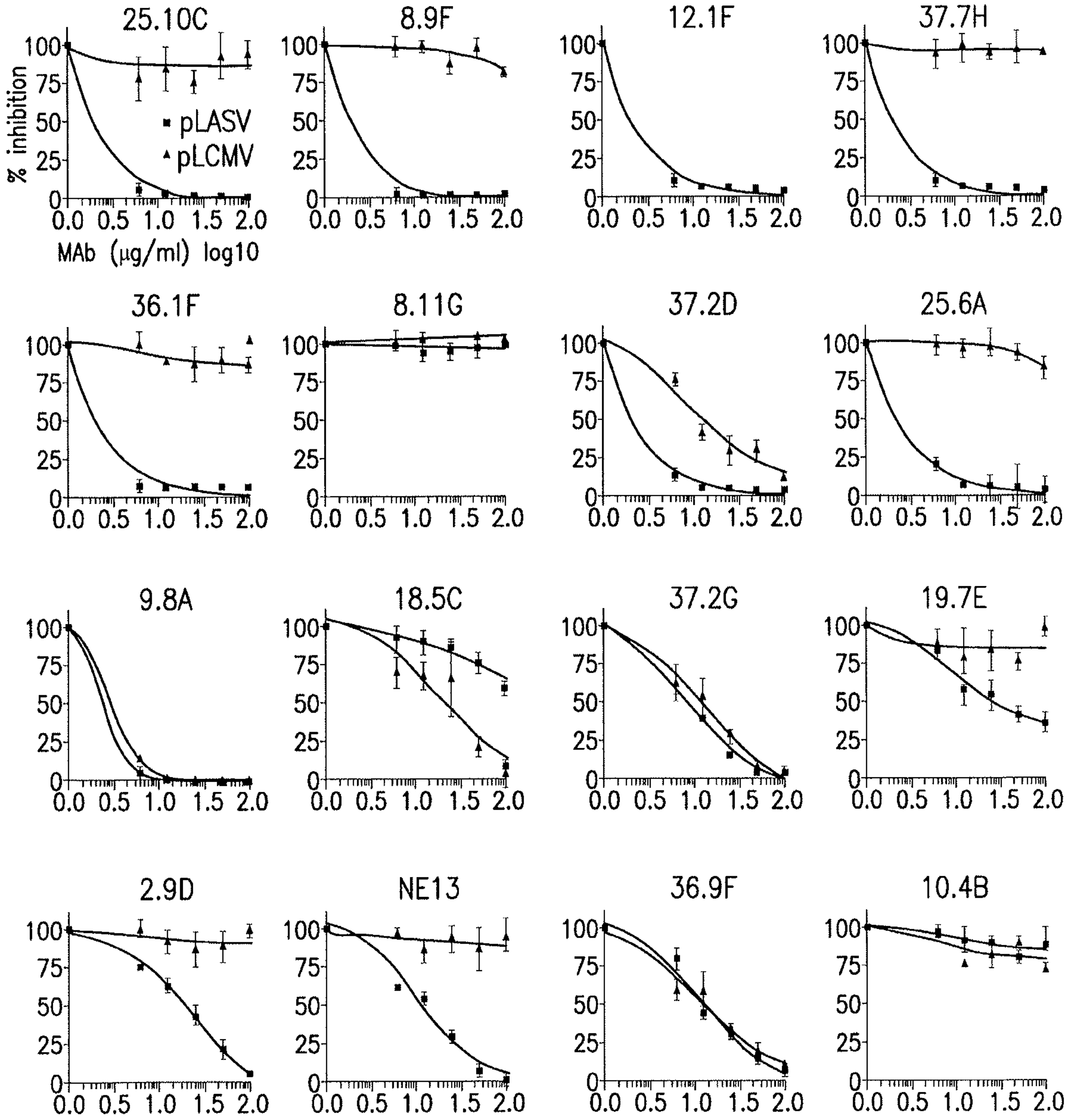
FIG. 2 depicts in vitro neutralization of LCMV ARM with the 15 LASV GP-specific neutralizing hMAbs: LASV Josiah (squares) and LCMV ARM (triangles) GP-pseudotyped rLCMVΔGP/GFP viruses were incubated for 90 min at 37° C. with a 2-fold dilution of the indicated LASV GP-specific BNhMAb before infecting LCMV GP-expressing Vero cells (96 plate format, triplicates). Virus neutralization was determined under a fluorescent microscope and quantified using a GFP microplate reader at 72 hours post-infection. Results are presented as percent inhibition after normalizing to respective viral infections in the absence of hMAbs. Virus infection in the absence of hMAbs was used as internal control. Mean values and standard deviation are shown. Standard error was calculated based on 2-6 replicates.

Example 4: Identification of LASV GP-Specific hMAbs with Strong Broadly Neutralizing Activity (BNhMAbs) Against GPs from Different LCMV Strains in Cell-Based Assays A validated cell-based microneutralization assay was used to identify LASV GP-specific hMAbs that not only cross-reacted with different LCMV GPs, but also neutralized LCMV ARM, as they would represent primary candidates to display broadly antiviral activity in vivo against LCMV strains previously associated with disease cases in humans. From the 15 LASV GP-specific neutralizing hMAbs, six of them (12.1F, 37.2D, 9.8A, 18.5C, 37.2G and 36.9F) neutralized LCMV ARM, as shown in FIG. 2, with IC50<1 μg/mL, with the exception of 18.5C that exhibited a higher (>10 μg/mL) IC50. Results are displayed in Table 2, which shows the neutralizing activity of the 15 LASV GP-specific neutralizing hMAbs against LCMV ARM, and in particular, the IC50 and IC80 values of the 15 LASV GP-specific neutralizing hMAbs against LCMV ARM. Values were obtained from the cell-based microneutralization assay (shown in FIG. 2) using LASV or LCMV GP-pseudotyped rLCMVΔGP/GFP viruses. Grey indicates LASV GP-specific neutralizing hMAbs that neutralized LCMV GP ARM. Neutralization of LASV GP-pseudotyped rLCMVΔGP/GFP was similar to neutralization results obtained using the LASV GP-pseudotyped lentivirus particles shown in Table 1.

TABLE 2

Neutralizing activity of 15 LASV GP-specific neutralizing hMAbs against LCMV Armstrong strain (ARM).

| | LASV Josiah (IV) | | LCMV ARM | |
|---|---|---|---|---|
| hMAb | IC50 | IC80 | IC50 | IC80 |
| 25.10C | 0.160 | 0.247 | >10 | >10 |
| 12.1F | 0.172 | 0.258 | 0.167 | 0.265 |
| 8.9F | 0.134 | >10 | >10 | >10 |
| 37.2D | 0.137 | 0.260 | 0.518 | 2.358 |
| 37.7H | 0.134 | 0.214 | >10 | >10 |
| 25.6A | 0.188 | 0.300 | >10 | >10 |
| 9.8A | 0.139 | 0.253 | 0.112 | 0.248 |
| 18.5C | >10 | >10 | 2.207 | 4.83 |
| 8.11G | >10 | >10 | >10 | >10 |
| 37.2G | 0.405 | 1.776 | 0.525 | 2.461 |
| 2.9D | 0.942 | 2.706 | >10 | >10 |
| NE13 | 0.567 | 1.763 | >10 | >10 |

TABLE 2-continued

Neutralizing activity of 15 LASV GP-specific neutralizing hMAbs against LCMV Armstrong strain (ARM).

| | LASV Josiah (IV) | | LCMV ARM | |
|---|---|---|---|---|
| hMAb | IC50 | IC80 | IC50 | IC80 |
| 19.7E | 1.189 | >10 | >10 | >10 |
| 36.9F | 0.570 | 2.228 | 0.591 | 3.328 |
| 36.1F | 0.132 | 0.206 | >10 | >10 |
| 10.4B | >10 | >10 | >10 | >10 |

Example 5: In Vivo Characterization of Selected GP-Specific BNhMAb

Figure 3:
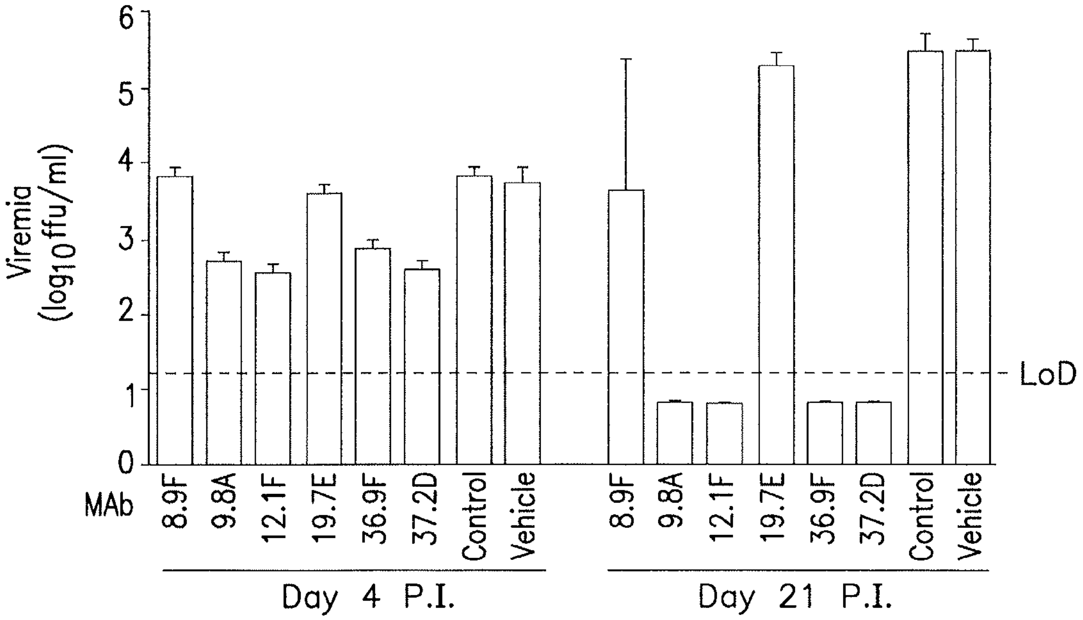
FIG. 3 depicts in vivo neutralization of the 6 LCMV neutralizing antibodies (12.1F, 9.8A, 37.2D, 36.9F, 37.2G, and 18.5C) using the non-crossreactive antibodies 19.7E and 8.9F as internal controls. Mice were infected with rCl-13 (2×106 pfu; i.v.) and treated with the indicated hMAb (20 mg/kg; i.p.), as well as an isotype hMAb control (20 mg/kg, i.p.) or vehicle. At days 4 and 21, post inoculation (p.i.) viremia (i.e., the presence of viruses in the blood) was determined. Results correspond to the average and standard deviation (SD) of four mice/group; LoD=limit of detection.

The well-characterized mouse model of LCMV infection was used to test whether LASV GP-specific neutralizing hMAbs with broadly neutralizing activity against LCMV (shown in FIG. 2 and Table 2) also exhibited in vivo neutralizing activity. The immunosuppressive Clone 13 (Cl-13) strain of LCMV was used. Infection (i.v.) of B6 WT mice with a high dose (≥$10^6$ PFU) of Cl-13 results in transient generalized immunosuppression and establishment of a persistent infection with well-established parameters. Virus clearance takes place between days 60 to 100 (post inoculation (p.i.). However, treatment of Cl-13 infected mice that results in reduced viral load accelerates Cl-13 clearance. Therefore, it was predicted that LASV GP-specific neutralizing hMAbs exhibiting in vivo neutralizing activity would either prevent the establishment of Cl-13 persistence or accelerate its clearance. Mice were treated with the indicated hMAbs at 20 mg/Kg intraperitoneally (i.p.) and were infected with either rCl-13/WT or rCl-13/LASV-GP(mCD). rCl-13/LASV-GP(mCD) was used because it contains mutations C459K and K461G within the cytosolic domain of GP that enhance persistence in mice. The in vivo results are shown in FIG. 3 and correlate with those previously documented in cultured cells (shown in FIG. 2 and Table 2). Mice treated with hMAbs 12.1F, 37.2D, 9.8A and 36.9F prevented persistence of rCl-13/WT. Unexpectedly, hMAbs 37.2G and 18.5C did not prevent Cl-13 persistence in vivo. As expected, based on cross-reactivity and neutralization results in cultured cells, hMAbs 19.7E and 8.9F did not prevent persistence of rCl-13.

Table 3 displays a summary of the cross-reactivity and neutralizing activity in vitro and in vivo of LASV GP-specific hMAbs against six LCMV strains (ARM, WE, RI, OH, WI, and MA) tested.

TABLE 3

Summary of the cross-reactivity and neutralizing activity in vitro and in vivo of LASV GP-specific hMAbs against LCMV.

| | Cross-reactivity | | | | | | Neutralizing activity | |
|---|---|---|---|---|---|---|---|---|
| | $LCMV_{ARM}$ | $LCMV_{WE}$ | $LCMV_{RI}$ | $LCMV_{OH}$ | $LCMV_{WI}$ | $LCMV_{MA}$ | In vitro | In vivo |
| 25.10C | − | − | − | − | − | − | − | − |
| 8.9F | − | − | − | − | − | − | − | − |
| 12.1F | + | + | + | + | + | + | + | + |
| 37.7H | + | + | − | − | + | + | − | − |
| 36.1F | − | − | − | − | − | − | − | − |
| 8.11G | − | − | − | − | − | − | − | − |
| 37.2D | + | + | + | + | + | + | + | + |
| 25.6A | + | + | − | − | + | + | − | − |
| 9.8A | + | + | + | + | + | + | + | + |
| 18.5C | − | − | − | − | − | − | + | − |
| 37.2G | + | + | − | − | + | + | + | − |
| 19.7E | − | − | − | − | − | − | − | − |
| 2.9D | + | + | − | − | + | + | − | − |

TABLE 3-continued

Summary of the cross-reactivity and neutralizing activity in vitro and in vivo of LASV GP-specific hMAbs against LCMV.

| | Cross-reactivity | | | | | | Neutralizing activity | |
|---|---|---|---|---|---|---|---|---|
| | $LCMV_{ARM}$ | $LCMV_{WE}$ | $LCMV_{RI}$ | $LCMV_{OH}$ | $LCMV_{WI}$ | $LCMV_{MA}$ | In vitro | In vivo |
| NE13 | – | – | – | – | – | – | – | – |
| 36.9F | + | + | + | + | + | + | + | + |
| 10.4B | – | – | – | – | – | – | – | – |

Example 6: Assay Development

A panel of murine antibodies against Fab or F(ab')2 fragments of leading candidate therapeutic BNhMAbs was derived for isolation of highly specific anti-idiotypic reagents for assay development. In order to develop a highly protective therapeutic BNhMAb cocktail containing two to four antibodies that together confer maximum pre- and post-exposure protection against LCMV infections, while minimizing the emergence of escape mutants, it is important to characterize the PK of each antibody when administered in a cocktail form. To distinguish between all BNhMAbs included in the cocktail after administration, highly specific anti-idiotypic antibodies are the best tool available to rapidly determine concentration and clearance of individual hMAbs from the blood. A panel of anti-idiotypic antibodies to 37.2D and 12.1F has been developed. Anti-idiotypic mMAbs to 37.2D have specifically detected this BNhMAb when spiked into human serum. The anti-idiotypic antibodies do not capture or detect any other arenaviral BNhMAb tested or any other IgG specificity present in human serum on both ELISA and SPR based studies, and thus are useful for assaying 37.2D.

Example 7: Therapeutic Efficacy of First-In-Class Human LASV-Specific Antibodies in Guinea Pig (GP) and Cynomolgus Macaque (CM) Models of Lassa Fever These studies were done under BSL-4 biocontainment at the Galveston National Laboratory. Outbred Hartley strain GP were challenged i.p. with 1,000 pfu of GP adapted (GPA) LASV Josiah strain (N=5/group). This model has been described recently for testing therapeutics against LASV. The advantage of using outbred animals to model human infection is inferred from the higher variability of immune responses inherent in outbred populations. Viremia was compared by Kruskal-Wallis test supported by Dunn's Multiple comparison posttest (PRISM 5™ software available from GraphPad Software, La Jolla, CA) to detect differences from the control group for time points relevant to onset (day 7) or peak viremia (day 14) as determined from historical data.

Eleven LASV hMAbs tested in a Hartley GP model of LF segregated into three distinct protection groups: (1) 25.6A, 2.9D, 8.9F, 12.1F, and 37.7H conferred 100% protection and no change in clinical score in GPs. (2) 37.2D, 19.7E, and 37.2G protected 80 to 90% of animals. (3) 10.4B, 25.10C, and 36.1F, conferred 40%, 30%, and 20% protection, respectively. An irrelevant recombinant human isotype control (IgG1) Ab did not confer protection (0% survival).

Figure 4:
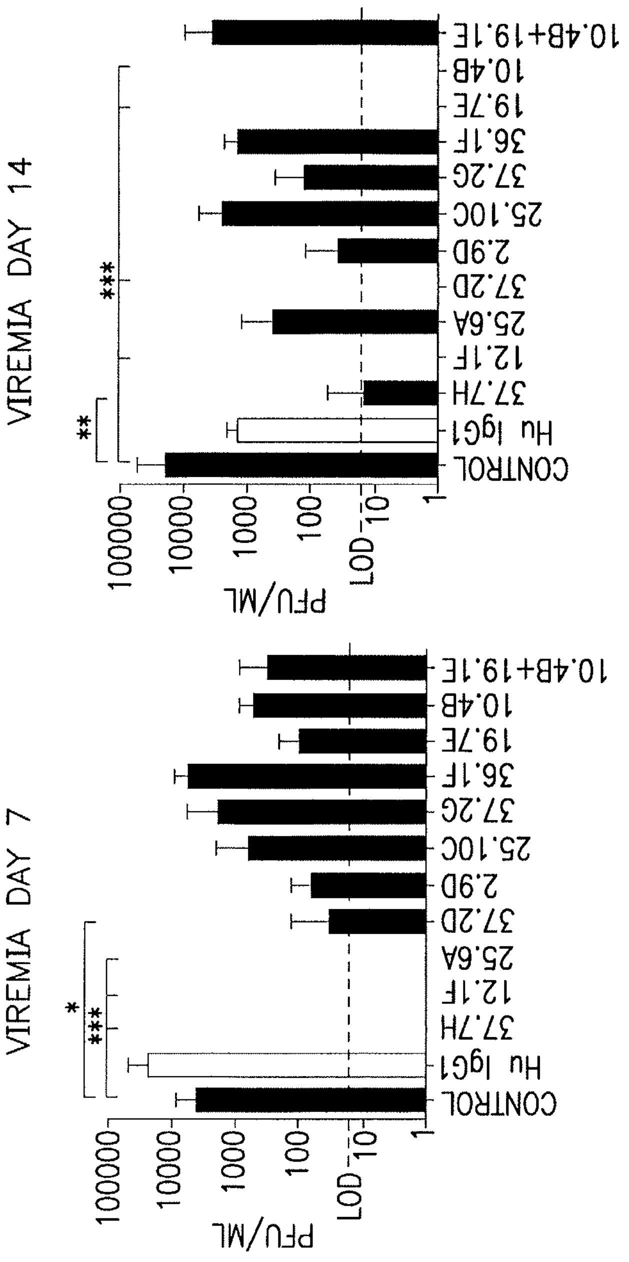
FIG. 4 illustrates Viremia data from treated and control GP plasma on days 7 and 14 PI. Viremia levels for day 7 treatment groups 37.7H, 12.1F, and 25.6A as well as day 14 12.1F, 37.2D, 19.7E, and 10.4B were below the limit of detection (LOD). Error bars represent standard deviation from mean values. *denotes P_0.05. denotes P_0.001. *denotes P<0.0001.
Figure 5:
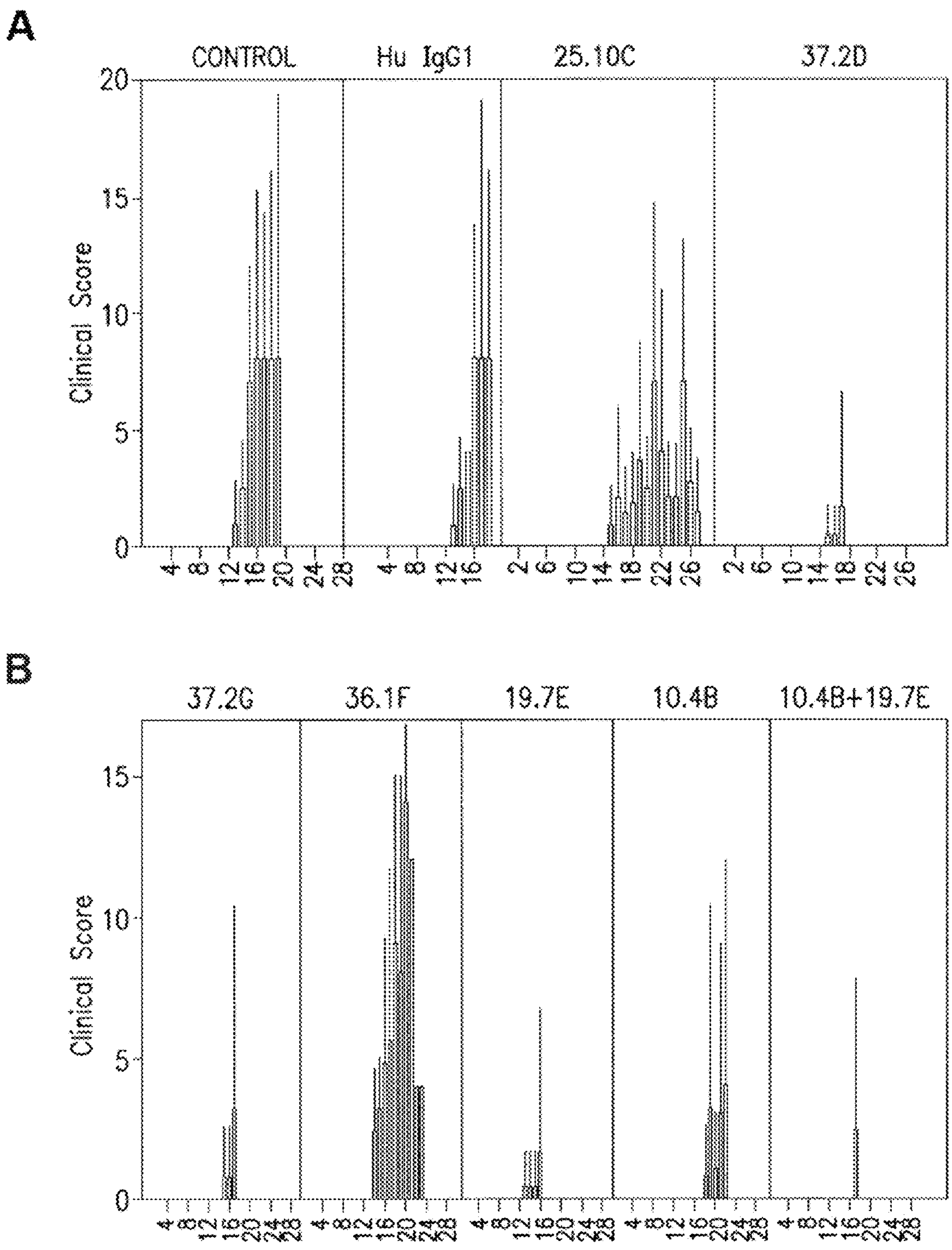
FIG. 5 depicts clinical scores of HuMAb treated and untreated guinea pigs. HuMAbs 8.9F and 12.1 treated GP showed no variation in clinical score from baseline (data not shown). Error bars (thin lines) represent standard deviation from mean values.

With respect to viremia, untreated control animals averaged 3.5 and 4.5 Log PFU/mL on days 7 and 14, respectively, as shown in FIG. 4. Despite 100% protection at the study endpoint, some animals from treatment group 8.9F or 37.7H, 2.9D, and 25.6A had low level viremia on day 7 or 14, respectively. Treatment groups where 90% protection was afforded (37.2D and 19.7E) had reduced mean viremia titers and minimal clinical score values. Treatment groups with 80% or less survival had comparable mean viremia titers to control animals on day 7, but by day 14 mean viremia was markedly lower than control animals. Groups with 80 to 90% survival exhibited relatively low mean clinical scores (FIG. 5) and all remaining treatment groups exhibited concomitant increases in mean clinical scores with decreases in survival per group. Endpoint viremia was not determined for these studies as survival was the primary metric of interest, though all surviving animals demonstrated no clinical signs.

Results from the guinea pig studies informed studies for the Cynomolgus macaque (CM) model of LF. These studies demonstrated that several of the antibodies with high potency in the GP model also protected 100% of the CMs when administered on the day of challenge. 19.7E protected 75% of CMs. Notably a treatment dose as low as 6 mg/kg of hMAb 37.2D provided 100% protection in CMs, whereas 19.7E protected 75% of CMs. A cocktail of three human MAbs (37.2D, 12.1F, and 8.9F at 15 mg/kg each) rescued 100% of CMs even after delay in the start of treatment to 3, 6, or 8 days post-infection (therapeutic walk-out studies). At 8 days post-infection, untreated CMs had developed high viral loads and were extremely ill. CM also were protected from lethal LF induced by challenge with either strain Josiah (lineage IV) or a contemporary lineage II strain derived from a lethal case of LF in Nigeria, both with the first treatment administered at 8 days post-infection.

Example 8: Structural Definition of the Anti-LASV 37.7H Epitope

Monomeric GPCysR4 was incubated with excess Fab 37.7H and subjected to SEC-MALS analysis. SEC-MALS indicated the formation of trimeric GP-Fab complexes in addition to monomeric GP-Fab complexes. Crystals of both the monomeric and trimeric fractions of the GPCysR4-Fab 37.7H complex formed in space group P6122 and diffract to 3.2 Å with a trimer of GP bound to three Fabs in the asymmetric unit. Phases were determined with an iterative approach by using molecular replacement with a related Fab structure and the LCMV GP crystal structure.

The antibody 37.7H against LASV neutralizes viruses representing all four known lineages of LASV in vitro and offers protection from lethal LASV challenge in guinea pig and nonhuman primates. The antibody simultaneously binds two GP monomers at the base of the GP trimer, where it engages four discontinuous regions of LASV GP, two in "site A" and two in "site B". Site A contains residues 62 to 63 of the N-terminal loop of GP1 and residues 387 to 408 in the T-loop and HR2 of GP2. Site B contains residues 269 to 275 of the fusion peptide and residues 324 to 325 of HR1 of GP2. In total, 37.7H buries about 1620 Å$^2$ of GP: about 1000 Å$^2$ of GP at site A and about 620 Å$^2$ of GP at site B. Although nearly the entire surface buried on GP belongs to GP2, the presence of both GP1 and GP2 is critical for 37.7H recognition, likely because GP1 is required to maintain the proper prefusion conformation of GP2 for 37.7H binding.

The antibody 37.7H also recognizes the GPC of LCMV but does not recognize the GPC of the more distantly related Old World arenavirus LUJV nor the GPC of New World arenaviruses. A sequence comparison among these arenaviruses demonstrates nearly complete sequence conservation throughout the 37.7H epitope for all LASV lineages and LCMV. However, the sequences of LUJO, JUNV, and MACV GPCs are far more divergent, particularly in HR2 of GP2, which is heavily involved in binding to 37.7H. The 37.7H antibody neutralizes by stabilizing the prefusion GP.

The quaternary nature and the involvement of the fusion peptide in the 37.7H epitope suggest that this antibody neutralizes the virus by stabilizing GPC in the prefusion conformation, thereby preventing the conformational changes required for infection. This was verified by analyzing the ability of LASV GP-pseudotyped recombinant vesicular stomatitis virus (rVSV-LASV GP) to mediate fusion with cell membranes.

Figure 6:
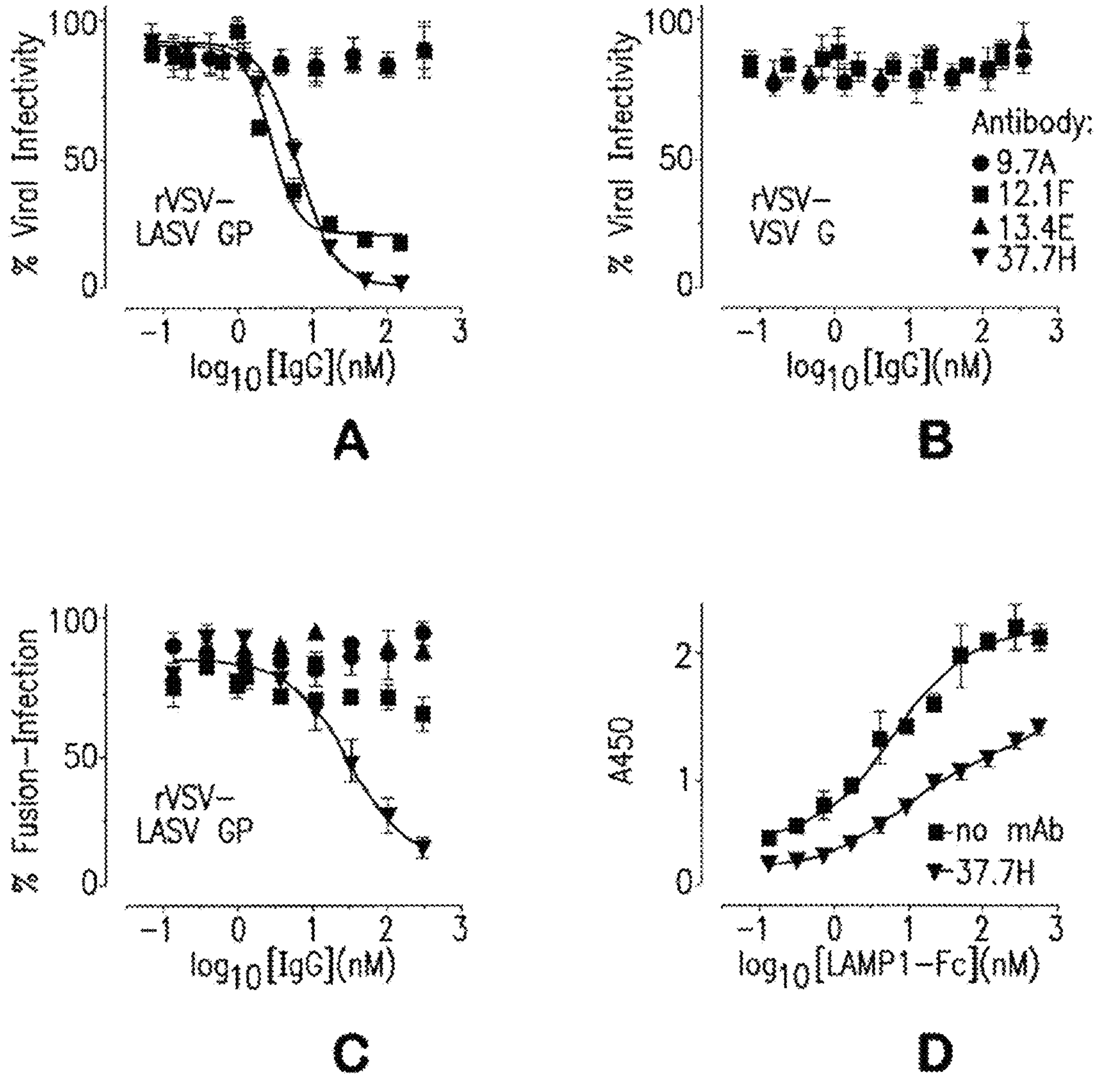
FIG. 6 illustrates the effect of antibodies on rVSV-LASV GP infection and fusion. Antibody-mediated neutralization of (A) rVSV-LASV GP or (B) rVSV-VSV-G. The antibody 9.7A is non-neutralizing and in the same competition group as 37.7H (GPC-B); 13.4E binds to a linear epitope in the T-loop of GP2; 12.1F binds to the GP1 subunit of LASV. Error bars indicate the standard deviation of at least six (two biological replicates, each having three or more technical replicates). (C) Antibody-mediated inhibition of rVSV-LASV GP fusion at the cell surface. Error bars indicate the standard error of the mean of six (except 37.7H, where N=9). (D) Fab 37.7H reduces binding of a LAMP1-Fc fusion protein to LASV GPCysR4. Error bars indicate the standard deviation of six and three technical replicates.

First the ability of 37.7H to neutralize rVSVLASV GP was determined. FIG. 6 shows the effect of antibodies on rVSV-LASV GP infection and fusion. Antibody-mediated neutralization of rVSV-LASV GP is shown in FIG. 6, Panel A. Antibody-mediated neutralization of rVSV-VSV-G is shown in FIG. 6, Panel B. The antibody 9.7A is non-neutralizing antibody and in the same competition group as 37.7H (GPC-B); 13.4E binds to a linear epitope in the T-loop of GP2; 12.1F binds to the GP1 subunit of LASV. Error bars indicate the standard deviation of at least six (two biological replicates, each having three or more technical replicates). FIG. 6, Panel C shows antibody-mediated inhibition of rVSVLASV GP fusion at the cell surface. Error bars indicate the standard error of the mean of six (except 37.7H, where N=9). FIG. 6, Panel D shows Fab 37.7H reduces binding of a LAMP1-Fc fusion protein to LASV GPCysR4. Error bars indicate the standard deviation of six and three technical replicates.

37.7H effectively prevented cellular infection by rVSV-LASV GP, as did the antibody 12.1F, which binds to the upper, 3-sheet face of LASV GP1 and is presumed to block cell attachment. In contrast, antibodies 13.4E, which binds a linear epitope in the T-loop, and 9.7A, which is a non-neutralizing GPC-B antibody, did not prevent viral infection (FIG. 6, Panels A and B).

Next, the ability of 37.7H to prevent fusion of rVSV-LASV GP with cell membranes when exposed to low pH was examined. Unlike the non-neutralizing antibodies 9.7A and 13.4E, which were not effective in preventing fusion, 37.7H reduced fusion by nearly 80% compared with rVSV-LASV GP alone (FIG. 6, Panel C). In contrast, the neutralizing antibody against GP1 (anti-GP1), 12.1F, showed only a slight reduction in infectivity, suggesting that the effect of 37.7H was strictly due to disruption in fusogenicity of the GPC and not attachment to cells.

Before exposure of the GP2 fusion peptide and loop and subsequent fusion of the viral and host cell membranes, LASV GP1 engages LAMP1. Engagement of this receptor is thought to require conformational changes in GP1 that are triggered by exposure to the low pH in the endosome. Tomography of LASV spikes in the presence of low pH and LAMP1 shows an opening of the trimer compared with its neutral pH conformation. To determine whether 37.7H could prevent these conformational changes, the ability of GPCysR4 to bind to a soluble LAMP1-Fc fusion alone and when bound to Fab 37.7H was analyzed. In the absence of Fab 37.7H, GPCysR4 effectively bound to LAMP1 when exposed to low pH. In the presence of Fab 37.7H, however, interaction between GPCysR4 and LAMP1 was markedly reduced (FIG. 6, Panel D).

Based on crystallographic data, the footprint of 37.7H and the footprint of LAMP1 are separated by about 50 Å, and the angle adopted by the bound Fab fragments of 37.7H suggests that it is unlikely to sterically interfere with LAMP1. Thus, there are likely to be conformational changes in GP1 required for LAMP1 binding that are prevented by this human survivor antibody. Taken together, these results demonstrate that the probable mechanism of action for 37.7H and probably for other antibodies in its potent GPC-B competition group is stabilization of the prefusion GPC trimer and prevention of the conformational changes required for binding of LAMP1 and triggering of the GP2 fusion peptide and fusion loop in the endosome.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only with the true scope and spirit of the invention indicated by the claims.

The following reference articles are incorporated herein by reference.

REFERENCES

1. Auperin, D. D., Sasso, D. R. and McCormick, J. B. (1986). Nucleotide sequence of the glycoprotein gene and intergenic region of the Lassa virus S genome RNA. Virology 154, 155-167.
2. Beyer, W. R., Popplau, D., Garten, W., von Laer, and Lenz O. (2003). Endoproteolytic processing of the lymphocytic choriomeningitis virus glycoprotein by the sibtilase SKI-1/S1P. J. Virol. 77, 2866-2872.
3. Buchmeier, M. J. (2002). Arenaviruses: protein structure and function. Curr. Top. Microbiol. Immunol. 262, 259-173.
4. Buchmeier, M. J., and Parekh, B. S. (1987). Protein structure and expression among arenaviruses. Current Topics in Microbiology and Immunology 133, 41-57.
5. Buchmeier, M. J., Lewicki, H. A., Tomor, O., and Jonhson, K. M. (1980). Monoclonal antibodies to lymphocytic choriomeningitis virus reacts with pathogenic arenaviruses. Nature, London 288, 4876-4877.
6. Burnette, W. N. (1981). "Western Blotting": electrophoretic transfer of proteins from sodium dodecyl sulfate-polyacrylamide gels to unmodified nitrocellulose and radiographic detection with antibody and radioiodinated protein A. Analytical Biochemistry 112, 195-203.
7. Clegg, J. C. and Lloyd, G. (1983). Structureal and cell-associated proteins of Lassa virus. Journal of General Virology 64, 1127-1136.
8. Eichler, R., Lenz, O., Strecker, T., Eickmann, M., Klenk, H. D., and Garten, W. (2004). Lassa virus glycoprotein signal peptide displays a novel topology with an extended ER-luminal region. J. Biol. Chem. 279, 12293-12299.

9. Eichler, R., Lenz, O., Strecker, T., Eickmann, M., Klenk, H. D., and Garten, W. (2003). Identification of Lassa virus glycoprotein signal peptide as a trans-acting maturation factor. EMBO Rep. 4, 1084-1088.
10. Eichler, R., Lenz, O., Strecker, T., Eickmann, and Garten, W. (2003). Signal peptide of Lassa virus glycoprotein GP-C exhibits an unusual length. FEBS Lett. 538, 203-206.
11. Elagoz, A., Benjannet, S., Mammarbassi, A., Wickham, L., and Seidah, N. G. (2002). Biosynthesis and cellular trafficking of the convertase SKI-1/S1P: ectodomain shedding requires SKI-1 activity. J. Biol. Chem. 277, 11265-11275.
12. Hufert, F. T., Ludke, W., and Schmitz, H. (1989). Epitope mapping of the Lassa virus nucleocapsid protein using monoclonal anti-nucleocapsid antibodies. Archives of Virology 106, 201-212.
13. Lenz, O., ter Meulen, J., Feldmann, H., Lenk, H.-D., and Garten, W. (2000). Identification of a novel consensus sequence at the cleavage site of the Lassa virus glycoprotein. J. Virol. 74, 11418-11421.
14. Lukashevich L. S., Clegg J. C., and Sidibe K. (1993). Lassa virus activity in Guinea: distribution of human antiviral antibody defined using enzyme-linked immunosorbent assay with recombinant antigen. J Med Virol. 40, 210-7.
15. McCormick, J. B., and Fisher-Hoch, S. P. (2002). Lassa Fever. Curr. Top. Microbiol. Immunol. 262, 75-109.
16. Ruo, S. L., Mitchell, S. W., Killey, M. P., Roumillat, L. F., Fisher-Hoch, S. P., and McCormick, J. B. (1991). Antigenic relatedness between arenaviruses defined at the epitope level by monoclonal antibodies. Journal of General Virology 72, 549-555.
17. Sanchez, A., Pifat, D. Y., Kenyon, R. H., Peters, C. J., McCormick, J. B., and Kiley, M. P. (1989). Junin virus monoclonal antibodies: characterization and cross-reactivity with other arenaviruses. J. Gen. Virol. 70, 1125-1132.
18. Spiropoulou, C. F., Kunz, S., Rollin, P. E., Campbell, K. P., and Oldstone, M. B. A. (2002). New World arenavirus clade C, but not clade A and B viruses, utilizes a-dystroglycan as its major receptor. J. Virol. 76, 5140-5146.
19. ter Meulen J., Badusche M., Kuhnt K., Doetze A., Satoguina J., Marti T., Loeliger C., Koulemou K., Koivogui L., Schmitz H., Fleischer B., and Hoerauf A. (2000). Characterization of human CD4(+) T-cell clones recognizing conserved and variable epitopes of the Lassa virus nucleoprotein. J. Virol. 74, 2186-92.
20. ter Meulen, J., Koulemou K., Wittekindt T., Windisch K., Strigl S., Conde S., and Schmitz H. (1998). Detection of Lassa Virus Antinucleoprotein Immunoglobulin G (IgG) and IgM Antibodies by a Simple Recombinant Immunoblot Assay for Field Use. J. Clin. Microbiol. 36, 3143-3148.
21. York, J., Agnihothram, S. S., Ronamowski, V., and Nunberg, J. H. (2005). Genetic analysis of heptad-repeat regions in the G2 fusion subunit of the Junin arenavirus envelope glycoprotein. Virology 343, 267-279.
22. York, J., Ronamowski, V., Lu, M., and Nunberg, J. H. (2004). The signal peptide of the Junin arenavirus envelope glycoprotein is myristoylated and forms an essential subunit of the mature G1-G2 complex. J. Virol. 78, 10783-10792.
23. Shaffer J G, Grant D S, Schieffelin J S, Boisen M L, Goba A, et al. 2014. Lassa Fever in Post-Conflict Sierra Leone. *PLoS Negl Trop Dis* 8: e2748.
24. Hartnett J N, Boisen M L, Oottamasathien D, Jones A B, Millett M M, . . . Garry R F, Branco L M & the VHFC (2015). Current and emerging strategies for the diagnosis, prevention and treatment of Lassa fever. Future *Virology. Review*. Vol. 10, No. 5, Pages 559-584.
25. Andersen K G, Shapiro B J, Matranga C B, Sealfon R, Lin A E, . . . Branco L M, Gire S K, Phelan E, Tariyal R, Tewhey R, . . . Garry R F, Sabeti P C. Clinical Sequencing Uncovers Origins and Evolution of Lassa Virus. *Cell*. 2015 Aug. 13; 162(4):738-50.
26. Luis M Branco, Jessica N Grove, Matt L Boisen, Jeffrey G Shaffer, Augustine Goba, . . . Robert F Garry. Emerging trends in Lassa fever: redefining the role of immunoglobulin M and inflammation in diagnosing acute infection. *Virology Journal* 2011, 8:478 (24 Oct. 2011).
27. Jessica N Grove, Luis M Branco, Matt L Boisen, Ivana J Muncy, Lee A Henderson, . . . Robert F Garry. Capacity building permitting comprehensive monitoring of a severe case of Lassa hemorrhagic fever in Sierra Leone with a positive outcome: Case Report. *Virology Journal* 2011, 8:314 (20 Jun. 2011).
28. Luis M Branco, Jessica N Grove, Frederick J Geske, Matt L Boisen, Ivana J Muncy, . . . Robert F Garry. Lassa virus-like particles displaying all major immunological determinants as a vaccine candidate for Lassa hemorrhagic fever. *Virology Journal* 2010, 7:279 (20 Oct. 2010).
29. Luis M Branco, Matt L Boisen, Kristian G Andersen, Jessica N Grove, Lina M Moses, . . . Robert F Garry. Lassa Hemorrhagic Fever in a Late Term Pregnancy from Northern Sierra Leone with a Positive Maternal Outcome: Case Report. *Virology Journal* 2011, 8:404 (15 Aug. 2011).

SEQUENCE LISTING

```
Sequence total quantity: 144
SEQ ID NO: 1             moltype = DNA  length = 670
FEATURE                  Location/Qualifiers
misc_feature             1..670
                         note = cDNA 10.4B HC variable region
source                   1..670
                         mol_type = other DNA
                         organism = synthetic construct
SEQUENCE: 1
tgcgcgttac ngatccaagc tgtgaccggc gcctacctga gatcaccggt gctagcacca  60
tggagacaga cacactcctg ctatgggtac tgctgctctg ggttccaggt tccactggtg  120
accaggtgca gctggtacag tctgggggag gcgtggtcca gcctgggagg tccctgagag  180
tctcctgtgt tacgtctgga ttcaatttca gagcctacgg catgcactgg gtccgccaga  240
ttccaggcaa gggactggag tgggtggcag atatttggtc tgccgagact aatagacact  300
atgcagattc cgtgaagggc cgattcacca tctccagaga caactccaag agcacactgt  360
atctgcaaat gaacagcctg agagccgagg acacgggcgt atatttctgt gccaaagcgc  420
```

-continued

```
gaccaggcta tgattatgtc gttgacttat ggggccaggg aacgctggtc atcgtctcct  480
cagcttccac caagggccca tcggtcttcc ccctggcgcc ctgctccagg agcacctctg  540
ggggcacagc ggccctgggc tgcctggtca aggactactt ccccgaaccg gtgacggtgt  600
cgtggaactc aggcgccctg accagcggcg tgcacacctt cccggctgtc ctacagtcct  660
caggactcta                                                          670

SEQ ID NO: 2            moltype = DNA  length = 819
FEATURE                 Location/Qualifiers
misc_feature            1..819
                        note = cDNA 19.7E HC variable region
source                  1..819
                        mol_type = other DNA
                        organism = synthetic construct
SEQUENCE: 2
atccagctgt gaccggcgcc tacctgagat caccggtgct agcaccatgg agacagacac  60
actcctgcta tgggtactgc tgctctgggt tccaggttcc actggtgacg aggtgcagct  120
ggtggagtct gggggaggct tagttcggcc tggggggtcc ctgagactct cctgtgcagc  180
ctctggattc tccttcagta gctactcgat gcactgggtc cgccatgttc ctgggaaggg  240
gctggtgtgg gtctcatata ttaatagtga tgggagtact aaaatctacg cggactccgt  300
gaagggccga ttctccatct ccagagacaa tgccaagaac aagctctatc tgcaaatgga  360
cagtttgaga gtcgaggaca cggctgtata ttcgtgtgta aggcttgtac attacgactg  420
gtccccattc gtgtggggcc agggaaccct ggtcaccgtc tcctcagcct ccaccaaggg  480
cccatcggtc ttcccctgg caccctcctc caagagcacc tctgggggca cagcggccct  540
gggctgcctg gtcaaggact acttccccga accggtgacg gtgtcgtgga actcaggcgc  600
cctgaccagc ggcgtgcaca ccttcccggc tgtcctacag tcctcaggac tctactccct  660
cagcagcgtg gtgaccgtgc cctccagcag cttgggcacc cagacctaca tctgcaacgt  720
gaatcacaag cccagcaaca ccaaggtgga caagaaagtt gagcccaaat cttgtgacaa  780
aactcacaca tgcccaccgt gcccagcacc tgaactcct                          819

SEQ ID NO: 3            moltype = DNA  length = 920
FEATURE                 Location/Qualifiers
misc_feature            1..920
                        note = cDNA 2.9D HC variable region
source                  1..920
                        mol_type = other DNA
                        organism = synthetic construct
SEQUENCE: 3
gtcactgcac ctcggttcta tcgattggct agcaccatgg agacagacac actcctgcta  60
tgggtactgc tgctctgggt tccaggttcc actggtgacg aggtgcagct ggtggagtct  120
gggggaggcc tggtcaagcc tggggggtcc cttagactct cctgtgcagc ctctggattc  180
accttcacta gatttacttt gacctgggtc cgccaggctc cagggaaggg gctggagtgg  240
gtctcatcca ttagtagtgg gagtagtgac ataaactacg cagactcagt gaagggccga  300
ttcaccatat ccagagacaa cgccaggaac tccctgttcc tgcaaatgag cagcctgaga  360
gtcgacgaca cggctgtgta ttactgtgcg aaagatcccc ggtcggggat ctctggtcgc  420
tacgggatgg acgtctgggg ccaagggacc acggtcatcg tctcctcagc ttccaccaag  480
ggcccatcgg tcttcccct ggcgccctgc tccaggagca cctctggggg cacagcggcc  540
ctgggctgcc tggtcaagga ctacttcccc gaaccggtga cggtgtcgtg gaactcaggc  600
gccctgacca gcggcgtgca caccttcccg gctgtcctac agtcctcagg actctactcc  660
ctcagcagcg tggtgaccgt gccctccagc agcttgggca cccagaccta catctgcaac  720
gtgaatcaca agcccagcaa caccaaggtg gacaagagag ttgagcccaa atcttgtgac  780
aaaactcaca catgcccacc gtgcccagca cctgaactcc tggggggacc gtcagtcttc  840
ctcttccccc caaaacccaa ggacaccctc atgatctccc ggacccctga ggtcacatgc  900
gtggtggtgg acgtgagcca                                                920

SEQ ID NO: 4            moltype = DNA  length = 540
FEATURE                 Location/Qualifiers
misc_feature            1..540
                        note = cDNA 25.6A HC variable region
source                  1..540
                        mol_type = other DNA
                        organism = synthetic construct
SEQUENCE: 4
acctcggttc ttcgattggc tagcaccatg gagacagaca cactcctgct atgggtactg  60
ctgctctggg ttccaggttc cactggtgac caggtgcagc tgcaggagtc aggaggaggc  120
ctggtcaagg ctggggggtc cctgagactc tcctgtgcag cctctggatt catgttcgag  180
agatatagcc ttcactgggt ccgtcagact ccaggcaagg ggctggagtg ggtctcatcc  240
attagtagtc ttagtggcag tcacataaac tacgcagact cagtgaaggg ccgattcacc  300
atctccagag acaacgccaa gaattcactg tctctgcaaa tgaacagcct gagagtcgaa  360
gacacggcta tatattattg tgcgagagat cgacgttcgg ggagttcccc cgtccccttg  420
gacgtctggg gccaagggac cacggtcacc gtctcctctg cctccaccaa gggcccatcg  480
gtcttccccc tggcaccctc ctccaagagc acctctgggg gcacagcggc cctgggctgc  540

SEQ ID NO: 5            moltype = DNA  length = 855
FEATURE                 Location/Qualifiers
misc_feature            1..855
                        note = cDNA 36.1F HC variable region
source                  1..855
                        mol_type = other DNA
                        organism = synthetic construct
```

```
SEQUENCE: 5
gtcactgccc tcggttctat cgattggcta gcaccatgga gacagacaca ctcctgctat  60
gggtactgct gctctgggtt ccaggttcca ctggtgacca ggtgcagctg caggagtcgg  120
gcgcgggact ggtgaagcct tcggagaccc tgtccctcac ctgcgctgtc tcaggtggac  180
ccttcagcgg tgcctactgg acgtggatcc gccaaactcc agggaagggg ctggagtgga  240
ttggagaggc cggtcggagt ggaaccacca actacaatcc gtccctcaag agtcgagtca  300
ccatatcact ggacacgtcc aagagccagt tttccctgaa gctgacttcc gtgaccgccg  360
cggacacggc tgtttacttc tgtgggagac gccaaataat gtctttgagt aatctttata  420
agagacccgt tgactcttgg ggccggggaa ccccggtcat cgtctcctca gcctccacca  480
agggcccatc ggtcttcccc ctggcaccct cctccaagag cacctctggg ggcacagcgg  540
ccctgggctg cctggtcaag gactacttcc ccgaaccggt gacggtgtcg tggaactcag  600
gcgccctgac cagcggcgtg cacaccttcc cggctgtcct acagtcctca ggactctact  660
ccctcagcag cgtggtgacc gtgccctcca gcagcttggg cacccagacc tacatctgca  720
acgtgaatca caagcccagc aacaccaagg tggacaagag agttgagccc aaatcttgtg  780
acaaaactca cacatgccca ccgtgcccag cacctgaact cctgggggga ccgtcagtct  840
tcctcttccc cccaa                                                   855

SEQ ID NO: 6           moltype = DNA  length = 874
FEATURE                Location/Qualifiers
misc_feature           1..874
                       note = cDNA 36.9F HC variable region
source                 1..874
                       mol_type = other DNA
                       organism = synthetic construct
SEQUENCE: 6
gtcactgccc tcggttctat cgattggcta gcaccatgga gacagacaca ctcctgctat  60
gggtactgct gctctgggtt ccaggttcca ctggtgacga ggtgcagctg gtgcagtctg  120
gaggaggcct ggtcaaggcg ggggggtccc tgaaactctc ctgtggagcc tctggattca  180
ccttcagtag ttatagcatg agctgggtcc gccaggctcc agggaagggg ctggagtggg  240
tctcatacat tagtagtggt gggagttcta tacactacgc agactcagtg aagggccgat  300
tcaccatctc cagagacaac gccaagaatt cactgtatct gcaaatgaag aacctgaggg  360
tcgacgacac gggtcggtat tattgtgtga gagatccccg atcggggatc tctggtcggt  420
acggtatgga cgtctggggt caagggacca cggtcaccgt ctcctcagcc tccaccaagg  480
gcccatcggt cttccccctg gcaccctcct ccaagagcac ctctgggggc acagcggccc  540
tgggctgcct ggtcaaggac tacttccccg aaccggtgac ggtgtcgtgg aactcaggcg  600
ccctgaccag cggcgtgcac accttcccgg ctgtcctaca gtcctcagga ctctactccc  660
tcagcagcgt ggtgaccgtg ccctccagca gcttgggcac ccagacctac atctgcaacg  720
tgaatcacaa gcccagcaac accaaggtgg acaagagagt tgagcccaaa tcttgtgaca  780
aaactcacac atgcccaccg tgcccagcac ctgaactcct ggggggaccg tcagtcttcc  840
tcttcccccc aaaacccaagg acaccctcat gatc                             874

SEQ ID NO: 7           moltype = DNA  length = 859
FEATURE                Location/Qualifiers
misc_feature           1..859
                       note = cDNA 37.2D HC variable region
source                 1..859
                       mol_type = other DNA
                       organism = synthetic construct
SEQUENCE: 7
tcactgccct cggttctatc gattggctag caccatggag acagacacac tcctgctatg  60
ggtactgctg ctctgggttc caggttccac tggtgacgaa gtgcagctgg tgcagtctgg  120
agctgaggtg aagaagcctg gggcttcagt gaaggtgtcc tgcaaggcct ctggttacac  180
ctttacgaaa tacggaatca gctgggtgcg acaggcccct ggacaagggc ttgagtggat  240
gggatggatc agcgcgttta atggttacac aaggtatggt cagagattcc agggcaaagt  300
caccatgacc acagacacat ccacgaacac agcctctttg gaggtgagga ccctgacatc  360
taacgacacg gccgtctatt actgtgcgag acaatatccc gaccaatata gtagcagcgg  420
ttggccccgc ctcttcgcca tggacgtctg gggccaaggg accacggtca tcgtctcccc  480
agcctccacc aagggcccat cggtcttccc cctggcaccc tcctccaaga gcacctctgg  540
gggcacagcg gccctgggct gcctggtcaa ggactacttc cccgaaccgg tgacggtgtc  600
gtggaactca ggcgccctga ccagcggcgt gcacaccttc ccggctgtcc tacagtcctc  660
aggactctac tccctcagca gcgtggtgac cgtgccctcc agcagcttgg gcacccagac  720
ctacatctgc aacgtgaatc acaagcccag caacaccaag gtggacaaga gagttgagcc  780
caaatcttgt gacaaaactc acacatgccc accgtgccca gcacctgaac tcctgggggg  840
accgtcagtc ttcctcttc                                               859

SEQ ID NO: 8           moltype = DNA  length = 960
FEATURE                Location/Qualifiers
misc_feature           1..960
                       note = cDNA 37.2G HC variable region
source                 1..960
                       mol_type = other DNA
                       organism = synthetic construct
SEQUENCE: 8
tcactgccct cggttctatc gattggctag caccatggag acagacacac tcctgctatg  60
ggtactgctg ctctgggttc caggttccac tggtgacgag gtgcagctgg tggagtctgg  120
gggaggcctg gtcaagccgg gggggtcccg gagactctcc tgtgctgcct ctggattcac  180
cttcagtaga gataccatga cctgggtccg ccaggctcca gggaaggggc tggagtgggt  240
cgcatccata agtagtggta gcagtgacat aaactacgca gactcagtga agggccgatt  300
caccatctcc agagacaacg gcaagaactc actgtatctg cacatgaaca gcctgagagc  360
```

-continued

```
cgacgacacg gctatatatt actgtgcgag agatccccgg tcgggaatct ctggtcggta  420
tggtatggac gtctggggcc aagggaccac ggtcaccgtc tcctcagcct ccaccaaggg  480
cccatcggtc ttccccctgg caccctcctc caagagcacc tctgggggca cagcggccct  540
gggctgcctg gtcaaggact acttccccga accggtgacg gtgtcgtgga actcaggcgc  600
cctgaccagc ggcgtgcaca ccttcccggc tgtcctacag tcctcaggac tctactccct  660
cagcagcgtg gtgaccgtgc cctccagcag cttgggcacc cagacctaca tctgcaacgt  720
gaatcacaag cccagcaaca ccaaggtgga caagagagtt gagcccaaat cttgtgacaa  780
aactcacaca tgcccaccgt gcccagcacc tgaactcctg gggggaccgt cagtcttcct  840
cttcccccca aaacccaagg acaccctcat gatctcccgg acccctgagg tcacatgcgt  900
ggtggtggac gtgagccacg aagaccctga ggtcaagttc aactggtacg tggacggcgt  960

SEQ ID NO: 9           moltype = DNA  length = 924
FEATURE                Location/Qualifiers
misc_feature           1..924
                       note = cDNA 37.7H HC variable region
source                 1..924
                       mol_type = other DNA
                       organism = synthetic construct
SEQUENCE: 9
gtcactgcac ctcggttcta tcgattggct agcaccatgg agacagacac actcctgcta  60
tgggtactgc tgctctgggt tccaggttcc actggtgacg aggtgcagct ggtgcagtct  120
ggaggaggcc tggtcaaggc ggggggtcc ctgaggctct cctgtgcagc ctccggattc  180
acattcagca cctacagtat gaactggatc cgccaggctc cagggaaggg gctggagtgg  240
gtcgcttcca ttagtagtcg aagtggcagt cacataaact acgtagactc agtgaaggga  300
cgattcacca tctccagaga caacgccagg gacttattgt atctgcaaat gaacagcctg  360
agagtcgacg actcggctct ctattactgt gcgagagatc gccgttcggg gacttctccc  420
ctccccttgg acgtctgggg ccaagggacc acggtcaccg tcttctcagc ctccaccaag  480
ggcccatcgg tcttccccct ggcaccctcc tccaagagca cctctggggg cacagcggcc  540
ctgggctgcc tggtcaagga ctacttcccc gaaccggtga cggtgtcgtg gaactcaggc  600
gccctgacca gcggcgtgca caccttcccg gctgtcctac agtcctcagg actctactcc  660
ctcagcagcg tggtgaccgt gccctccagc agcttgggca cccagaccta catctgcaac  720
gtgaatcaca agcccagcaa caccaaggtg gacaagagag ttgagcccaa atcttgtgac  780
aaaactcaca catgcccacc gtgcccagca cctgaactcc tgggggggacc gtcagtcttc  840
ctcttccccc caaaacccaa ggacaccctc atgatctccc ggacccctga ggtcacatgc  900
gtggtggtgg acgtgagcca cgaa                                        924

SEQ ID NO: 10          moltype = DNA  length = 911
FEATURE                Location/Qualifiers
misc_feature           1..911
                       note = cDNA 8.9F HC variable region
source                 1..911
                       mol_type = other DNA
                       organism = synthetic construct
SEQUENCE: 10
cctcggttct atcgattggc tagcaccatg gagacagaca cactcctgct atgggtactg  60
ctgctctggg ttccaggttc cactggtgac cagggcacct tgagggagtc tggtccagga  120
ctggtgaggc cttcggagac cctgtccctc acctgcggtg tctctggtta ttccatcagt  180
agtggttact actggggctg gatccggcag cccccaggga aggggctgga gtggattggg  240
aatatctatc gtagtgggag cacctactac aacccgtccc tcaagagtcg agtcaccgtc  300
tcaatagaca cgtccaaaaa ccagttctcc ctgaagttga attctgtgac cgccgcagac  360
acggccgtgt attactgtgc gagatcgggt ataaaagtgg ctgacgacta ttactacgaa  420
atggacgtct ggggccaagg gaccgacgac tactcttacg ctatggacgt ctggggccaa  480
gggaccacgg tcaccgtctc ctcagcctcc accaagggcc catcggtctt ccccctggca  540
ccctcctcca agagcacctc tgggggcaca gcggccctgg gctgcctggt caaggactac  600
ttccccgaac cggtgacggt gtcgtggaac tcaggcgccc tgaccagcgg cgtgcacacc  660
ttcccggctg tcctacagtc ctcaggactc tactccctca gcagcgtggt gaccgtgccc  720
tccagcagct tgggcaccca gacctacatc tgcaacgtga atcacaagcc cagcaacacc  780
aaggtggaca agagagttga gcccaaatct tgtgacaaaa ctcacacatg cccaccgtgc  840
ccagcacctg aactcctggg gggaccgtca gtcttcctct tccccccaaa acccaaggac  900
accctcatga t                                                      911

SEQ ID NO: 11          moltype = DNA  length = 881
FEATURE                Location/Qualifiers
misc_feature           1..881
                       note = cDNA NE13 HC variable region
source                 1..881
                       mol_type = other DNA
                       organism = synthetic construct
SEQUENCE: 11
actgcacctc ggttctatcg attggctagc accatggaga cagacacact cctgctatgg  60
gtactgctgc tctgggttcc aggttccact ggtgacgagg ttcagctggt ggagtctggg  120
ggaggcctgg tcaagcctgg ggggtccctg agactctcct gtgtagcctc tggattcacc  180
ttcagttcct atagcatgaa ctgggtccgc caggctccag ggaaggggct ggagtgggtc  240
tcatccatta gtagtggtag tagttacata gagtacgcag actcagtgaa gggccgactc  300
accatctcca gagacaacgc caagaagtca ctgtatctgc aactgaacag cctgagagcc  360
gaggacacgg ctgtgtatta ctgtgcgaga cacacagctc gaatcgactc ttaccacggt  420
atggacgtct ggggccaagg gaccacagtc accgtctcct cagcctccac caagggccca  480
tcggtcttcc ccctggcacc ctcctccaag agcacctctg gggcacagc ggccctgggc  540
tgcctggtca aggactactt ccccgaaccg gtgacggtgt cgtggaactc aggcgccctg  600
```

-continued

```
accagcggcg tgcacacctt cccggctgtc ctacagtcct caggactcta ctccctcagc  660
agcgtggtga ccgtgccctc cagcagcttg ggcacccaga cctacatctg caacgtgaat  720
cacaagccca gcaacaccaa ggtggacaag agagttgagc ccaaatcttg tgacaaaact  780
cacacatgcc caccgtgccc agcacctgaa ctcctggggg gaccgtcagt cttcctcttc  840
cccccaaaac ccaaggacac cctcatgatc tcccggaccc c                        881

SEQ ID NO: 12          moltype = DNA  length = 921
FEATURE                Location/Qualifiers
misc_feature           1..921
                       note = cDNA 12.1F HC variable region
source                 1..921
                       mol_type = other DNA
                       organism = synthetic construct
SEQUENCE: 12
gtcactgcac ctcggttcta tcgattggct agcaccatgg agacagacac actcctgcta  60
tgggtactgc tgctctgggt tccaggttcc actggtgacc aggtgcagct gcaggagtcg  120
ggcgcaggac tgttgaagcc ttcggagacc ctgtccctca gttgcactgt cgatggtgag  180
tccttcaatg gtttcttctg gacgtggatc cgccagcccc cagggaaggg tctggagtgg  240
attggagaaa tcaatcatct tgcaagcacc ggctacaacc cgtccctcaa gagtcgagtc  300
accatttcag tagacacgtc caagaaccag ttctctttga agttgacctc tgtgaccgcc  360
gcggacacgg ctgtgtatta ctgtgcgaga ggatacagct atggttttgc atggcccaac  420
taccactatt tggacgtctg gggcaaaggg accacggtca ccgtctcctc agcctccacc  480
aagggcccat cggtcttccc cctggcaccc tcctccaaga gcacctctgg gggcacagcg  540
gccctgggct gcctggtcaa ggactacttc cccgaaccgg tgacggtgtc gtggaactca  600
ggcgccctga ccagcggcgt gcacaccttc ccggctgtcc tacagtcctc aggactctac  660
tccctcagca gcgtggtgac cgtgccctcc agcagcttgg gcacccagac ctacatctgc  720
aacgtgaatc acaagcccag caacaccaag gtggacaaga gagttgagcc caaatcttgt  780
gacaaaactc acacatgccc accgtgccca gcacctgaac tcctgggggg accgtcagtc  840
ttcctcttnc cccaaaaccc aaggacaccc tcatgatctc ccggaccccc tgaggtcaca  900
tgcgtggtgg tggacgtgag c                                              921

SEQ ID NO: 13          moltype = DNA  length = 874
FEATURE                Location/Qualifiers
misc_feature           1..874
                       note = cDNA 9.8A HC variable region
source                 1..874
                       mol_type = other DNA
                       organism = synthetic construct
SEQUENCE: 13
ttctatcgat ttggctagca ccatggagac agacacactc ctgctatggg tactgctgct  60
ctgggttcca ggttccactg gtgacgaggt gcagctggtg cagtctggag gacgcttggt  120
acagcctggg gggtccctga gactctcctg tgtagcctct ggattcacct ttagcagcca  180
tgccatgagc tgggtccgcc aggctccagg gaaggggctg gagtgggtct caggttttag  240
tggtagtagt ggtaccacaa agtacgcaga ctccgtgaag ggccggttca ccatctccag  300
agacaattcc aagaaaacgc tgtatctgca aatgaacagc ctgagagccg aggacacggc  360
cgtatattac tgtgcgaaag gcttctcccc atttcgggga gtacaattcc cctactttga  420
ctactggggc cagggaacgc tggtcaccgt ctcctcagcc tccaccaagg gcccatcggt  480
cttcccccctg gcaccctcct ccaagagcac ctctgggggc acagcggccc tgggctgcct  540
ggtcaaggac tacttccccg aaccggtgac ggtgtcgtgg aactcaggcg ccctgaccag  600
cggcgtgcac accttcccgg ctgtcctaca gtcctcagga ctctactccc tcagcagcgt  660
ggtgaccgtg ccctccagca gcttgggcac ccagacctac atctgcaacg tgaatcacaa  720
gcccagcaac accaaggtgg acaagagagt tgagcccaaa tcttgtgaca aaactcacac  780
atgcccaccg tgcccagcac ctgaactcct gggggaccg tcagtcttcc tcttcccccc  840
aaaacccagg acaccctcat gatctcccgg accc                                874

SEQ ID NO: 14          moltype = DNA  length = 898
FEATURE                Location/Qualifiers
misc_feature           1..898
                       note = cDNA 18.5C HC variable region
source                 1..898
                       mol_type = other DNA
                       organism = synthetic construct
SEQUENCE: 14
gtccactgca cctcggttct atcgattggc tagcaccatg gagacagaca cactcctgct  60
atgggtactg ctgctctggg ttccaggttc cactggtgac gaggttcagc tggtggagtc  120
tgggggaggc ctggtcaggc cgggggggtc ccttagactc tcctgtgcag ccgctggatt  180
cactttcaag agttatagca tgaattgggt ccgccaggct ccagggaggg gcctggagtg  240
ggtctcatct atcactagtg gtggtagtaa gacatactat gcagacgtag tgaagggccg  300
attcaccgtc tccagagaca acgccaagca gtcgctctat ctgcaaatga acagcctgag  360
agccgaggac acggctatat acttctgtgc gagatcccta catagtacca gccagcctag  420
ctacatggac gtctggggca gaaagatcac ggtcatcgtc tcctcagcct ccaccaaggg  480
cccatcggtc ttcccctgg caccctcctc caagagcacc tctgggggca cagcggccct  540
gggctgcctg gtcaaggact acttccccga accggtgacg gtgtcgtgga actcaggcgc  600
cctgaccagc ggcgtgcaca ccttcccggc tgtcctacag tcctcaggac tctactccct  660
cagcagcgtg gtgaccgtgc cctccagcag cttgggcacc cagacctaca tctgcaacgt  720
gaatcacaag cccagcaaca ccaaggtgga caagagagtt gagcccaaat cttgtgacaa  780
aactcacaca tgcccaccgt gcccagcacc tgaactcctg gggggaccgt cagtcttcct  840
cttcccccca aaacccaagg acaccctcat gatctcccgg accccctgagg tcacatgc    898
```

```
SEQ ID NO: 15          moltype = DNA  length = 903
FEATURE                Location/Qualifiers
misc_feature           1..903
                       note = cDNA 8.11G HC variable region
source                 1..903
                       mol_type = other DNA
                       organism = synthetic construct
SEQUENCE: 15
tgcacctcgg ttctatcgat tggctagcac catggagaca gacacactcc tgctatgggt  60
actgctgctc tgggttccag gttccactgg tgaccaggtg cagctgcagg agtcgggtcc  120
aggactggtg aagccttcgg agaccctgtc cctcacctgc agtatttctg gtgtgtccac  180
cagaaattat tattggagct ggatccgcca gtccccaggg aagggactgg agtggattgg  240
atatatcttt aacattggga ccaccaacta caatccgtcc ctcaagagtc gactcaccat  300
atctgtagac acgtcgaaga accagttctc cctgaagatc acctctgtga ccgctgcgga  360
cacggccgtc tattactgtg cgagtggatt tgagtacggt gactatacct tcgactactg  420
gggccaggga accccggtca ccgtctcctc agcctccacc aagggcccat cggtcttccc  480
cctggcaccc tcctccaaga gcacctctgg gggcacagcg gccctgggct gcctggtcaa  540
ggactacttc cccgaaccgg tgacggtgtc gtggaactca ggcgccctga ccagcggcgt  600
gcacaccttc ccggctgtcc tacagtcctc aggactctac tccctcagca gcgtggtgac  660
cgtgccctcc agcagcttgg gcacccagac ctacatctgc aacgtgaatc acaagcccag  720
caacaccaag gtggacaaga gagttgagcc caaatcttgt gacaaaactc acacatgccc  780
accgtgccca gcacctgaac tcctgggggg accgtcagtc ttcctcttcc ccccaaaacc  840
caaggacacc ctcatgatct tccggacccc tgaggtcaca tgcgtggtgg tggacgtgag  900
cca                                                                903

SEQ ID NO: 16          moltype = DNA  length = 860
FEATURE                Location/Qualifiers
misc_feature           1..860
                       note = cDNA 25.10C HC variable region
source                 1..860
                       mol_type = other DNA
                       organism = synthetic construct
SEQUENCE: 16
ctcggttcta tcgattggct agcaccatgg agacagacac actcctgcta tgggtactgc  60
tgctctgggt tccaggttcc actggtgacc aggtgcagct gcaggagtct gggggaggcc  120
tggtcaagcc tggggggtcc ctgagactct cctgtacagc ctctggattc aacttcaata  180
aatataacat gaactgggtc cgccaggctc cagggaaggg gctggagtgg gtctcatcca  240
ttagtgctct tagcacttac atctattatg cagactcgct gaagggccga ttcaccgtct  300
ccagagacaa cgccaagaac tcactgtttc tgcaaatgaa cagcctgaga gacgacgaca  360
cggctgttta ttactgtgcg agagaaatac gacgtgccag tacctggtcc gccgacctct  420
ggggccgtgg cactctggtc actgtctcct cagcctccac caagggccca tcggtcttcc  480
ccctggcacc ctcctccaag agcacctctg ggggcacagc ggccctgggc tgcctggtca  540
aggactactt ccccgaaccg gtgacggtgt cgtggaactc aggcgccctg accagcggcg  600
tgcacacctt cccggctgtc ctacagtcct caggactcta ctccctcagc agcgtggtga  660
ccgtgccctc cagcagcttg ggcacccaga cctacatctg caacgtgaat cacaagccca  720
gcaacaccaa ggtggacaag agagttgagc ccaaatcttg tgacaaaact cacacatgcc  780
caccgtgccc agcacctgaa ctcctggggg gaccgtcagt cttcctcttc cctccaaacc  840
caaggacacc ctcatgatct                                              860

SEQ ID NO: 17          moltype = DNA  length = 716
FEATURE                Location/Qualifiers
misc_feature           1..716
                       note = cDNA 10.4B LC variable region
source                 1..716
                       mol_type = other DNA
                       organism = synthetic construct
SEQUENCE: 17
agctgtgacc ggcgcctacc tgagatcacc ggtgctagca ccatggagac agacacactc  60
ctgctatggg tactgctgct ctgggttcca ggttccactg gtgacgaaat tgtgttgaca  120
cagtctccat cctcactgtc tgcgtctgta ggagacagag tcaccatcac ttgtcgggcg  180
agtcgggaca tcaatactta tttaggttgg tttcagcaga gaccagggaa agcccctaag  240
tccctgatct atggtgcatc taatttgcaa aatggggtcc catcaaggtt cagcggcagt  300
ggatctggga cgtattttac tctcaccatc aacggcctgc agactgaaga ctttgcgact  360
tattattgcc aacaatatag catctacccg ctcagtctcg gcggagggac caaggcggac  420
atgaagcgaa ctgtggctgc accatctgtc ttcatcttcc cgccatctga tgagcagttg  480
aaatctggaa ctgcctctgt tgtgtgcctg ctgaataact tctatcccag agaggccaaa  540
gtacagtgga aggtggataa cgccctccaa tcgggtaact cccaggagag tgtcacagag  600
caggacagca aggacagcac ctacagcctc agcagcaccc tgacgctgag caaagcagac  660
tacgagaaac acaaagtcta cgcctgcgaa gtcacccatc agggcctgag ctcgcc      716

SEQ ID NO: 18          moltype = DNA  length = 906
FEATURE                Location/Qualifiers
misc_feature           1..906
                       note = cDNA 19.7E LC variable region
source                 1..906
                       mol_type = other DNA
                       organism = synthetic construct
SEQUENCE: 18
tcagctgtga ccggcgccta cctgagatca ccggtgctag caccatggag acagacacac  60
```

-continued

```
tcctgctatg gctcctgctg ctctgggttc caggttccac tggtgacgaa attgtgttga  120
cacagtctcc ttccaccctg tctgcatctg tgggagacag agtcaccatc acttgccggg  180
ccagtcagag tattaataat tggttggcct ggtatcagga gaaaccaggg aaagccccta  240
agctcctgat aaataaggcg tctagtttag aaagtggggt cccatcaagg ttcagcggca  300
gtggatctgg gacagaattc actctcacca tcaccagcct gcagcctgat gattttgcaa  360
cttattactg ccaacaatat aatagtaatt cgtggacgtt cggccaaggg accaaggtgg  420
acatgaaacg aactgtggct gcaccatctg tcttcatctt cccgccatct gatgagcagt  480
tgaaatctgg aactgcctct gttgtgtgcc tgctgaataa cttctatccc agagaggcca  540
aagtacagtg gaaggtggat aacgccctcc aatcgggtaa ctcccaggag agtgtcacag  600
agcaggacag caaggacagc acctacagcc tcagcagcac cctgacgctg agcaaagcag  660
actacgagaa acacaaagtc tacgcctgcg aagtcaccca tcagggcctg agctcgcccg  720
tcacaaagag cttcaacagg ggagagtgtt agagggagct agctcgacat gataagatac  780
attgatgagt ttgggacaac cacaactaga atgcagtgaa aaaaatgctt tatttgtgaa  840
atttgtgatg ctattgcttt tattgtgaaa tttgtgatgc tattgcttta tttgtaacca  900
ttataa                                                              906

SEQ ID NO: 19          moltype = DNA  length = 894
FEATURE                Location/Qualifiers
misc_feature           1..894
                       note = cDNA 2.9D LC variable region
source                 1..894
                       mol_type = other DNA
                       organism = synthetic construct
SEQUENCE: 19
actgcacctc ggttctatcg attggctagc accatgaaga cagacacact cctgctatgg  60
gtactgctgc tctgggttcc aggttccact ggtgacgaca ttgtgctgac ccagtctcca  120
gactccctgg ctgtgtctct gggcgagagg gccaccatca actgcaagtc cagccagagt  180
gttttataca gctccaacaa taagaactac ttagcttggt accagcagaa gccaggacag  240
cctcctaagc tgctcattta ctgggcatct acccgggaat ccggggtccc tgaccgattc  300
agtggcagcg ggtctgggac agatttcact ctcaccatca gcagcctgca ggctgaagat  360
gtggcagttt attactgtca gcaatattat agtactcctc cgacgttcgg ccaagggacc  420
aaggtggaaa tcaaacgaac tgtggctgca ccatctgtct tcatcttccc gccatctgat  480
gagcagttga aatctggaac tgcctctgtt gtgtgcctgc tgaataactt ctatcccaga  540
gaggccaaag tacagtggaa ggtggataac gccctccaat cgggtaactc ccaggagagt  600
gtcacagagc aggacagcaa ggacagcacc tacagcctca gcagcaccct gacgctgagc  660
aaagcagact acgagaaaca caaagtctac gcctgcgaag tcacccatca gggcctgagc  720
tcgcccgtca caaagagctt caacagggga gagtgttagg cggccgcaag cttggccgcc  780
atggcccaac ttgtttattg cagcttataa tggttacaaa taaagcaata gcatcacaaa  840
tttcacaaat aaagcatttt tttcactgca ttctagttgt ggtttgtcca actc        894

SEQ ID NO: 20          moltype = DNA  length = 903
FEATURE                Location/Qualifiers
misc_feature           1..903
                       note = cDNA 25.6A LC variable region
source                 1..903
                       mol_type = other DNA
                       organism = synthetic construct
SEQUENCE: 20
ctcggttcta tcgattggct agcaccatgg agacagacac actcctgcta tgggtactgc  60
tgctctgggt tccaggttcc actggtgacc tgcctgtgct gactcagcct gcctccgtgt  120
ctgggtctcc tggacagtcg atcaccatct cctgcactgg aaccagcagt gacgttggtg  180
cttataacta tgtctcctgg taccaacagc acccaggcaa agcccccaaa ctcataattt  240
atgaagtcaa gattcggccg tcaggggtgt ctaatcgttt ctctggctcc aagtctggca  300
acacggcctc cctgaccatc tctgggctcc aggctgagga cgaggctgat tatttttgca  360
gctcatattc aaccaacagc ccttgggtgt tcggcggagg gacgaaggtg accgtcctac  420
gtcagcccaa ggctgccccc tcggtcactc tgttcccacc ctcctctgag gagcttcaag  480
ccaacaaggc cacactggtg tgtctcataa gtgacttcta cccgggagcc gtgacagtgg  540
cctggaaggc agatagcagc cccgtcaagg cgggagtgga gaccaccaca ccctccaaac  600
aaagcaacaa caagtacgcg gccagcagct acctgagcct gacgcctgag cagtggaagt  660
cccacagaag ctacagctgc caggtcacgc atgaagggag caccgtggag aagacagtgg  720
cccctacaga atgttcatga gcggccgcaa gcttggccgc catggcccaa cttgtttatt  780
gcagcttata atggttacaa ataaagcaat agcatcacaa atttcacaaa taaagcattt  840
ttttcactgc attctagttg tggtttgtcc aaactcatca atgtatctta tcatgtctgg  900
atc                                                                 903

SEQ ID NO: 21          moltype = DNA  length = 900
FEATURE                Location/Qualifiers
misc_feature           1..900
                       note = cDNA 36.1F LC variable region
source                 1..900
                       mol_type = other DNA
                       organism = synthetic construct
SEQUENCE: 21
tccaggtcac tgcacctcgg ttctatcgat tggctagcac catggagaca gacacactcc  60
tgctatgggt actgctgctc tgggttccag gttccactgg tgacgaaatt gtgctgacac  120
agtctccagg caccctgtct ttgtctccag gggaaagagc caccctctcc tgcagggcca  180
gtcagagtgt tactaaaaac tacttagcct ggtaccagca gaaacctggc caggctccca  240
ccctcgtcat ctatgatgca tccaccaggg ccagtggcat cccagacagg ttcattggca  300
gtgggtctgg gacagacttc actctcacca tcagcagact ggagcctgaa gattttgcag  360
```

-continued

```
tatattactg ccaccagtat ggcagctcac ctccgtacac ttttggccgg gggaccaagc  420
tggagatcaa acgaactgtg gctgcaccat ctgtcttcat cttcccgcca tctgatgagc  480
agttgaaatc tggaactgcc tctgttgtgt gcctgctgaa taacttctat cccagagagg  540
ccaaagtaca gtggaaggtg gataacgccc tccaatcggg taactcccag gagagtgtca  600
cagagcagga cagcaaggac agcacctaca gcctcagcag caccctgacg ctgagcaaag  660
cagactacga gaaacacaaa gtctacgcct gcgaagtcac ccatcagggc ctgagctcgc  720
ccgtcacaaa gagcttcaac aggggagagt gttaggcggc cgcaagcttg gccgccatgg  780
cccaacttgt ttattgcagc ttataatggt tacaaataaa gcaatagcat cacaaatttc  840
acaaataaag catttttttc actgcattct agttgtgggt tgtccaaact catcaatgta  900

SEQ ID NO: 22          moltype = DNA  length = 922
FEATURE                Location/Qualifiers
misc_feature           1..922
                       note = cDNA 36.9F LC variable region
source                 1..922
                       mol_type = other DNA
                       organism = synthetic construct
SEQUENCE: 22
aggtcactgc acctcggttc tatcgattgg ctagcaccat ggagacagac acactcctgc  60
tatgggtact gctgctctgg gttccaggtt ccactggtga cgacatcgtg atgacccagt  120
ctccagactc cctggctgtg tctctgggcg agagggccac catcaactgc aagtccagcc  180
agactgtttt gttcacctcc tattacgtag cttggtatca acaaaagcca gggcagccgc  240
ctaagttgct cttttccggg gcctcttctc gggaatccgg ggtccctgac cgattcagtg  300
ccggcgggtc tgggacagat ttctatctca ccatcaacag cctgcaggct gaagatgtgg  360
cagattacta ttgtcagcaa tatcatactc ctcctttcac tttcggcgga gggaccaagc  420
tggagatcag acgaactgtg gctgcaccat ctgtcttcat cttcccgcca tctgatgagc  480
agttgaaatc tggaactgcc tctgttgtgt gcctgctgaa taacttctat cccagagagg  540
ccaaagtaca gtggaaggtg gataacgccc tccaatcggg taactcccag gagagtgtca  600
cagagcagga cagcaaggac agcacctaca gcctcagcag caccctgacg ctgagcaaag  660
cagactacga gaaacacaaa gtctacgcct gcgaagtcac ccatcagggc ctgagctcgc  720
ccgtcacaaa gagcttcaac aggggagagt gttaggcggc cgcaagcttg gccgccatgg  780
cccaacttgt ttattgcagc ttataatggt tacaaataaa gcaatagcat cacaaatttc  840
acaaataaag catttttttc actgcattct agttgtggtt tgtccaaact catcaatgta  900
tcttatcatg tctggatcgg ga                                           922

SEQ ID NO: 23          moltype = DNA  length = 858
FEATURE                Location/Qualifiers
misc_feature           1..858
                       note = cDNA 37.2D LC variable region
source                 1..858
                       mol_type = other DNA
                       organism = synthetic construct
SEQUENCE: 23
tcactgcacc tcggttctat cgattggcta gcaccatgga gacagacaca ctcctgctat  60
gggtactgct gctctgggtt ccaggttcca ctggtgacga aacgacactc acgcagtctc  120
cagccaccct gtctgtgtct ccaggggaaa cagccaccct ctcctgcagg gccagtcaaa  180
atgttatcaa caacttagcc tggtaccagc agaaacctgg ccaggctccc aggctcctca  240
tttatggtgc atccaccagg gccactggta tcccagccag gttcagtggc agtgggtctg  300
ggacagagtt cactctcacc atcagcagca tgcagtctga agattttgca gtttattact  360
gtcagcaata taatgactgg cctcgaagtt ttggccaggg gaccaggctg gacatcagac  420
gaactgtggc tgcaccatct gtcttcatct tcccgccatc tgatgagcag ttgaaatctg  480
gaactgcctc tgttgtgtgc ctgctgaata acttctatcc cagagaggcc aaagtacagt  540
ggaaggtgga taacgccctc caatcgggta actcccagga gagtgtcaca gagcaggaca  600
gcaaggacag cacctacagc ctcagcagca ccctgacgct gagcaaagca gactacgaga  660
aacacaaagt ctacgcctgc gaagtcaccc atcagggcct gagctcgccc gtcacaaaga  720
gcttcaacag gggagagtgt taggcggccg caagcttggc cgccatggcc caacttgttt  780
attgcagctt ataatggtta caaataaagc aatagcatca caaatttcac aaataaagca  840
tttttttcac tgcattct                                               858

SEQ ID NO: 24          moltype = DNA  length = 958
FEATURE                Location/Qualifiers
misc_feature           1..958
                       note = cDNA 37.7G LC variable region
source                 1..958
                       mol_type = other DNA
                       organism = synthetic construct
SEQUENCE: 24
tccaggtcac tgccctcggt tctatcgatt ggctagcacc atggagacag acacactcct  60
gctatgggta ctgctgctct gggttccagg ttccactggt gacgacattg tgctgaccca  120
gtctccaggc accctgtctt tgtctccagg ggaaagagcc accctctcct gcagggccag  180
tcagagtgtg aacagcatct tcttagcctg gtaccagcag aaacctggcc aggctcccag  240
gctcctcatc tatggtgcat ccagcagggc cactggcatc ccagacaggt tcagtggcag  300
tgggtctggg acagacttca ctctcaccat cagcagactg gagcctgagg attttgcagt  360
gtattactgt cagcagtatc atagctcacc taagctcact ttcggcggag ggaccaaggt  420
ggagatcaaa cgaactgtgg ctgcaccatc tgtcttcatc ttcccgccat ctggtgagca  480
gttgaaatct ggaactgcct ctgttgtgtg cctgctgaat aacttctatc ccagagaggc  540
caaagtacag tggaaggtgg ataacgccct ccaatcgggt aactcccagg agagtgtcac  600
agagcaggac agcaaggaca gcacctacag cctcagcagc accctgacgc tgagcaaagc  660
agactacgag aaacacaaag tctacgcctg cgaagtcacc catcagggcc tgagctcgcc  720
```

```
cgtcacaaag agcttcaaca ggggagagtg ttaggcggcc gcaagcttgg ccgccatggc  780
ccaacttgtt tattgcagct tataatggtt acaaataaag caatagcatc acaaatttca  840
caaataaagc atttttttca ctgcattcta gttgtggttt gtccaaactc atcaatgtat  900
cttatcatgt ctggatcggg aattaattcg gcgcagcacc atggcctgaa ataacctc    958

SEQ ID NO: 25          moltype = DNA  length = 1015
FEATURE                Location/Qualifiers
misc_feature           1..1015
                       note = cDNA 37.7H LC variable region
source                 1..1015
                       mol_type = other DNA
                       organism = synthetic construct
SEQUENCE: 25
tcactgcacc tcggttctat cgattggcta gcaccatgga gacagacaca ctcctgctat  60
gggtactgct gctctgggtt ccaggttcca ctggtgacca gtctgccctg actcagcctg  120
cctccgtgtc tgggtctcct ggacagtcga tcaccatctc ctgcactgga accggcagtg  180
acattggtgg ttataacttt gtctcctggt accaacagta tcccggcaaa gcccccaaac  240
tcattattta tgaggtccgt attcgggcct caggggtttc caatcgcttc tctggctcca  300
agtctggcaa cacggcctcc ctgaccatct ctggactcca ggctgaggac gaggctgatt  360
attactgcaa ctcatattca atccacagcc cttgggtgtt cggcggaggg accaagttga  420
ccgtcctgcg tcagcccaag gctgccccct cggtcactct gttcccaccc tcctctgagg  480
agcttcaagc caacaaggcc acactggtgt gtctcataag tgacttctac ccgggagccg  540
tgacagtggc ctggaaggca gatagcagcc ccgtcaaggc gggagtggag accaccacac  600
cctccaaaca aagcaacaac aagtacgcgg ccagcagcta cctgagcctg acgcctgagc  660
agtgggagtc ccacagaagc tacagctgcc aggtcacgca tgaagggagc accgtggaga  720
agacagtggc ccctacagaa tgttcatgag cggccgcaag cttggccgcc atggcccaac  780
ttgtttattg cagcttataa tggttacaaa taaagcaata gcatcacaaa tttcacaaat  840
aaagcatttt tttcactgca ttctagttgt ggtttgtcca aactcatcaa tgtatcttat  900
catgtctgga tcgggaatta attcggcgca gcaccatggc ctgaaatacc ctctgaaaga  960
ggaacttggt taggtacctt ctgaggcgga aagaaccatc tgtggaatgt gtgtc       1015

SEQ ID NO: 26          moltype = DNA  length = 910
FEATURE                Location/Qualifiers
misc_feature           1..910
                       note = cDNA 8.9F LC variable region
source                 1..910
                       mol_type = other DNA
                       organism = synthetic construct
SEQUENCE: 26
cactgccctc ggttctatcg attggctagc accatggaga cagacacact cctgctatgg  60
gtactgctgc tctgggttcc aggttccact ggtgaccagg cagggctgac tcagcctgcc  120
tccgtgtctg ggtctcctgg acagtcgatc accatctcct gcactgcagc caacagtgac  180
attggtgatt ttaactttgt ctcctggtac caacagcgcc cagacaaagc ccccaaactc  240
atggtttatg aggtcagcag tcggccctca ggggtttcta atcgcttctc tggctccaag  300
tctggcaaca cggcctccct gaccatctct gggctccagg ctgaggacga ggctgattat  360
tactgcacct catatacaag cagcagcact tttgtcttcg gaactgggac caaggtcacc  420
gtcctaggtc agcccaaggc caaccccact gtcactctgt tcccgccctc ctctgaggag  480
cttcaagcca acaaggccac actggtgtgt ctcataagtg acttctaccc gggagccgtg  540
acagtggcct ggaaggcaga tagcagcccc gtcaaggcgg gagtggagac caccacaccc  600
tccaaacaaa gcaacaacaa gtacgcggcc agcagctacc tgagcctgac gcctgagcag  660
tggaagtccc acagaagcta cagctgccag gtcacgcatg aagggagcac cgtggagaag  720
acagtggccc ctacagaatg ttcatgagcg gccgcaagct tggccgccat ggcccaactt  780
gtttattgca gcttataatg gttacaaata aagcaatagc atcacaaatt tcacaaataa  840
agcatttttt tcactgcatt ctagttgtgg tttgtccaaa ctcatcaatg tatcttatca  900
tgtctggatc                                                         910

SEQ ID NO: 27          moltype = DNA  length = 908
FEATURE                Location/Qualifiers
misc_feature           1..908
                       note = cDNA NE13 LC variable region
source                 1..908
                       mol_type = other DNA
                       organism = synthetic construct
SEQUENCE: 27
ctcccaggtc actgcacctc ggttctatcg attggctagc accatggaga cagacacact  60
cctgctatgg gtactgctgc tctgggttcc aggttccact ggtgacgaaa cgacactcac  120
gcagtctcca ggcaccctgt ctttgtctcc aggggaaaga gccaccctct cctgcagggc  180
cagtcagagt gttagcagca cctacttagc ctggtaccag cagaaacctg gccagtctcc  240
caggctcctc atttatggtg catccagtag ggccactggc atcccagaca ggttcagtgg  300
cagtgggtct gggacacagt tcactctcac catcaacaga ctggagcctg aagattttgc  360
agtgtattac tgtcagcagt ttggtagccc gtggacattc ggccaaggga ccaaggtgga  420
aatcaaacga actgtggctg caccatctgt cttcatcttc ccgccatctg atgagcagtt  480
gaaatctgga actgcctctg ttgtgtgcct gctgaataac ttctatccca gagaggccaa  540
agtacagtgg aaggtggata acgccctcca atcgggtaac tcccaggaga gtgtcacaga  600
gcaggacagc aaggacagca cctacagcct cagcagcacc ctgacgctga gcaaagcaga  660
ctacgagaaa cacaaagtct acgcctgcga agtcacccat cagggcctga gctcgcccgt  720
cacaaagagc ttcaacaggg gagagtgtta ggcggccgca agcttggccg ccatggccca  780
acttgtttat tgcagcttat aatggttaca aataaagcaa tagcatcaca aatttcacaa  840
ataaagcatt tttttcactg cattctagtt gtggtttgtc caaactcatc aatgtatctt  900
```

-continued

```
atcatgtc                                                              908

SEQ ID NO: 28          moltype = DNA  length = 932
FEATURE                Location/Qualifiers
misc_feature           1..932
                       note = cDNA 12.1F LC variable region
source                 1..932
                       mol_type = other DNA
                       organism = synthetic construct
SEQUENCE: 28
gtcactgcac ctcggttcta tcgattggct agcaccatgg agacagacac actcctgcta  60
tgggtactgc tgctctgggt tccaggttcc actggtgacg aaacgacact cacgcagtct  120
ccagccaccc tgtctttgtc tccaggggag agagccaccc tctcctgtag ggccagtcag  180
agtgttagca gctacttagc ctggtaccaa cacaaacctg gccaggctcc caggctcctc  240
atctatggtg catcaaagag ggccactggc atcccgtcca ggttcagtgg cagtgggtct  300
gggacagact tcagtctcac catcagcagc ctagagcctg aagattttgc agtttactac  360
tgtcagcacc gaagcgactg gcggactacc ttcggccaag ggacacgact ggagattaaa  420
cgaactgtgg ctgcaccatc tgtcttcatc ttcccgccat ctgatgagca gttgaaatct  480
ggaactgcct ctgttgtgtg cctgctgaat aacttctatc ccagagaggc caaagtacag  540
tggaaggtgg ataacgccct ccaatcgggt aactcccagg agagtgtcac agagcaggac  600
agcaaggaca gcacctacag cctcagcagc accctgacgc tgagcaaagc agactacgag  660
aaacacaaag tctacgcctg cgaagtcacc catcagggcc tgagctcgcc cgtcacaaag  720
agcttcaaca ggggagagtg ttaggcggcc gcaagcttgg ccgccatggc ccaacttgtt  780
tattgcagct tataatggtt acaaataaag caatagcatc acaaatttca caaataaagc  840
atttttttca ctgcattcta gttgtggttt gtccaaactc atcaatgtat cttatcatgt  900
ctggatcggg aaattaatcg gcgcagcacc at                                932

SEQ ID NO: 29          moltype = DNA  length = 895
FEATURE                Location/Qualifiers
misc_feature           1..895
                       note = cDNA 9.8A LC variable region
source                 1..895
                       mol_type = other DNA
                       organism = synthetic construct
SEQUENCE: 29
ggttctatcg attggctagc accatggaga cagacacact cctgctatgg gtactgctgc  60
tctgggttcc aggttccact ggtgacgaca tcgtgatgac ccagtctcct tccaccctgt  120
ctgcatctgt aggagacaga gtcaccatca cttgccgggc cagtcagagt attgataggt  180
ggttggcctg gtatcagcag aaaccaggga aagcccctaa gctcctgatc tatcaggcat  240
ctagtttaga aagaggggtc ccatcaaggt tcagcggcag tggatctggg acagaattca  300
ctctcaccat cagcagcctg cagcccgatg attttgcaac ttattactgc caacagtata  360
atggttaccc tctcactttc ggcggaggga ccaaggtgga gatcaaacga actgtggctg  420
caccatctgt cttcatcttc ccgccatctg atgagcagtt gaaatctgga actgcctctg  480
ttgtgtgcct gctgaataac ttctatccca gagaggccaa agtacagtgg aaggtggata  540
acgccctcca atcgggtaac tcccaggaga gtgtcacaga gcaggacagc aaggacagca  600
cctacagcct cagcagcacc ctgacgctga gcaaagcaga ctacgagaaa cacaaagtct  660
acgcctgcga agtcacccat cagggcctga gctcgcccgt cacaaagagc ttcaacaggg  720
gagagtgtta ggcggccgca agcttggccg ccatggccca acttgtttat tgcagcttat  780
aatggttaca aataaagcaa tagcatcaca aatttcacaa ataaagcatt tttttcactg  840
cattctagtt gtggtttgtc caaactcatc aatgtatctt atcatgtctg gatcg       895

SEQ ID NO: 30          moltype = DNA  length = 784
FEATURE                Location/Qualifiers
misc_feature           1..784
                       note = cDNA 18.5C LC variable region
source                 1..784
                       mol_type = other DNA
                       organism = synthetic construct
SEQUENCE: 30
tccaggtcca ctgcacctcg gttctatcga ttggctagca ccatggagac agacacactc  60
ctgctatggg tactgctgct ctgggttcca ggttccactg gtgacgacat ccagatgacc  120
cagtctccag gcaccctgtc tttgtctcca ggggaaagag ccaccctctc ctgcagggcc  180
agtcagagtg ttatcagtta ctacgtagcc tggtaccagc acaaaggtgg ccaggctccc  240
aggctcctca tttatggtgc atccagcagg gccactggcg tcccagacag gttcagtggc  300
agtgggtctg ggacagactt cactctcacc atcagcagcc tggagcctga agattttgca  360
ctgtattact gtcagtacta tgggagctca cctctgtggg cgttcggcca agggaccaag  420
gtggaaatca aacgaactgt ggctgcacca tctgtcttca tcttcccgcc atctgatgag  480
cagttgaaat ctggaactgc ctctgttgtg tgcctgctga ataacttcta tcccagagag  540
gccaaagtac agtggaaggt ggataacgcc ctccaatcgg gtaactccca ggagagtgtc  600
acagagcagg acagcaagga cagcacctac agcctcagca gcaccctgac gctgagcaaa  660
gcagactacg agaaacacaa agtctacgcc tgcgaagtca cccatcaggg cctgagctcg  720
cccgtcacaa agagcttcaa caggggagag tgttaggcgg ccgcaagctt ggccgccatg  780
gccc                                                               784

SEQ ID NO: 31          moltype = DNA  length = 845
FEATURE                Location/Qualifiers
misc_feature           1..845
                       note = cDNA 8.11G LC variable region
source                 1..845
```

-continued

```
                         mol_type = other DNA
                         organism = synthetic construct
SEQUENCE: 31
cggttctatc gattggctag caccatggag acagacacac tcctgctatg ggtactgctg  60
ctctgggttc caggttccac tggtgacgaa attgtgctga ctcagtctcc agccaccctg  120
tctgtgtctc cagggggtag ggcctccctc tcctgccggg ccagtcagag tattggcgac  180
aagttatcct ggtatcagca gaaacctggg caggctccca ggctcgtcat ctatggtgca  240
tataccaggg ccactgatat ctcacccagg ttcagtggca gtaggtctgg gacagacttc  300
aatctcacca tcagcagaat gcagtctgga gactttgcag tttatttctg tcagcagtat  360
gaaaactggc ctcggacttt tggccagggg accaagctgg agatcaaacg aactgtggct  420
gcaccatctg tcttcatctt cccgccatct gatgagcagt tgaaatctgg aactgcctct  480
gttgtgtgcc tgctgaataa cttctatccc agagaggcca aagtacagtg gaaggtggat  540
aacgccctcc aatcgggtaa ctcccaggag agtgtcacag agcaggacag caaggacagc  600
acctacagcc tcagcagcac cctgacgctg agcaaagcag actacgagaa acacaaagtc  660
tacgcctgcg aagtcaccca tcagggcctg agctcgcccg tcacaaagag cttcaacagg  720
ggagagtgtt aggcggccgc aagcttggcc gccatggccc aacttgttta ttgcagctta  780
taatggttac aaataaagca atagcatcac aaatttcaca aataaagcat ttttttcact  840
gcatt                                                              845

SEQ ID NO: 32            moltype = DNA  length = 900
FEATURE                  Location/Qualifiers
misc_feature             1..900
                         note = cDNA 25.10C LC variable region
source                   1..900
                         mol_type = other DNA
                         organism = synthetic construct
SEQUENCE: 32
cctcggttct atcgattggc tagcaccatg gagacagaca cactcctgct atgggtactg  60
ctgctctggg ttccaggttc cactggtgac gacatccaga tgacccagtc tccatcctcc  120
ctgtctgcat ctgttggaga cagagtcatc atcacttgcc gggcaagtca gagcatcagc  180
agctctttaa attggtatca gcagaaacca gggaaagccc ctaagctcct gatctatgct  240
gcagtcaatt tggagactgg ggtcccgtca aggttcagtg gcagtggatt tgggacagat  300
ttcactctcg ccatcagcaa tgtgcaacct gaagattttg caacttacta ctgtcaacag  360
agcgatactc ggacttttgg ccgggggacc aagctggacg tcaaacgaac tgtggctgca  420
ccatctgtct tcatcttccc gccatctgat gagcagttga aatctggaac tgcctctgtt  480
gtgtgcctgc tgaataactt ctatcccaga gaggccaaag tacagtggaa ggtggataac  540
gccctccaat cgggtaactc ccaggagagt gtcacagagc aggacagcaa ggacagcacc  600
tacagcctca gcagcaccct gacgctgagc aaagcagact acgagaaaca caaagtctac  660
gcctgcgaag tcacccatca gggcctgagc tcgcccgtca caaagagctt caacagggga  720
gaagtgttag gcggccgcaa gcttggccgc catggcccaa cttgtttatt gcagcttata  780
atggttacaa ataaagcaat agcatcacaa atttcacaaa taaagcattt ttttcactgc  840
attctagttg tggtttgtcc aaactcatca atgtatctta tcatgtctgg atcgggaatt  900

SEQ ID NO: 33            moltype = AA  length = 203
FEATURE                  Location/Qualifiers
REGION                   1..203
                         note = HC variable region
source                   1..203
                         mol_type = protein
                         organism = synthetic construct
SEQUENCE: 33
METDTLLLWV LLLWVPGSTG DQVQLVQSGG GVVQPGRSLR VSCVTSGFNF RAYGMHWVRQ  60
IPGKGLEWVA DIWSAETNRH YADSVKGRFT ISRDNSKSTL YLQMNSLRAE DTGVYFCAKA  120
RPGYDYVVDL WGQGTLVIVS SASTKGPSVF PLAPCSRSTS GGTAALGCLV KDYFPEPVTV  180
SWNSGALTSG VHTFPAVLQS SGL                                          203

SEQ ID NO: 34            moltype = AA  length = 258
FEATURE                  Location/Qualifiers
REGION                   1..258
                         note = HC variable region
source                   1..258
                         mol_type = protein
                         organism = synthetic construct
SEQUENCE: 34
METDTLLLWV LLLWVPGSTG DEVQLVESGG GLVRPGGSLR LSCAASGFSF SSYSMHWVRH  60
VPGKGLVWVS YINSDGSTKI YADSVKGRFS ISRDNAKNKL YLQMDSLRVE DTAVYSCVRL  120
VHYDWSPFVW GQGTLVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKKVEP  240
QSCDKTHTCP PCPAPELL                                                258

SEQ ID NO: 35            moltype = AA  length = 294
FEATURE                  Location/Qualifiers
REGION                   1..294
                         note = HC variable region
source                   1..294
                         mol_type = protein
                         organism = synthetic construct
SEQUENCE: 35
METDTLLLWV LLLWVPGSTG DEVQLVESGG GLVKPGGSLR LSCAASGFTF TRFTLTWVRQ  60
```

-continued

```
APGKGLEWVS SISSGSSDIN YADSVKGRFT ISRDNARNSL FLQMSSLRVD DTAVYYCAKD  120
PRSGISGRYG MDVWGQGTTV IVSSASTKGP SVFPLAPCSR STSGGTAALG CLVKDYFPEP  180
VTVSWNSGAL TSGVHTFPAV LQSSGLYSLS SVVTVPSSSL GTQTYICNVN HKPSNTKVDK  240
RVEPKSCDKT HTCPPCPAPE LLGGPSVFLF PPKPKDTLMI SRTPEVTCVV VDVS        294

SEQ ID NO: 36          moltype = AA  length = 171
FEATURE                Location/Qualifiers
REGION                 1..171
                       note = HC variable region
source                 1..171
                       mol_type = protein
                       organism = synthetic construct
SEQUENCE: 36
METDTLLLWV LLLWVPGSTG DQVQLQESGG GLVKAGGSLR LSCAASGFMF ERYSLHWVRQ  60
TPGKGLEWVS SISSLSGSHI NYADSVKGRF TISRDNAKNS LSLQMNSLRV EDTAIYYCAR  120
DRRSGSSPVP LDVWGQGTTV TVSSASTKGP SVFPLAPSSK STSGGTAALG C           171

SEQ ID NO: 37          moltype = AA  length = 274
FEATURE                Location/Qualifiers
VARIANT                274
                       note = X can be any amino acid
source                 1..274
                       mol_type = protein
                       organism = synthetic construct
REGION                 1..274
                       note = HC variable region
SEQUENCE: 37
METDTLLLWV LLLWVPGSTG DQVQLQESGA GLVKPSETLS LTCAVSGGPF SGAYWTWIRQ  60
TPGKGLEWIG EAGRSGTTNY NPSLKSRVTI SLDTSKSQFS LKLTSVTAAD TAVYFCGRRQ  120
IMSLSNLYKR PVDSWGRGTP VIVSSASTKG PSVFPLAPSS KSTSGGTAAL GCLVKDYFPE  180
PVTVSWNSGA LTSGVHTFPA VLQSSGLYSL SSVVTVPSSS LGTQTYICNV NHKPSNTKVD  240
KRVEPKSCDK THTCPPCPAP ELLGGPSVFL FPPX                              274

SEQ ID NO: 38          moltype = AA  length = 279
FEATURE                Location/Qualifiers
REGION                 1..279
                       note = HC variable region
source                 1..279
                       mol_type = protein
                       organism = synthetic construct
SEQUENCE: 38
METDTLLLWV LLLWVPGSTG DEVQLVQSGG GLVKAGGSLK LSCGASGFTF SSYSMSWVRQ  60
APGKGLEWVS YISSGGSSIH YADSVKGRFT ISRDNAKNSL YLQMKNLRVD DTGRYYCVRD  120
PRSGISGRYG MDVWGQGTTV TVSSASTKGP SVFPLAPSSK STSGGTAALG CLVKDYFPEP  180
VTVSWNSGAL TSGVHTFPAV LQSSGLYSLS SVVTVPSSSL GTQTYICNVN HKPSNTKVDK  240
RVEPKSCDKT HTCPPCPAPE LLGGPSVFLF PPNPRTPSS                         279

SEQ ID NO: 39          moltype = AA  length = 275
FEATURE                Location/Qualifiers
REGION                 1..275
                       note = HC variable region
source                 1..275
                       mol_type = protein
                       organism = synthetic construct
SEQUENCE: 39
METDTLLLWV LLLWVPGSTG DEVQLVQSGA EVKKPGASVK VSCKASGYTF TKYGISWVRQ  60
APGQGLEWMG WISAFNGYTR YGQRFQGKVT MTTDTSTNTA SLEVRTLTSN DTAVYYCARQ  120
YPDQYSSSGW PRLFAMDVWG QGTTVIVSPA STKGPSVFPL APSSKSTSGG TAALGCLVKD  180
YFPEPVTVSW NSGALTSGVH TFPAVLQSSG LYSLSSVVTV PSSSLGTQTY ICNVNHKPSN  240
TKVDKRVEPK SCDKTHTCPP CPAPELLGGP SVFLF                             275

SEQ ID NO: 40          moltype = AA  length = 309
FEATURE                Location/Qualifiers
REGION                 1..309
                       note = HC variable region
source                 1..309
                       mol_type = protein
                       organism = synthetic construct
SEQUENCE: 40
METDTLLLWV LLLWVPGSTG DEVQLVESGG GLVKPGGSRR LSCAASGFTF SRDTMTWVRQ  60
APGKGLEWVA SISSGSSDIN YADSVKGRFT ISRDNGKNSL YLHMNSLRAD DTAIYYCARD  120
PRSGISGRYG MDVWGQGTTV TVSSASTKGP SVFPLAPSSK STSGGTAALG CLVKDYFPEP  180
VTVSWNSGAL TSGVHTFPAV LQSSGLYSLS SVVTVPSSSL GTQTYICNVN HKPSNTKVDK  240
RVEPKSCDKT HTCPPCPAPE LLGGPSVFLF PPKPKDTLMI SRTPEVTCVV VDVSHEDPEV  300
KFNWYVDGV                                                          309

SEQ ID NO: 41          moltype = AA  length = 296
FEATURE                Location/Qualifiers
REGION                 1..296
```

-continued

```
                         note = HC variable region
source                   1..296
                         mol_type = protein
                         organism = synthetic construct
SEQUENCE: 41
METDTLLLWV LLLWVPGSTG DEVQLVQSGG GLVKAGGSLR LSCAASGFTF STYSMNWIRQ  60
APGKGLEWVA SISSRSGSHI NYVDSVKGRF TISRDNARDL LYLQMNSLRV DDSALYYCAR  120
DRRSGTSPLP LDVWGQGTTV TVFSASTKGP SVFPLAPSSK STSGGTAALG CLVKDYFPEP  180
VTVSWNSGAL TSGVHTFPAV LQSSGLYSLS SVVTVPSSSL GTQTYICNVN HKPSNTKVDK  240
RVEPKSCDKT HTCPPCPAPE LLGGPSVFLF PPKPKDTLMI SRTPEVTCVV VDVSHE      296

SEQ ID NO: 42            moltype = AA  length = 295
FEATURE                  Location/Qualifiers
VARIANT                  295
                         note = X can be any amino acid
source                   1..295
                         mol_type = protein
                         organism = synthetic construct
REGION                   1..295
                         note = HC variable region
SEQUENCE: 42
METDTLLLWV LLLWVPGSTG DQGTLRESGP GLVRPSETLS LTCGVSGYSI SSGYYWGWIR  60
QPPGKGLEWI GNIYRSGSTY YNPSLKSRVT VSIDTSKNQF SLKLNSVTAA DTAVYYCARS  120
GIKVADDYYY EMDVWGQGTD DYSYAMDVWG QGTTVTVSSA STKGPSVFPL APSSKSTSGG  180
TAALGCLVKD YFPEPVTVSW NSGALTSGVH TFPAVLQSSG LYSLSSVVTV PSSSLGTQTY  240
ICNVNHKPSN TKVDKRVEPK SCDKTHTCPP CPAPELLGGP SVFLFPPKPK DTLMX       295

SEQ ID NO: 43            moltype = AA  length = 283
FEATURE                  Location/Qualifiers
REGION                   1..283
                         note = HC variable region
source                   1..283
                         mol_type = protein
                         organism = synthetic construct
SEQUENCE: 43
METDTLLLWV LLLWVPGSTG DEVQLVESGG GLVKPGGSLR LSCVASGFTF SSYSMNWVRQ  60
APGKGLEWVS SISSGSSYIE YADSVKGRLT ISRDNAKKSL YLQLNSLRAE DTAVYYCARH  120
TARIDSYHGM DVWGQGTTVT VSSASTKGPS VFPLAPSSKS TSGGTAALGC LVKDYFPEPV  180
TVSWNSGALT SGVHTFPAVL QSSGLYSLSS VVTVPSSSLG TQTYICNVNH KPSNTKVDKR  240
VEPKSCDKTH TCPPCPAPEL LGGPSVFLFP PKPKDTLMIS RTP                    283

SEQ ID NO: 44            moltype = AA  length = 295
FEATURE                  Location/Qualifiers
VARIANT                  271
                         note = X can be any amino acid
source                   1..295
                         mol_type = protein
                         organism = synthetic construct
REGION                   1..295
                         note = HC variable region
SEQUENCE: 44
METDTLLLWV LLLWVPGSTG DQVQLQESGA GLLKPSETLS LSCTVDGESF NGFFWTWIRQ  60
PPGKGLEWIG EINHLASTGY NPSLKSRVTI SVDTSKNQFS LKLTSVTAAD TAVYYCARGY  120
SYGFAWPNYH YLDVWGKGTT VTVSSASTKG PSVFPLAPSS KSTSGGTAAL GCLVKDYFPE  180
PVTVSWNSGA LTSGVHTFPA VLQSSGLYSL SSVVTVPSSS LGTQTYICNV NHKPSNTKVD  240
KRVEPKSCDK THTCPPCPAP ELLGGPSVFL XPPKPKDTLM ISRTPEVTCV VVDVS       295

SEQ ID NO: 45            moltype = AA  length = 283
FEATURE                  Location/Qualifiers
REGION                   1..283
                         note = HC variable region
source                   1..283
                         mol_type = protein
                         organism = synthetic construct
SEQUENCE: 45
METDTLLLWV LLLWVPGSTG DEVQLVQSGG RLVQPGGSLR LSCVASGFTF SSHAMSWVRQ  60
APGKGLEWVS GFSGSSGTTK YADSVKGRFT ISRDNSKKTL YLQMNSLRAE DTAVYYCAKG  120
FSPFRGVQFP YFDYWGQGTL VTVSSASTKG PSVFPLAPSS KSTSGGTAAL GCLVKDYFPE  180
PVTVSWNSGA LTSGVHTFPA VLQSSGLYSL SSVVTVPSSS LGTQTYICNV NHKPSNTKVD  240
KRVEPKSCDK THTCPPCPAP ELLGGPSVFL FPPKPRTPSS PGP                    283

SEQ ID NO: 46            moltype = AA  length = 287
FEATURE                  Location/Qualifiers
REGION                   1..287
                         note = HC variable region
source                   1..287
                         mol_type = protein
                         organism = synthetic construct
SEQUENCE: 46
```

-continued

```
METDTLLLWV LLLWVPGSTG DEVQLVESGG GLVRPGGSLR LSCAAAGFTF KSYSMNWVRQ  60
APGRGLEWVS SITSGGSKTY YADVVKGRFT VSRDNAKQSL YLQMNSLRAE DTAIYFCARS  120
LHSTSQPSYM DVWGRKITVI VSSASTKGPS VFPLAPSSKS TSGGTAALGC LVKDYFPEPV  180
TVSWNSGALT SGVHTFPAVL QSSGLYSLSS VVTVPSSSLG TQTYICNVNH KPSNTKVDKR  240
VEPKSCDKTH TCPPCPAPEL LGGPSVFLFP PKPKDTLMIS RTPEVTC                287

SEQ ID NO: 47          moltype = AA  length = 290
FEATURE                Location/Qualifiers
REGION                 1..290
                       note = HC variable region
source                 1..290
                       mol_type = protein
                       organism = synthetic construct
SEQUENCE: 47
METDTLLLWV LLLWVPGSTG DQVQLQESGP GLVKPSETLS LTCSISGVST RNYYWSWIRQ  60
SPGKGLEWIG YIFNIGTTNY NPSLKSRLTI SVDTSKNQFS LKITSVTAAD TAVYYCASGF  120
EYGDYTFDYW GQGTPVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKRVEP  240
KSCDKTHTCP PCPAPELLGG PSVFLFPPKP KDTLMIFRTP EVTCVVVDVS             290

SEQ ID NO: 48          moltype = AA  length = 276
FEATURE                Location/Qualifiers
REGION                 1..276
                       note = HC variable region
source                 1..276
                       mol_type = protein
                       organism = synthetic construct
SEQUENCE: 48
METDTLLLWV LLLWVPGSTG DQVQLQESGG GLVKPGGSLR LSCTASGFNF NKYNMNWVRQ  60
APGKGLEWVS SISALSTYIY YADSLKGRFT VSRDNAKNSL FLQMNSLRDD DTAVYYCARE  120
IRRASTWSAD LWGRGTLVTV SSASTKGPSV FPLAPSSKST SGGTAALGCL VKDYFPEPVT  180
VSWNSGALTS GVHTFPAVLQ SSGLYSLSSV VTVPSSSLGT QTYICNVNHK PSNTKVDKRV  240
EPKSCDKTHT CPPCPAPELL GGPSVFLFPP NPRTPS                            276

SEQ ID NO: 49          moltype = AA  length = 225
FEATURE                Location/Qualifiers
REGION                 1..225
                       note = LC variable region
source                 1..225
                       mol_type = protein
                       organism = synthetic construct
SEQUENCE: 49
METDTLLLWV LLLWVPGSTG DEIVLTQSPS SLSASVGDRV TITCRASRDI NTYLGWFQQR  60
PGKAPKSLIY GASNLQNGVP SRFSGSGSGT YFTLTINGLQ TEDFATYYCQ QYSIYPLSLG  120
GGTKADMKRT VAAPSVFIFP PSDEQLKSGT ASVVCLLNNF YPREAKVQWK VDNALQSGNS  180
QESVTEQDSK DSTYSLSSTL TLSKADYEKH KVYACEVTHQ GLSSP                  225

SEQ ID NO: 50          moltype = AA  length = 235
FEATURE                Location/Qualifiers
REGION                 1..235
                       note = LC variable region
source                 1..235
                       mol_type = protein
                       organism = synthetic construct
SEQUENCE: 50
METDTLLLWL LLLWVPGSTG DEIVLTQSPS TLSASVGDRV TITCRASQSI NNWLAWYQEK  60
PGKAPKLLIN KASSLESGVP SRFSGSGSGT EFTLTITSLQ PDDFATYYCQ QYNSNSWTFG  120
QGTKVDMKRT VAAPSVFIFP PSDEQLKSGT ASVVCLLNNF YPREAKVQWK VDNALQSGNS  180
QESVTEQDSK DSTYSLSSTL TLSKADYEKH KVYACEVTHQ GLSSPVTKSF NRGEC       235

SEQ ID NO: 51          moltype = AA  length = 241
FEATURE                Location/Qualifiers
REGION                 1..241
                       note = LC variable region
source                 1..241
                       mol_type = protein
                       organism = synthetic construct
SEQUENCE: 51
MKTDTLLLWV LLLWVPGSTG DDIVLTQSPD SLAVSLGERA TINCKSSQSV LYSSNNKNYL  60
AWYQQKPGQP PKLLIYWAST RESGVPDRFS GSGSGTDFTL TISSLQAEDV AVYYCQQYYS  120
TPPTFGQGTK VEIKRTVAAP SVFIFPPSDE QLKSGTASVV CLLNNFYPRE AKVQWKVDNA  180
LQSGNSQESV TEQDSKDSTY SLSSTLTLSK ADYEKHKVYA CEVTHQGLSS PVTKSFNRGE  240
C                                                                  241

SEQ ID NO: 52          moltype = AA  length = 237
FEATURE                Location/Qualifiers
REGION                 1..237
                       note = LC variable region
source                 1..237
```

```
                         mol_type = protein
                         organism = synthetic construct
SEQUENCE: 52
METDTLLLWV LLLWVPGSTG DLPVLTQPAS VSGSPGQSIT ISCTGTSSDV GAYNYVSWYQ  60
QHPGKAPKLI IYEVKIRPSG VSNRFSGSKS GNTASLTISG LQAEDEADYF CSSYSTNSPW  120
VFGGGTKVTV LRQPKAAPSV TLFPPSSEEL QANKATLVCL ISDFYPGAVT VAWKADSSPV  180
KAGVETTTPS KQSNNKYAAS SYLSLTPEQW KSHRSYSCQV THEGSTVEKT VAPTECS     237

SEQ ID NO: 53            moltype = AA  length = 237
FEATURE                  Location/Qualifiers
REGION                   1..237
                         note = LC variable region
source                   1..237
                         mol_type = protein
                         organism = synthetic construct
SEQUENCE: 53
METDTLLLWV LLLWVPGSTG DEIVLTQSPG TLSLSPGERA TLSCRASQSV TKNYLAWYQQ  60
KPGQAPTLVI YDASTRASGI PDRFIGSGSG TDFTLTISRL EPEDFAVYYC HQYGSSPPYT  120
FGRGTKLEIK RTVAAPSVFI FPPSDEQLKS GTASVVCLLN NFYPREAKVQ WKVDNALQSG  180
NSQESVTEQD SKDSTYSLSS TLTLSKADYE KHKVYACEVT HQGLSSPVTK SFNRGEC     237

SEQ ID NO: 54            moltype = AA  length = 238
FEATURE                  Location/Qualifiers
REGION                   1..238
                         note = LC variable region
source                   1..238
                         mol_type = protein
                         organism = synthetic construct
SEQUENCE: 54
METDTLLLWV LLLWVPGSTG DDIVMTQSPD SLAVSLGERA TINCKSSQTV LFTSYYVAWY  60
QQKPGQPPKL LFSGASSRES GVPDRFSAGG SGTDFYLTIN SLQAEDVADY YCQQYHTPPF  120
TFGGGTKLEI RRTVAAPSVF IFPPSDEQLK SGTASVVCLL NNFYPREAKV QWKVDNALQS  180
GNSQESVTEQ DSKDSTYSLS STLTLSKADY EKHKVYACEV THQGLSSPVT KSFNRGEC    238

SEQ ID NO: 55            moltype = AA  length = 235
FEATURE                  Location/Qualifiers
REGION                   1..235
                         note = LC variable region
source                   1..235
                         mol_type = protein
                         organism = synthetic construct
SEQUENCE: 55
METDTLLLWV LLLWVPGSTG DETTLTQSPA TLSVSPGETA TLSCRASQNV INNLAWYQQK  60
PGQAPRLLIY GASTRATGIP ARFSGSGSGT EFTLTISSMQ SEDFAVYYCQ QYNDWPRSFG  120
QGTRLDIRRT VAAPSVFIFP PSDEQLKSGT ASVVCLLNNF YPREAKVQWK VDNALQSGNS  180
QESVTEQDSK DSTYSLSSTL TLSKADYEKH KVYACEVTHQ GLSSPVTKSF NRGEC       235

SEQ ID NO: 56            moltype = AA  length = 237
FEATURE                  Location/Qualifiers
REGION                   1..237
                         note = LC variable region
source                   1..237
                         mol_type = protein
                         organism = synthetic construct
SEQUENCE: 56
METDTLLLWV LLLWVPGSTG DDIVLTQSPG TLSLSPGERA TLSCRASQSV NSIFLAWYQQ  60
KPGQAPRLLI YGASSRATGI PDRFSGSGSG TDFTLTISRL EPEDFAVYYC QQYHSSPKLT  120
FGGGTKVEIK RTVAAPSVFI FPPSGEQLKS GTASVVCLLN NFYPREAKVQ WKVDNALQSG  180
NSQESVTEQD SKDSTYSLSS TLTLSKADYE KHKVYACEVT HQGLSSPVTK SFNRGEC     237

SEQ ID NO: 57            moltype = AA  length = 237
FEATURE                  Location/Qualifiers
REGION                   1..237
                         note = LC variable region
source                   1..237
                         mol_type = protein
                         organism = synthetic construct
SEQUENCE: 57
METDTLLLWV LLLWVPGSTG DQSALTQPAS VSGSPGQSIT ISCTGTGSDI GGYNFVSWYQ  60
QYPGKAPKLI IYEVRIRASG VSNRFSGSKS GNTASLTISG LQAEDEADYY CNSYSIHSPW  120
VFGGGTKLTV LRQPKAAPSV TLFPPSSEEL QANKATLVCL ISDFYPGAVT VAWKADSSPV  180
KAGVETTTPS KQSNNKYAAS SYLSLTPEQW ESHRSYSCQV THEGSTVEKT VAPTECS     237

SEQ ID NO: 58            moltype = AA  length = 237
FEATURE                  Location/Qualifiers
REGION                   1..237
                         note = LC variable region
source                   1..237
                         mol_type = protein
```

```
                         organism = synthetic construct
SEQUENCE: 58
METDTLLLWV LLLWVPGSTG DQAGLTQPAS VSGSPGQSIT ISCTAANSDI GDFNFVSWYQ  60
QRPDKAPKLM VYEVSSRPSG VSNRFSGSKS GNTASLTISG LQAEDEADYY CTSYTSSSTF  120
VFGTGTKVTV LGQPKANPTV TLFPPSSEEL QANKATLVCL ISDFYPGAVT VAWKADSSPV  180
KAGVETTTPS KQSNNKYAAS SYLSLTPEQW KSHRSYSCQV THEGSTVEKT VAPTECS     237

SEQ ID NO: 59            moltype = AA  length = 236
FEATURE                  Location/Qualifiers
REGION                   1..236
                         note = LC variable region
source                   1..236
                         mol_type = protein
                         organism = synthetic construct
SEQUENCE: 59
TMETDTLLLW VLLLWVPGST GDETTLTQSP GTLSLSPGER ATLSCRASQS VSSTYLAWYQ  60
QKPGQSPRLL IYGASSRATG IPDRFSGSGS GTQFTLTINR LEPEDFAVYY CQQFGSPWTF  120
GQGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 60            moltype = AA  length = 235
FEATURE                  Location/Qualifiers
REGION                   1..235
                         note = LC variable region
source                   1..235
                         mol_type = protein
                         organism = synthetic construct
SEQUENCE: 60
METDTLLLWV LLLWVPGSTG DETTLTQSPA TLSLSPGERA TLSCRASQSV SSYLAWYQHK  60
PGQAPRLLIY GASKRATGIP SRFSGSGSGT DFSLTISSLE PEDFAVYYCQ HRSDWRTTFG  120
QGTRLEIKRT VAAPSVFIFP PSDEQLKSGT ASVVCLLNNF YPREAKVQWK VDNALQSGNS  180
QESVTEQDSK DSTYSLSSTL TLSKADYEKH KVYACEVTHQ GLSSPVTKSF NRGEC       235

SEQ ID NO: 61            moltype = AA  length = 235
FEATURE                  Location/Qualifiers
REGION                   1..235
                         note = LC variable region
source                   1..235
                         mol_type = protein
                         organism = synthetic construct
SEQUENCE: 61
METDTLLLWV LLLWVPGSTG DDIVMTQSPS TLSASVGDRV TITCRASQSI DRWLAWYQQK  60
PGKAPKLLIY QASSLERGVP SRFSGSGSGT EFTLTISSLQ PDDFATYYCQ QYNGYPLTFG  120
GGTKVEIKRT VAAPSVFIFP PSDEQLKSGT ASVVCLLNNF YPREAKVQWK VDNALQSGNS  180
QESVTEQDSK DSTYSLSSTL TLSKADYEKH KVYACEVTHQ GLSSPVTKSF NRGEC       235

SEQ ID NO: 62            moltype = AA  length = 237
FEATURE                  Location/Qualifiers
REGION                   1..237
                         note = LC variable region
source                   1..237
                         mol_type = protein
                         organism = synthetic construct
SEQUENCE: 62
METDTLLLWV LLLWVPGSTG DDIQMTQSPG TLSLSPGERA TLSCRASQSV ISYYVAWYQH  60
KGGQAPRLLI YGASSRATGV PDRFSGSGSG TDFTLTISSL EPEDFALYYC QYYGSSPLWA  120
FGQGTKVEIK RTVAAPSVFI FPPSDEQLKS GTASVVCLLN NFYPREAKVQ WKVDNALQSG  180
NSQESVTEQD SKDSTYSLSS TLTLSKADYE KHKVYACEVT HQGLSSPVTK SFNRGEC     237

SEQ ID NO: 63            moltype = AA  length = 235
FEATURE                  Location/Qualifiers
REGION                   1..235
                         note = LC variable region
source                   1..235
                         mol_type = protein
                         organism = synthetic construct
SEQUENCE: 63
METDTLLLWV LLLWVPGSTG DEIVLTQSPA TLSVSPGGRA SLSCRASQSI GDKLSWYQQK  60
PGQAPRLVIY GAYTRATDIS PRFSGSRSGT DFNLTISRMQ SGDFAVYFCQ QYENWPRTFG  120
QGTKLEIKRT VAAPSVFIFP PSDEQLKSGT ASVVCLLNNF YPREAKVQWK VDNALQSGNS  180
QESVTEQDSK DSTYSLSSTL TLSKADYEKH KVYACEVTHQ GLSSPVTKSF NRGEC       235

SEQ ID NO: 64            moltype = AA  length = 291
FEATURE                  Location/Qualifiers
REGION                   1..291
                         note = LC variable region
source                   1..291
                         mol_type = protein
                         organism = synthetic construct
```

-continued

```
SEQUENCE: 64
METDTLLLWV LLLWVPGSTG DDIQMTQSPS SLSASVGDRV IITCRASQSI SSSLNWYQQK  60
PGKAPKLLIY AAVNLETGVP SRFSGSGFGT DFTLAISNVQ PEDFATYYCQ QSDTRTFGRG  120
TKLDVKRTVA APSVFIFPPS DEQLKSGTAS VVCLLNNFYP REAKVQWKVD NALQSGNSQE  180
SVTEQDSKDS TYSLSSTLTL SKADYEKHKV YACEVTHQGL SSPVTKSFNR GEVLGGRKLG  240
RHGPTCLLQL IMVTNKAIAS QISQIKHFFH CILVVVCPNS SMYLIMSGSG I          291

SEQ ID NO: 65           moltype = AA  length = 8
FEATURE                 Location/Qualifiers
source                  1..8
                        mol_type = protein
                        organism = Homo sapiens
SEQUENCE: 65
GFNFRAYG                                                          8

SEQ ID NO: 66           moltype = AA  length = 9
FEATURE                 Location/Qualifiers
source                  1..9
                        mol_type = protein
                        organism = Homo sapiens
SEQUENCE: 66
IWSAETNRH                                                         9

SEQ ID NO: 67           moltype = AA  length = 13
FEATURE                 Location/Qualifiers
source                  1..13
                        mol_type = protein
                        organism = Homo sapiens
SEQUENCE: 67
AKARPGYDYV VDL                                                    13

SEQ ID NO: 68           moltype = AA  length = 8
FEATURE                 Location/Qualifiers
source                  1..8
                        mol_type = protein
                        organism = Homo sapiens
SEQUENCE: 68
GFSFSSYS                                                          8

SEQ ID NO: 69           moltype = AA  length = 9
FEATURE                 Location/Qualifiers
source                  1..9
                        mol_type = protein
                        organism = Homo sapiens
SEQUENCE: 69
INSDGSTKI                                                         9

SEQ ID NO: 70           moltype = AA  length = 12
FEATURE                 Location/Qualifiers
source                  1..12
                        mol_type = protein
                        organism = Homo sapiens
SEQUENCE: 70
VRLVHYDWSP FV                                                     12

SEQ ID NO: 71           moltype = AA  length = 8
FEATURE                 Location/Qualifiers
source                  1..8
                        mol_type = protein
                        organism = Homo sapiens
SEQUENCE: 71
GFTFTRFT                                                          8

SEQ ID NO: 72           moltype = AA  length = 9
FEATURE                 Location/Qualifiers
source                  1..9
                        mol_type = protein
                        organism = Homo sapiens
SEQUENCE: 72
ISSGSSDIN                                                         9

SEQ ID NO: 73           moltype = AA  length = 16
FEATURE                 Location/Qualifiers
source                  1..16
                        mol_type = protein
                        organism = Homo sapiens
SEQUENCE: 73
AKDPRSGISG RYGMDV                                                 16
```

```
SEQ ID NO: 74           moltype = AA  length = 8
FEATURE                 Location/Qualifiers
source                  1..8
                        mol_type = protein
                        organism = Homo sapiens
SEQUENCE: 74
GFMFERYS                                                    8

SEQ ID NO: 75           moltype = AA  length = 10
FEATURE                 Location/Qualifiers
source                  1..10
                        mol_type = protein
                        organism = Homo sapiens
SEQUENCE: 75
ISSLSGSHIN                                                  10

SEQ ID NO: 76           moltype = AA  length = 15
FEATURE                 Location/Qualifiers
source                  1..15
                        mol_type = protein
                        organism = Homo sapiens
SEQUENCE: 76
ARDRRSGSSP VPLDV                                            15

SEQ ID NO: 77           moltype = AA  length = 8
FEATURE                 Location/Qualifiers
source                  1..8
                        mol_type = protein
                        organism = Homo sapiens
SEQUENCE: 77
GGPFSGAY                                                    8

SEQ ID NO: 78           moltype = AA  length = 8
FEATURE                 Location/Qualifiers
source                  1..8
                        mol_type = protein
                        organism = Homo sapiens
SEQUENCE: 78
AGRSGTTN                                                    8

SEQ ID NO: 79           moltype = AA  length = 18
FEATURE                 Location/Qualifiers
source                  1..18
                        mol_type = protein
                        organism = Homo sapiens
SEQUENCE: 79
GRRQIMSLSN LYKRPVDS                                         18

SEQ ID NO: 80           moltype = AA  length = 8
FEATURE                 Location/Qualifiers
source                  1..8
                        mol_type = protein
                        organism = Homo sapiens
SEQUENCE: 80
GFTFSSYS                                                    8

SEQ ID NO: 81           moltype = AA  length = 9
FEATURE                 Location/Qualifiers
source                  1..9
                        mol_type = protein
                        organism = Homo sapiens
SEQUENCE: 81
ISSGGSSIH                                                   9

SEQ ID NO: 82           moltype = AA  length = 16
FEATURE                 Location/Qualifiers
source                  1..16
                        mol_type = protein
                        organism = Homo sapiens
SEQUENCE: 82
VRDPRSGISG RYGMDV                                           16

SEQ ID NO: 83           moltype = AA  length = 8
FEATURE                 Location/Qualifiers
source                  1..8
                        mol_type = protein
                        organism = Homo sapiens
SEQUENCE: 83
GYTFTKYG                                                    8
```

```
SEQ ID NO: 84          moltype = AA  length = 9
FEATURE                Location/Qualifiers
source                 1..9
                       mol_type = protein
                       organism = Homo sapiens
SEQUENCE: 84
ISAFNGYTR                                                       9

SEQ ID NO: 85          moltype = AA  length = 21
FEATURE                Location/Qualifiers
source                 1..21
                       mol_type = protein
                       organism = Homo sapiens
SEQUENCE: 85
ARQYPDQYSS SGWPRLFAMD V                                         21

SEQ ID NO: 86          moltype = AA  length = 8
FEATURE                Location/Qualifiers
source                 1..8
                       mol_type = protein
                       organism = Homo sapiens
SEQUENCE: 86
GFTFSRDT                                                        8

SEQ ID NO: 87          moltype = AA  length = 9
FEATURE                Location/Qualifiers
source                 1..9
                       mol_type = protein
                       organism = Homo sapiens
SEQUENCE: 87
ISSGSSDIN                                                       9

SEQ ID NO: 88          moltype = AA  length = 16
FEATURE                Location/Qualifiers
source                 1..16
                       mol_type = protein
                       organism = Homo sapiens
SEQUENCE: 88
ARDPRSGISG RYGMDV                                               16

SEQ ID NO: 89          moltype = AA  length = 8
FEATURE                Location/Qualifiers
source                 1..8
                       mol_type = protein
                       organism = Homo sapiens
SEQUENCE: 89
GFTFSTYS                                                        8

SEQ ID NO: 90          moltype = AA  length = 10
FEATURE                Location/Qualifiers
source                 1..10
                       mol_type = protein
                       organism = Homo sapiens
SEQUENCE: 90
ISSRSGSHIN                                                      10

SEQ ID NO: 91          moltype = AA  length = 15
FEATURE                Location/Qualifiers
source                 1..15
                       mol_type = protein
                       organism = Homo sapiens
SEQUENCE: 91
ARDRRSGTSP LPLDV                                                15

SEQ ID NO: 92          moltype = AA  length = 9
FEATURE                Location/Qualifiers
source                 1..9
                       mol_type = protein
                       organism = Homo sapiens
SEQUENCE: 92
GYSISSGYY                                                       9

SEQ ID NO: 93          moltype = AA  length = 8
FEATURE                Location/Qualifiers
source                 1..8
                       mol_type = protein
                       organism = Homo sapiens
SEQUENCE: 93
```

-continued

```
IYRSGSTY                                                              8

SEQ ID NO: 94          moltype = AA  length = 31
FEATURE                Location/Qualifiers
source                 1..31
                       mol_type = protein
                       organism = Homo sapiens
SEQUENCE: 94
ARSGIKVADD YYYEMDVWGQ GTDDYSYAMD V                                    31

SEQ ID NO: 95          moltype = AA  length = 8
FEATURE                Location/Qualifiers
source                 1..8
                       mol_type = protein
                       organism = Homo sapiens
SEQUENCE: 95
GFTFSSYS                                                              8

SEQ ID NO: 96          moltype = AA  length = 9
FEATURE                Location/Qualifiers
source                 1..9
                       mol_type = protein
                       organism = Homo sapiens
SEQUENCE: 96
ISSGSSYIE                                                             9

SEQ ID NO: 97          moltype = AA  length = 15
FEATURE                Location/Qualifiers
source                 1..15
                       mol_type = protein
                       organism = Homo sapiens
SEQUENCE: 97
ARHTARIDSY HGMDV                                                      15

SEQ ID NO: 98          moltype = AA  length = 8
FEATURE                Location/Qualifiers
source                 1..8
                       mol_type = protein
                       organism = Homo sapiens
SEQUENCE: 98
GESFNGFF                                                              8

SEQ ID NO: 99          moltype = AA  length = 8
FEATURE                Location/Qualifiers
source                 1..8
                       mol_type = protein
                       organism = Homo sapiens
SEQUENCE: 99
INHLASTG                                                              8

SEQ ID NO: 100         moltype = AA  length = 18
FEATURE                Location/Qualifiers
source                 1..18
                       mol_type = protein
                       organism = Homo sapiens
SEQUENCE: 100
ARGYSYGFAW PNYHYLDV                                                   18

SEQ ID NO: 101         moltype = AA  length = 8
FEATURE                Location/Qualifiers
source                 1..8
                       mol_type = protein
                       organism = Homo sapiens
SEQUENCE: 101
GFTFSSHA                                                              8

SEQ ID NO: 102         moltype = AA  length = 9
FEATURE                Location/Qualifiers
source                 1..9
                       mol_type = protein
                       organism = Homo sapiens
SEQUENCE: 102
FSGSSGTTK                                                             9

SEQ ID NO: 103         moltype = AA  length = 17
FEATURE                Location/Qualifiers
source                 1..17
                       mol_type = protein
                       organism = Homo sapiens
```

-continued

```
SEQUENCE: 103
AKGFSPFRGV QFPYFDY                                           17

SEQ ID NO: 104          moltype = AA  length = 8
FEATURE                 Location/Qualifiers
source                  1..8
                        mol_type = protein
                        organism = Homo sapiens
SEQUENCE: 104
GFTFKSYS                                                     8

SEQ ID NO: 105          moltype = AA  length = 9
FEATURE                 Location/Qualifiers
source                  1..9
                        mol_type = protein
                        organism = Homo sapiens
SEQUENCE: 105
ITSGGSKTY                                                    9

SEQ ID NO: 106          moltype = AA  length = 15
FEATURE                 Location/Qualifiers
source                  1..15
                        mol_type = protein
                        organism = Homo sapiens
SEQUENCE: 106
ARSLHSTSQP SYMDV                                             15

SEQ ID NO: 107          moltype = AA  length = 8
FEATURE                 Location/Qualifiers
source                  1..8
                        mol_type = protein
                        organism = Homo sapiens
SEQUENCE: 107
GVSTRNYY                                                     8

SEQ ID NO: 108          moltype = AA  length = 8
FEATURE                 Location/Qualifiers
source                  1..8
                        mol_type = protein
                        organism = Homo sapiens
SEQUENCE: 108
IFNIGTTN                                                     8

SEQ ID NO: 109          moltype = AA  length = 13
FEATURE                 Location/Qualifiers
source                  1..13
                        mol_type = protein
                        organism = Homo sapiens
SEQUENCE: 109
ASGFEYGDYT FDY                                               13

SEQ ID NO: 110          moltype = AA  length = 8
FEATURE                 Location/Qualifiers
source                  1..8
                        mol_type = protein
                        organism = Homo sapiens
SEQUENCE: 110
GFNFNKYN                                                     8

SEQ ID NO: 111          moltype = AA  length = 9
FEATURE                 Location/Qualifiers
source                  1..9
                        mol_type = protein
                        organism = Homo sapiens
SEQUENCE: 111
ISALSTYIY                                                    9

SEQ ID NO: 112          moltype = AA  length = 14
FEATURE                 Location/Qualifiers
source                  1..14
                        mol_type = protein
                        organism = Homo sapiens
SEQUENCE: 112
AREIRRASTW SADL                                              14

SEQ ID NO: 113          moltype = AA  length = 6
FEATURE                 Location/Qualifiers
source                  1..6
                        mol_type = protein
```

-continued

```
                      organism = Homo sapiens
SEQUENCE: 113
RDINTY                                                                6

SEQ ID NO: 114        moltype = AA  length = 9
FEATURE               Location/Qualifiers
source                1..9
                      mol_type = protein
                      organism = Homo sapiens
SEQUENCE: 114
QQYSIYPLS                                                             9

SEQ ID NO: 115        moltype = AA  length = 6
FEATURE               Location/Qualifiers
source                1..6
                      mol_type = protein
                      organism = Homo sapiens
SEQUENCE: 115
QSINNW                                                                6

SEQ ID NO: 116        moltype = AA  length = 9
FEATURE               Location/Qualifiers
source                1..9
                      mol_type = protein
                      organism = Homo sapiens
SEQUENCE: 116
QQYNSNSWT                                                             9

SEQ ID NO: 117        moltype = AA  length = 12
FEATURE               Location/Qualifiers
source                1..12
                      mol_type = protein
                      organism = Homo sapiens
SEQUENCE: 117
QSVLYSSNNK NY                                                         12

SEQ ID NO: 118        moltype = AA  length = 9
FEATURE               Location/Qualifiers
source                1..9
                      mol_type = protein
                      organism = Homo sapiens
SEQUENCE: 118
QQYYSTPPT                                                             9

SEQ ID NO: 119        moltype = AA  length = 9
FEATURE               Location/Qualifiers
source                1..9
                      mol_type = protein
                      organism = Homo sapiens
SEQUENCE: 119
SSDVGAYNY                                                             9

SEQ ID NO: 120        moltype = AA  length = 10
FEATURE               Location/Qualifiers
source                1..10
                      mol_type = protein
                      organism = Homo sapiens
SEQUENCE: 120
SSYSTNSPWV                                                            10

SEQ ID NO: 121        moltype = AA  length = 7
FEATURE               Location/Qualifiers
source                1..7
                      mol_type = protein
                      organism = Homo sapiens
SEQUENCE: 121
QSVTKNY                                                               7

SEQ ID NO: 122        moltype = AA  length = 10
FEATURE               Location/Qualifiers
source                1..10
                      mol_type = protein
                      organism = Homo sapiens
SEQUENCE: 122
HQYGSSPPYT                                                            10

SEQ ID NO: 123        moltype = AA  length = 9
FEATURE               Location/Qualifiers
source                1..9
```

```
                        mol_type = protein
                        organism = Homo sapiens
SEQUENCE: 123
QTVLFTSYY                                                     9

SEQ ID NO: 124          moltype = AA  length = 9
FEATURE                 Location/Qualifiers
source                  1..9
                        mol_type = protein
                        organism = Homo sapiens
SEQUENCE: 124
QQYHTPPFT                                                     9

SEQ ID NO: 125          moltype = AA  length = 6
FEATURE                 Location/Qualifiers
source                  1..6
                        mol_type = protein
                        organism = Homo sapiens
SEQUENCE: 125
QNVINN                                                        6

SEQ ID NO: 126          moltype = AA  length = 9
FEATURE                 Location/Qualifiers
source                  1..9
                        mol_type = protein
                        organism = Homo sapiens
SEQUENCE: 126
QQYNDWPRS                                                     9

SEQ ID NO: 127          moltype = AA  length = 7
FEATURE                 Location/Qualifiers
source                  1..7
                        mol_type = protein
                        organism = Homo sapiens
SEQUENCE: 127
QSVNSIF                                                       7

SEQ ID NO: 128          moltype = AA  length = 10
FEATURE                 Location/Qualifiers
source                  1..10
                        mol_type = protein
                        organism = Homo sapiens
SEQUENCE: 128
QQYHSSPKLT                                                    10

SEQ ID NO: 129          moltype = AA  length = 9
FEATURE                 Location/Qualifiers
source                  1..9
                        mol_type = protein
                        organism = Homo sapiens
SEQUENCE: 129
GSDIGGYNF                                                     9

SEQ ID NO: 130          moltype = AA  length = 10
FEATURE                 Location/Qualifiers
source                  1..10
                        mol_type = protein
                        organism = Homo sapiens
SEQUENCE: 130
NSYSIHSPWV                                                    10

SEQ ID NO: 131          moltype = AA  length = 9
FEATURE                 Location/Qualifiers
source                  1..9
                        mol_type = protein
                        organism = Homo sapiens
SEQUENCE: 131
NSDIGDFNF                                                     9

SEQ ID NO: 132          moltype = AA  length = 10
FEATURE                 Location/Qualifiers
source                  1..10
                        mol_type = protein
                        organism = Homo sapiens
SEQUENCE: 132
TSYTSSSTFV                                                    10

SEQ ID NO: 133          moltype = AA  length = 7
FEATURE                 Location/Qualifiers
```

```
source                1..7
                      mol_type = protein
                      organism = Homo sapiens
SEQUENCE: 133
QSVSSTY                                                    7

SEQ ID NO: 134        moltype = AA  length = 8
FEATURE               Location/Qualifiers
source                1..8
                      mol_type = protein
                      organism = Homo sapiens
SEQUENCE: 134
QQFGSPWT                                                   8

SEQ ID NO: 135        moltype = AA  length = 6
FEATURE               Location/Qualifiers
source                1..6
                      mol_type = protein
                      organism = Homo sapiens
SEQUENCE: 135
QSVSSY                                                     6

SEQ ID NO: 136        moltype = AA  length = 9
FEATURE               Location/Qualifiers
source                1..9
                      mol_type = protein
                      organism = Homo sapiens
SEQUENCE: 136
QHRSDWRTT                                                  9

SEQ ID NO: 137        moltype = AA  length = 6
FEATURE               Location/Qualifiers
source                1..6
                      mol_type = protein
                      organism = Homo sapiens
SEQUENCE: 137
QSIDRW                                                     6

SEQ ID NO: 138        moltype = AA  length = 9
FEATURE               Location/Qualifiers
source                1..9
                      mol_type = protein
                      organism = Homo sapiens
SEQUENCE: 138
QQYNGYPLT                                                  9

SEQ ID NO: 139        moltype = AA  length = 7
FEATURE               Location/Qualifiers
source                1..7
                      mol_type = protein
                      organism = Homo sapiens
SEQUENCE: 139
QSVISYY                                                    7

SEQ ID NO: 140        moltype = AA  length = 10
FEATURE               Location/Qualifiers
source                1..10
                      mol_type = protein
                      organism = Homo sapiens
SEQUENCE: 140
QYYGSSPLWA                                                 10

SEQ ID NO: 141        moltype = AA  length = 6
FEATURE               Location/Qualifiers
source                1..6
                      mol_type = protein
                      organism = Homo sapiens
SEQUENCE: 141
QSIGDK                                                     6

SEQ ID NO: 142        moltype = AA  length = 9
FEATURE               Location/Qualifiers
source                1..9
                      mol_type = protein
                      organism = Homo sapiens
SEQUENCE: 142
QQYENWPRT                                                  9

SEQ ID NO: 143        moltype = AA  length = 6
```

-continued

```
FEATURE                 Location/Qualifiers
source                  1..6
                        mol_type = protein
                        organism = Homo sapiens
SEQUENCE: 143
QSISSS                                                         6

SEQ ID NO: 144          moltype = AA  length = 7
FEATURE                 Location/Qualifiers
source                  1..7
                        mol_type = protein
                        organism = Homo sapiens
SEQUENCE: 144
QQSDTRT                                                        7
```

What is claimed is:

1. An antigen-binding composition comprising a combination of three recombinant monoclonal neutralizing antibodies or neutralizing antigen-binding antibody fragments thereof, which are specific to Lassa virus glycoprotein, wherein the composition comprises:

a recombinant human monoclonal antibody or an antigen-binding antibody fragment thereof comprising a $V_H$ CDR1 of SEQ ID NO: 83, a $V_H$ CDR2 of SEQ ID NO: 84, a $V_H$ CDR3 of SEQ ID NO: 85, a $V_L$ CDR1 of SEQ ID NO: 125, a $V_L$ CDR2 of sequence Gly Ala Ser, and a $V_L$ CDR3 of SEQ ID NO: 126;

a recombinant human monoclonal antibody or an antigen-binding antibody fragment thereof comprising a $V_H$ CDR1 of SEQ ID NO: 92, a $V_H$ CDR2 of SEQ ID NO: 93, a $V_H$ CDR3 of SEQ ID NO: 94, a $V_L$ CDR1 of SEQ ID NO: 131, a $V_L$ CDR2 of sequence Glu Val Ser, and a $V_L$ CDR3 of SEQ ID NO: 132; and a recombinant human monoclonal antibody or an antigen-binding antibody fragment thereof comprising a $V_H$ CDR1 of SEQ ID NO: 98, a $V_H$ CDR2 of SEQ ID NO: 99, a $V_H$ CDR3 of SEQ ID NO: 100, a $V_L$ CDR1 of SEQ ID NO: 135, a $V_L$ CDR2 of sequence Gly Ala Ser, and a $V_L$ CDR3 of SEQ ID NO: 136.

2. The composition of claim 1, wherein each antigen-binding antibody fragment is selected from the group consisting of a Fab, a Fab', and a $F(ab')_2$ fragment.

3. A pharmaceutical composition for treating a Lassa virus or a lymphocytic choriomeningitis virus infection comprising the composition of claim 1 and a pharmaceutically acceptable carrier.

4. The composition of claim 1 wherein the composition comprises:

a recombinant human monoclonal antibody or an antigen-binding antibody fragment thereof comprising a $V_H$ of SEQ ID NO: 39 and a $V_L$ of SEQ ID NO: 55;

a recombinant human monoclonal antibody or an antigen-binding antibody fragment thereof comprising a $V_H$ of SEQ ID NO: 42 and a $V_L$ of SEQ ID NO: 58; and a recombinant human monoclonal antibody or an antigen-binding antibody fragment thereof comprising a $V_H$ of SEQ ID NO: 44 and a $V_L$ of SEQ ID NO: 60.

5. The composition of claim 4, wherein each antigen-binding antibody fragment is selected from the group consisting of a Fab, a Fab', and a $F(ab')_2$ fragment.

6. A pharmaceutical composition for treating infection by a Lassa virus or a lymphocytic choriomeningitis virus comprising the composition of claim 4 and a pharmaceutically acceptable carrier.

7. An antigen-binding composition comprising a recombinant human monoclonal neutralizing antibody or a neutralizing antigen-binding antibody fragment thereof, which is specific for Lassa virus glycoprotein; the antibody or antibody fragment thereof comprising a $V_H$ CDR1 of SEQ ID NO: 83, a $V_H$ CDR2 of SEQ ID NO: 84, a $V_H$ CDR3 of SEQ ID NO: 85, a $V_L$ CDR1 of SEQ ID NO: 125, a $V_L$ CDR2 of sequence Gly Ala Ser, and a $V_L$ CDR3 of SEQ ID NO: 126.

8. The composition of claim 7, wherein the antigen-binding antibody fragment is selected from the group consisting of a Fab, a Fab', and a $F(ab')_2$ fragment.

9. The composition of claim 7 wherein the composition comprises a recombinant human monoclonal antibody or an antigen-binding antibody fragment thereof comprising a $V_H$ of SEQ ID NO: 39 and a $V_L$ of SEQ ID NO: 55.

10. A pharmaceutical composition for treating infection by a Lassa virus or a lymphocytic choriomeningitis virus comprising the composition of claim 7 and a pharmaceutically acceptable carrier.

11. An antigen-binding composition comprising a recombinant human monoclonal neutralizing antibody or a neutralizing antigen-binding antibody fragment thereof, which is specific for Lassa virus glycoprotein; the antibody or antibody fragment thereof comprising a $V_H$ CDR1 of SEQ ID NO: 92, a $V_H$ CDR2 of SEQ ID NO: 93, a $V_H$ CDR3 of SEQ ID NO: 94, a $V_L$ CDR1 of SEQ ID NO: 131, a $V_L$ CDR2 of sequence Glu Val Ser, and a $V_L$ CDR3 of SEQ ID NO: 132.

12. The composition of claim 11, wherein the antigen-binding antibody fragment is selected from the group consisting of a Fab, a Fab', and a $F(ab')_2$ fragment.

13. The composition of claim 11, wherein the composition comprises a recombinant human monoclonal antibody or an antigen-binding antibody fragment thereof comprising a $V_H$ of SEQ ID NO: 42 and a $V_L$ of SEQ ID NO: 58.

14. A pharmaceutical composition for treating infection by a Lassa virus or a lymphocytic choriomeningitis virus comprising the composition of claim 11 and a pharmaceutically acceptable carrier.

15. A method of treating or preventing a Lassa virus infection or a lymphocytic choriomeningitis virus infection in a subject comprising administering the composition of claim 1 to the subject.

16. A method of treating or preventing a Lassa virus infection or a lymphocytic choriomeningitis virus infection in a subject comprising administering the composition of claim 4 to the subject.

17. A method of treating or preventing a Lassa virus infection or a lymphocytic choriomeningitis virus infection in a subject comprising administering the composition of claim 7 to the subject.

18. A method of treating or preventing a Lassa virus infection or a lymphocytic choriomeningitis virus infection in a subject comprising administering the composition of claim 9 to the subject.

19. A method of treating or preventing a Lassa virus infection in a subject comprising administering the composition of claim 11 to the subject.

20. A method of treating or preventing a Lassa virus infection in a subject comprising administering the composition of claim 13 to the subject.

* * * * *